US011519005B2

(12) United States Patent
Magor et al.

(10) Patent No.: US 11,519,005 B2
(45) Date of Patent: Dec. 6, 2022

(54) RETINOIC ACID-INDUCIBLE GENE I PROMOTER AND COMPOSITIONS AND METHODS RELATING TO SAME

(71) Applicant: THE GOVERNORS OF THE UNIVERSITY OF ALBERTA, Edmonton (CA)

(72) Inventors: Katharine Magor, Edmonton (CA); Yanna Xiao, Edmonton (CA)

(*) Notice: Subject to any disclaimer, the term of this patent is extended or adjusted under 35 U.S.C. 154(b) by 98 days.

(21) Appl. No.: 16/650,309

(22) PCT Filed: Sep. 26, 2018

(86) PCT No.: PCT/CA2018/051216
§ 371 (c)(1),
(2) Date: Mar. 24, 2020

(87) PCT Pub. No.: WO2019/060993
PCT Pub. Date: Apr. 4, 2019

(65) Prior Publication Data
US 2020/0224217 A1 Jul. 16, 2020

Related U.S. Application Data

(60) Provisional application No. 62/564,867, filed on Sep. 28, 2017.

(51) Int. Cl.
*C12N 15/00* (2006.01)
*C12N 15/85* (2006.01)
*A01K 67/027* (2006.01)
*C12N 15/873* (2010.01)
*C12N 15/90* (2006.01)

(52) U.S. Cl.
CPC ...... *C12N 15/8509* (2013.01); *A01K 67/0275* (2013.01); *C12N 15/873* (2013.01); *C12N 15/90* (2013.01); *A01K 2217/072* (2013.01); *A01K 2217/203* (2013.01); *A01K 2227/30* (2013.01); *A01K 2267/02* (2013.01); *C12Y 306/04013* (2013.01)

(58) Field of Classification Search
None
See application file for complete search history.

(56) References Cited

U.S. PATENT DOCUMENTS

| | | | |
|---|---|---|---|
| 5,162,215 A | 11/1992 | Bosselman et al. |
| 7,312,374 B2 | 12/2007 | Rapp et al. |
| 7,323,619 B2 | 1/2008 | Baltimore et al. |
| 7,375,258 B2 | 5/2008 | Harvey et al. |
| 7,507,873 B2 | 3/2009 | Harvey et al. |
| 7,550,650 B2 | 6/2009 | Rapp et al. |
| 8,507,749 B2 | 8/2013 | Ivarie et al. |
| 9,510,571 B2 | 12/2016 | Kyogoku et al. |
| 2002/0108132 A1 | 8/2002 | Rapp |
| 2003/0115622 A1 | 6/2003 | Ponce De Leon et al. |
| 2006/0075513 A1 | 4/2006 | Ivarie et al. |
| 2006/0206952 A1 | 9/2006 | Van de Lavoir et al. |
| 2008/0108067 A1 | 5/2008 | Fisher et al. |
| 2009/0158449 A1 | 6/2009 | Nakaishi et al. |
| 2011/0247091 A1 | 10/2011 | Magor et al. |

FOREIGN PATENT DOCUMENTS

| | | |
|---|---|---|
| CN | 106256909 | 12/2016 |
| WO | WO 1987/05325 | 9/1987 |
| WO | WO 1999/42569 | 8/1999 |
| WO | 2005084430 | 9/2005 |
| WO | WO 2006/047311 | 5/2006 |

OTHER PUBLICATIONS

Song, 2014, Biol. Reprod. vol. 90, No. 1, Article 15, p. 1-8.*
"PREDICTED: Taeniopygia guttata DEAD (Asp-Glu-Ala-Asp) box polypeptide 58 (DDX58), mRNA.", (2013), NCBI Reference Sequence: XM_002194524.
Abu-Bonsrah et al., (2016) "CRISPR/Cas9 Targets Chicken Embryonic Somatic Cells In Vitro and In Vivo and generates Phenotypic Abnormalities", Scientific Reports 6(34524): 1-10.
Akira et al., (2006) "Pathogen recognition and innate immunity.", Cell, 124(4):783-801.
Barber et al., (2010) "Association of RIG-I with innate immunity of ducks to influenza", PNAS, 107(13):5913-5918.
Barber et al., (2013) "Identification of avian RIG-I responsive genes during influenza infection", 54(1):89-97.
Blyth et al., 2015, "Duck Interferon-Inducible Transmembrane Protein 3 Mediates Restriction of Influenza Viruses", Journal of Virology, 90(1)103-116.
Chen et al., (2013) "Molecular characterization, expression patterns, and subcellular localization of RIG-I in the Jinding Duck (*Anas platyrhynchos domesticus*)", Developmental and Comparative Immunology, (41)766-771.
Delneste et al., (2007) "Innate immunity: structure and function of TLRs", Med Sci (Paris), 23(1):67-73.
Dimitrov et al., (2016) "Germline Gene Editing in Chickens by Efficient CRISPR-Mediated Homologous Recombination in Primordial Germ Cells", PloS One 11(4):1-10, e0154303.
Doran et al., (2016), "Advances in genetic engineering of the avian genome: Realising the promise", Transgenic Res, (25)307-319.
Esnault et al., (2011), "A novel chicken lung epithelial cell line: Characterization and response to low pathogenicity avian influenza virus", Virus Research, 159(1):32-42.

(Continued)

*Primary Examiner* — Michael C Wilson
(74) *Attorney, Agent, or Firm* — Bennett Jones LLP

(57) ABSTRACT

The present disclosure provides a promoter having at least the core components of a duck retinoic acid-inducible gene I (RIG-I) promoter, as well as expression constructs having the duck RIG-I promoter operably linked to a gene product-encoding nucleic acid (e.g., an avian RIG-I protein), and recombinant host cells containing the duck RIG-I promoter, e.g., in such expression constructs. The present disclosure also provide animals genetically modified to have a gene encoding a duck RIG-I promoter operably linked to a gene product-encoding nucleic acid (e.g., an avian RIG-I protein, such as a duck RIG-I protein).

5 Claims, 17 Drawing Sheets
Specification includes a Sequence Listing.

(56) References Cited

OTHER PUBLICATIONS

Gack et al., (2007) "TRIM25 RING-finger E3 ubiquitin ligase is essential for RIG-I-mediated antiviral activity.", Nature, 446(7138):916-920.
GenBank Accession AF038963.1 "*Homo sapiens* RNA helicase (RIGI) mRNA, complete cds" dated Mar. 12, 1999.
GenBank Accession EU363349.1 "Anas platyrhynchos retinoic acid inducible protein I mRNA, complete cds" dated Apr. 8, 2010.
GenBank Accession: ADV58759.1 "Retinoic acid inducible protein I [Anser anser]" dated Mar. 23, 2011.
GenBank Accession: AGX27431.1 "Retinoic acid inducible protein I [Cairina moschata]" dated Feb. 11, 2015.
GenBank Accession: KF905228.1 "Aquila chrysaetos mitochondrion, complete genome" dated May 7, 2014.
GenBank Accession: KFO06723.1 "Putative ATP-dependent RNA helicase DDX58, partial [Balearica regulorum gibbericeps]" dated Nov. 6, 2014.
GenBank Accession: KFO59778.1 "Putative ATP-dependent RNA helicase DDX58, partial [Corvus brachyrhynchos]" dated Sep. 4, 2014.
GenBank Accession: KFP02435.1 "Putative ATP-dependent RNA helicase DDX58, partial [Calypte anna]" dated Sep. 4, 2014.
GenBank Accession: KFP10984.1 "Putative ATP-dependent RNA helicase DDX58, partial [Egretta garzetta]" dated Sep. 4, 2014.
GenBank Accession: KFP36728.1 "Comparative genomics reveals insights into avian genome evolution and adaptation" dated Nov. 14, 2014.
GenBank Accession: KFP82392.1 "Putative ATP-dependent RNA helicase DDX58, partial [Acanthisitta chloris]" dated Sep. 5, 2014.
GenBank Accession: KFQ30270.1 "Putative ATP-dependent RNA helicase DDX58, partial [Merops nubicus]" dated Sep. 5, 2014.
GenBank Accession: KFR01539.1 "Putative ATP-dependent RNA helicase DDX58, partial [Opisthocomus hoazin]" dated Sep. 5, 2014.
GenBank Accession: KFV18917.1 "Putative ATP-dependent RNA helicase DDX58, partial [Tauraco erythrolophus]" dated Sep. 5, 2014.
GenBank Accession: KFV61638.1. "Putative ATP-dependent RNA helicase DDX58, partial [Dryobates pubescens]" dated Sep. 5, 2014.
GenBank Accession: KFV82733.1 "Putative ATP-dependent RNA helicase DDX58, partial [Struthio camelus australis]" dated Sep. 5, 2014.
GenBank Accession: KFW80420.1 "Putative ATP-dependent RNA helicase DDX58, partial [Manacus vitellinus]" dated Sep. 8, 2014.
GenBank Accession: KFZ58430.1 "Putative ATP-dependent RNA helicase DDX58, partial [Podiceps cristatus]" dated Sep. 10, 2014.
GenBank Accession: KJ124555.1. "Anser cygnoides mitochondrion, complete genome" dated Mar. 19, 2014.
Harris et al., (2002) "AID Is Essential for Immunoglobulin V Gene Conversion in a Cultured B Cell Line", Current Biology, 12(5):435-438.
He et al., (2016) "Knock-in of large reporter genes in human cells via CRISPR/Cas9-induced homology-dependent and independent DNA repair", Nucleic Acids Research, 44(9):1-14, e85.
Homung et al., (2006) "5'-Triphosphate RNA is the ligand for RIG-I.", Science, 314(5801):994-997.
Hsu et al., (2014) "Development and Applications of CRISPR-Cas9 for Genome Engineering", Cell, (157)1262-1278.
Huang et al., (2013) "The duck genome and transcriptome provide insight into an avian influenza virus reservoir species.", Nat Genet, 45(7):776-783.
Hulse-Post et al., (2005) "Role of domestic ducks in the propagation and biological evolution of highly pathogenic H5N1 influenza viruses in Asia.", PNAS, 102(30):10682-10687.
Jang et al., (2015) "An Overview of Pathogen Recognition Receptors for Innate Immunity in Dental Pulp.", Mediators Inflamm, 794143:1-12.

Jiang et al., (2011) "Structural basis of RNA recognition and activation by innate immune receptor RIG-I.", Nature, 479(7373):423-427.
Kang et al., (2002) "An interferon-inducible putative RNA helicase with doublestranded RNA-dependent ATPase activity and melanoma growth-suppressive properties." PNAS, 99(2):637-642.
Kang et al., (2004) "Expression analysis and genomic characterization of human melanoma differentiation associated gene-5, mda-5: a novel type I interferon-responsive apoptosis-inducing gene.", Oncogene, 23(9):1789-1800.
Karpala et al., (2011) "Characterization of Chicken Mda5 Activity: Regulation of IFN-β in the Absence of RIG-I Functionality" Journal of Immunology, 186(9):5397-5405.
Kato et al., (2008) "Length-dependent recognition of double-stranded ribonucleic acids by retinoic acid-inducible gene-I and melanoma differentiation-associated gene 5.", *J Exp Med*, 205(1), 1601-1610.
Kawai et al., (2005) "IPS-1, an adaptor triggering RIG-I- and Mda5-mediated type I interferon induction.", Nat Immunol, 6(10):981-988.
Kawai et al., (2010) "The role of pattern-recognition receptors in innate immunity: update on Toll-like receptors.", Nat Immunol, 11(5):373-384.
Kim et al., (2009) "Ducks: the "Trojan horses" of H5N1 influenza." Influenza Other Respir Viruses, 3(4):121-128.
Kim et al., (2016) "Multilayered regulations of RIG-I in the anti-viral signaling pathway.", J Microbiol, 54(9):583-587.
Liniger et al., (2012), "Chicken Cells Sense Influenza A Virus Infection through MDA5 and CARDIF Signaling Involving LGP2", Journal of Virology, 86(2):705-717.
Loo et al., (2011) "Immune signaling by RIG-I-like receptors.", Immunity, 34(5):680-692.
Lu et al., (2010) "The structural basis of 5' triphosphate double-stranded RNA recognition by RIG-I C-terminal domain.", Structure, 18(8):1032-1043.
Luo (2011) "Structural insights into RNA recognition by RIG-I.", Cell, 147(2):409-422.
Martin-Vicente et al., (2017) "TRIM25 in the Regulation of the Antiviral Innate Immunity.", 8:1187, 1-9.
NCBI Reference Sequence: XP_013225185.1 "PREDICTED: probable ATP-dependent RNA helicase DDX58 [Columba livia]" dated Aug. 13, 2015.
Park et al., (2014) "Targeted gene knockout in chickens mediated by TALENs", PNAS, (111)12716-12721.
Schaefer-Klein et al., (1998) "The EV-O-derived cell line DF-1 supports the efficient replication of avian leukosis-sarcoma viruses and vectors.", Virology, 248(2):305-311.
Seth et al., (2005) "Identification and characterization of MAVS, a mitochondrial antiviral signaling protein that activates NF-kappaB and IRF 3.", Cell, 122(5):669-682.
Song et al., (2014) "Characteristics of Long-Term Cultures of Avian Primordial Germ Cells and Gonocytes[1]" Biology of Reproduction, 90(1): 15, 1-8.
Su et al., (2007) "Central role of interferon regulatory factor-1 (IRF-1) in controlling retinoic acid inducible gene-I (RIG-I) expression.", J. Cell Physiol, 213(2):502-510.
Tanaka et al., (1994) "Chick production by in vitro fertilization of the fowl ovum", Journal of Reproduction and Fertility, (100)447-449.
Tyack et al., (2013) "A new method for producing transgenic birds via direct in vivo transfection of primordial germ cells", Transgenic Research, (22)1257-1264.
Villota-Herdoiza et al., (2013) "Transcriptional regulation of teleost Aicda genes. Part 1—suppressors of promiscuous promoters.", Fish Shellfish Immunol, 35(6):1981-1987.
Wilkins (2010) "Recognition of viruses by cytoplasmic sensors.", Curr Opin Immunol, 22(1):41-47.
Yoneyama (2005) "Shared and unique functions of the DExD/H-box helicases RIG-I, MDA5, and LGP2 in antiviral innate immunity.", J Immunol, 175(5):2851-2858.
Yu et al., (2017) "Identification of DNA methylation and transcriptional regulatory regions in the promoter of duck retinoic acid inducible gene I (RIG-I)", PubMed, 1 page.

(56) References Cited

OTHER PUBLICATIONS

Zhang et al., (2016) "Promoter structures and differential responses to viral and non-viral inducers of chicken melanoma differentiation-associated gene 5." Mol Immunol, 76:1-6.
Zhang et al., (2017) "Identification of DNA methylation and transcriptional regulatory regions in the promoter of duck retinoic acid inducible gene I (RIG-I)", British Poultry Science, 1466-1799.
Zuo et al., (2016) "Site-Directed Genome Knockout in Chicken Cell Line and Embryos Can Use CRISPR/Cas Gene Editing Technology." 6(6): 1787-1792.

* cited by examiner

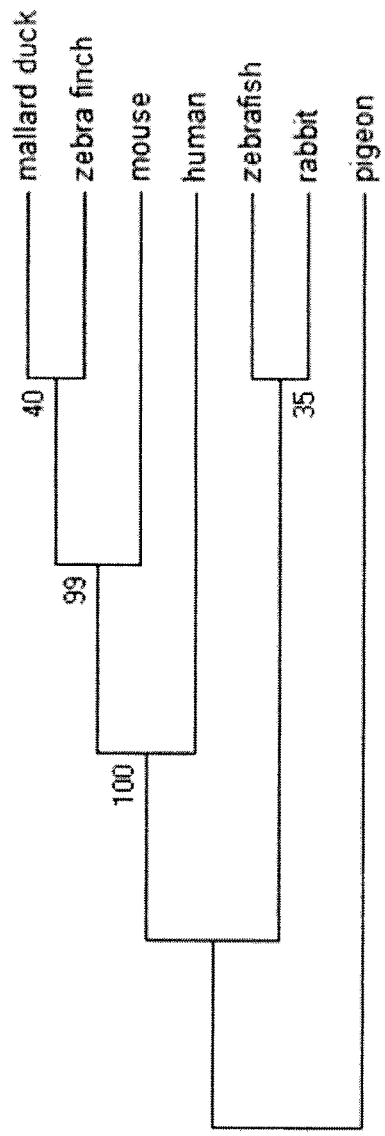
Figure 5A  RIG-I promoter phylogenetic tree
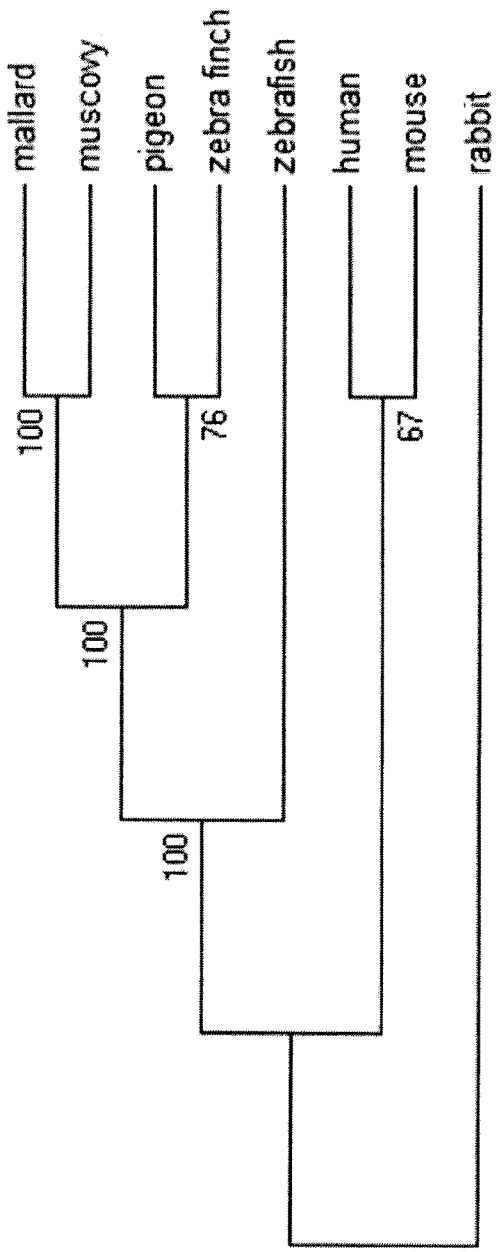
Figure 5B  RIG-I protein phylogenetic tree

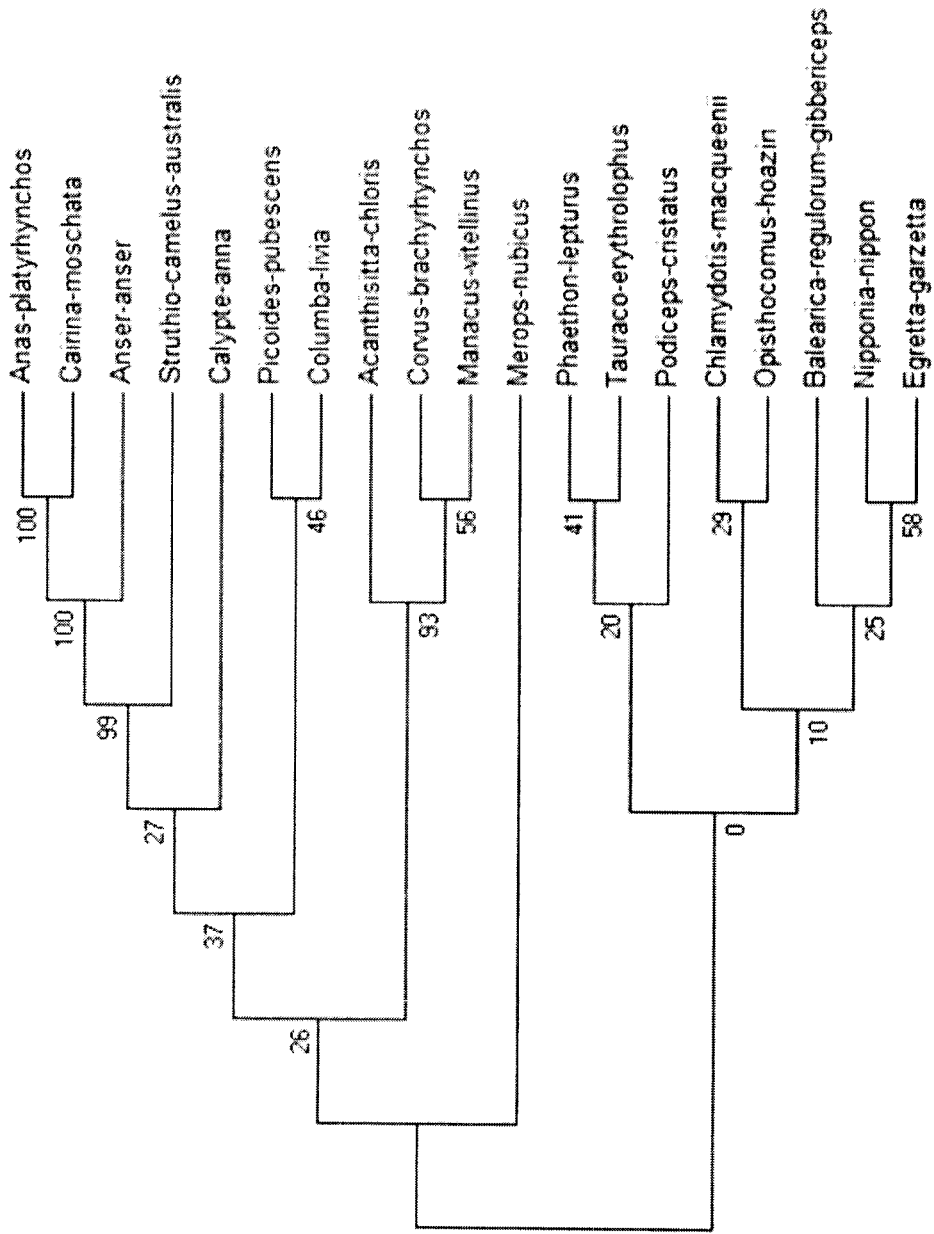
Figure 5C. Phylogenetic tree of avian RIG-I proteins

Figure 6

>duck RIG-I promoter (-2024 to -1)
AGCTGATGACCTGCAAAAGTTGGACATGCAAAATTTAAAGCTGAGGAACACAACTACACACTATGTCTGAAAAAGAAA
AAATAATAACAATCAAGAAAAAGCATTTATTCCCACCAGTGGACCACACACTCTAAGGCAGGACTTGGTGGGTCACAC
AGGGACCCTTCCAGACACAGCCACAAGTGATTTGGGAAAAAGTAACATATTCCTACACCCTTGCTAGAAGTTCTCCAGA
AAACTGCTCAGCACCATGGTTTGCAGTAGCACAAGCAGGTTAAGGTCTTCCCAGTGCTGCGAGCTTCTTCACCGATGTG
CTTGGCCACTGCAACCACCAGTTACGATGTAGCATAAAACAGCACTGAGGATATGAGCACTGAGATACCGACACAGCCAC
AACCCATCCCACTGCACCACCTGCCCTGCACCACCAAGCCTGGGAGAGCCTCTGTGTCTCACCAGTGCATCTCCAGCTG
GTGGGACTGATCCCTGCTGCCCGTGCACTCCAGTGCCAGCTTTGTTGAAGAGCAGCAGGTCCACTTCACTGGGCAGATTGACTT
TCAGAGGTGCTATTCCCCGTGCACTCCAGTGCAAGCAAGCAGGAGTTTGATTTCCTCTCTTCAGGTGAAGGACAAGACTGGGTTCT
CTCCATCTAGGGCTGGAGAAGCAATTGAACCACCCTGCAGCAACACTCGTCGTGAGGAGCAGAACCTGA
GCTTGGCAGAGCAATTGAACCACCCTGCAGCAACACTCTTGAATCTTGAATCTTGTCGTGAGGAGCAGAACCTGA
GTGCTAATATCACTCATTACTGAATGAAAGTCTATAGGCATTTCTCAAGTGGAAATAGGCTCAACAGCACTACCAAGTA
AAAATGCCTTCTCCTTGTACTCACAAGCAAATTAAGCCTAAGAGATTACCTTACTGAAAATGCAGGTGGAGAGATGACTG
TAACGCTTCTCCTTGTACTCACAAGCAAATTAAGCCTAAGAGATTACCTTACTGAAAATGCAGGTGGAGAGATGACTG
ACAGGGCTTGTTCACCTGCCCTTTCTGCCATGTGCAGATATTTCTCGGTCCTTCTCATTGCTCTGGTTAAGCTAACAGCCCAAATGC
ATAGCCTTTCTGCGTGGTCAGCTGCATGATATTTCTCGGTCATGTCCTTCTCATTGCTCTGGTTAAGCTAACAGCCCAAATGC
AAGTCTCCTAGGCCATTTGTAGCCTAGGGCAACAGCAGGTGGAGAGTGAAAATGTGAGAGAACCTTA
CATTTGGGATCTTTGGGAGCTGCTGCCAGCAGTCCGTGGGAGCAGTTGCTCTGGGGATGATGGATGGA
CCCCGTGGACGGAGCCGTGTGGGAGCAGTGCTTGAAGAGTCTTGAAGAGTGTGCTGTGGGCAGCCCGGATCGGTTGGG
AAGGACGGCATCCCTGGGAGGGACCCCATGGGAGCCAGGACCCGTGAGGAGGGACCGTGAGGAGAGGAGCGGCGGA
GACAAAGTGCCAGGGACTGACCGCAGCCGCCATTCCCTGACTGCTGTAGTGTCAGTCAATTCTATTCTCCCATCCT
TGGGGAAGGTGTTTTCATTTCCTTTCATTCGCAGTCTGAGCCTGAGCAATTCTATTCTGCAGCCGCAATTCATTTGCTGC
TGTGCCAACCCCTGAGCCCTTTCATCGCAGTCTGAGCCTTTCCCGTTTCCCGTTTGAGGAGGGGAGTGGGAGAGGGGCTGTGCTG
GACCCCAGCCCGTGTCTGGGTGAGGGTGAGGCGGGATCTCACACCCCGGGGCCGGAGGCGGAAGCTGCGAGCCGCTGCCTA
TGCCCGCGCTGGGGCCAGGAGGGGCTGAGGATGCGGGCCGGCCCACCCCGGGGCCGGGAGCGCCTTTCGTTTCCAT
TCCCGCCGCGCCGCGGCCTCGTGCCTTTCGTGCCGAGCCGGCCGGTTGGGGGGGCCGGCCGGCCGGCGGAGGCGGCGGCA
GAGCCCAGCC Figure 6
(continued)

>duck RIG-I promoter (-2024 to -1)

AGCTGATGACCTGCAAAAAGTTGGACATGCAAATTTAAAGCTGAGGAACACAACTACACACTATGCTCTGAAAAA
AGAAAAATAACATAATAACAATCAAGAAAAGCATTATTCCCAACCAGTCGGACCACACTCTCTAAGGCAGGACTGG
TGGGTCACACAGGACCCTTCCAGACAGCAGCCACACATGGAAAAGTAACATATTTCCTACACCCTTGCCT
AGAAAGTTCTCCAGAAAACTGCTCAGTAGCACAAGCAGGTTAAGGTCTTCCCAGTGCTGCA
GCTTCTTCACCGATGTGCTTGGCCACTGCAACCCATGCGAACCCAGTACGATGTAGCATAAAACAGCACTGAGGATAT
GAGCATGAGATACCGCACAGGCCACACCATCCACCACTGCCCTGCACCAACAAGCCTGGGAGAGCC
TCCTGTGCTCACCAGTGCATCTCCAGCCTGGTGGGACTGATCCTGTGCCCTCAGTACCCCTCTGCAGCCACCC
TGCCCAGCAGGTGCATCCCACCTCTCGATGCACGATCAGAGGTGTATTCCCCGTGCACTCCAGTGCCAGCTTT
GTTGAAGAGCAGCAGGTCCACTTCACTGAAGGACAAGACTGGGTTTCGCTTGGCAGAGCAATTGCAACCACCTCA
AGTTTGATTTCCTCTTCTTCAGGTGAACACTGTCTGTGAGGAGCAGAACCTGAGTGCTAATATCACTCATTACTGAATG
GCACTGATCTTGAATCTGGAACATTTCAAGTGGAACACTCAACAGGCACTACCAAGTAAAAATGCTTCTCTGTATGT
AAAGCTGTAATAGGCATTTCAAGTGGAACACTCAACAGGCACTACCAAGTAAAAATGCTTCTCTGTATGT
TTGTTACCTGTCAGGCTAATCACCATGCTCTACAGGGTGTGTTGGGCAACTCACGTAGGGCTAACGCTCTTCCTT

→ p1000
GTTACTCACAAGCAATTAAGCCCTAAGAGATTACTTACTGAAATGCAGGGTGGAGAGATGACTGACAGGGGC
TTGTTCACCTGCCTTTTCGCTGCAGAAGATGTCCTCTCAGTTGTTCAGCATTCCCAGTCTAGCAGTGGATAG
CCTTCTGTGTCTTGGTCGTGCATGATGTCCCATCGCTCCTCTCGGTTAGCTAACAGCCCAAAT
GCAAGTCTCTCCTAGCCTAGCCATTGTAGCCTAGGCAACAGCAGCTGGGAGAGAGCAGTGAGAAATGAGA
GAACTTACATTTGGGATCTTTGGGGAGCTGTGCCATGGGAGCCGTGCTGAGCCAGTTGCTCTGGGGA
TGGATGATGAGACCCCGTTGGGAGAGACCCGTGTGTGAGAGTGCTGCCTGTGGGCAGCCCC
GCGGGATCGGTTCGGGAAGGACGGCATCCCTGGGAGGAGCCATGGGAGCCAGGGCAGGAGAGGACCGTG

→ p500
AGGGAGAGGGAGCGGCGGAGACAAAGTGCCAGGACTGCCAGCCATTCCCTGACTGCCTGGGGGG
GAAGAGGTAGAGAGGTGGATGGTGGGAAGGTTGTTTTCATTTCCTTTATTTTCTCACTGTCTAGTCTGTTA
GTGATAGGCAATTAATTCTATTCCCATCCTTGTGCCAAGTCCCTTGTGCCAACCCTTTCCATCGCATTTTCCCGTTCC
                                    → p250        ΔRandom
CTTTGAGGAGGCGGAGTGGAGAGGCGGTGTCTGGACCCCAGGCCGTGTCTCGGTGTCCGGTGAGGCTGTT
     ΔNHLH1                                              ΔSp1/Sp2
GGTGGCGATCCGAGGCTCACGAAGCTGCGAGGCGCGCTATGCCGCTGGCGCCAGAGGCGGGCTGGGAT    → p73
   p125     ΔIRF-1/STAT1:STAT2/IRF-7
GGGGCCGCGATCTCCACACCCCGGGCCGTTTCGTTTTTCATTCGTTTCATTCCCGCCGGCCTGCTGCCTTTCTGTGC

CGAGCCGGTTGGGGGCCGGCGGCCGGCGGCCGGCGGCAGAGCCCAGCC

Figure 7A

RIG-I protein alignment

Figure 7C

```
Anser-anser----    1  MTADEKRSLQCYRRYIERSLNPVYVLGNMADWLPDELRERIRKEEERGVSGAAALELDAV
Anas-platyrhync    1  MTADEKRSLQCYRRYIERSLNPVYVLGNMTDWLPDELRERIRKEEERGVSGAAALFLDAV
Cairina-moschat    1  MTADEKRSLQCYRRYIERSLNPVYVLGNMTDWLPDELRERIRKEEERGVSGAAALFLDAV
Columba-livia--    1  ----------------------------------MKEVRKEEGVTAAALFLDII-----
Picoides-pubesc    1  MTAEKRSLQCYRRYIESINPVYIISNMTDWLSDEVJERKEEFGVTFAAAMFLDVE Anser-anser----   61  LQLEARGWFRGMLDAMLAAGHTGLAEATENWDFSKLEKLEHRQLLKRIEATMLEVDPVV
Anas-platyrhync   61  LQLEARGWFRGMLDAMLAAGYTGLAEATENWDFSKLEKLEHRQLLKRIEATMLEVDPVA
Cairina-moschat   61  LQLEAQGWFRGMLDAMLAAGYTGLAEATENWDFSKLEKLEHRQLLKRIEATMLEVDPVA
Columba-livia--   25  LQLEAFGW-RGFLDAMAAGYTGLAEATENWDFSKLEKLEYRQLLKRIEATMLEVDPVA
Picoides-pubesc   61  DLEERWLRGFIDAMMAAGYTGLAEATENWDFSKLEKLEHRFLLKRIEATMLEVDPYM Anser-anser----  121  LIPYINTCLIDRECEEIQQLSEGRSKAAGITKLIECLCRSDKEHWPKSLQLALDNTGYYR
Anas-platyrhync  121  LIPYINTCLIDRECEEIQQISENRSKAAGITKLIECLCRSDKEHWPKSLQLALDTTGYYR
Cairina-moschat  121  LIPYINTCLIDRECEEIQQLSENRSKAAGITKLIECLCRSDKEHWPKSLQLALDTTGYYR
Columba-livia--   85  LMPYMNSCLIRECEIQISEYRSKAAGITKLIECLCRSDKENWPKSLQLALDNTGYYN
Picoides-pubesc  121  VMPYINTCLIRECEIQISEMRSKAAGITKLIECLCRSDKENWPKSLQLALDNAGYYN Anser-anser----  181  ASELWDIREDNAKDVDSEMTDASEDCLETSMTYSEEAEPDDNLSENLGSAAEGIDKPPPV
Anas-platyrhync  181  ASELWDIREDNAKDVDSEMTDASEDCLEASMTYSEEAEPDDNLSENLGSAAEGIGKPPPV
Cairina-moschat  181  ASELWDIREDNAKDVDSEMTDASEDCLEASMTYSEEAEPDDNLSENLGSAAEGIGKPPPV
Columba-livia--  145  ASELWCIREDKNKDVGEMDASESSFEIRMTFSEEAECDNLSENVSAS--GTYQSSAV
Picoides-pubesc  181  ASELWDFEENFKDFGEMGDASENSFEAMTFSEEMECDNFSENLSASGTNEPPAM
```

Figure 7C (continued)

```
Anser-anser----      241  VEAKKARSYQTELAQPAINGKNALICAPTGSGKTEIAILVCEHHFQNMPAGRKEKVVFLA
Anas-platyrhync      241  VEIKKARSYQTELAQPAINGKNALICAPTGSGKTFVSILICEHHFQNMPAGRKAKVVFLA
Cairina-moschat      241  VEIKKARSYQTELAQPAINGKNALICAPTGSGKTFVSILTCEHHFQNMPAGRKAKVVFLA
Columba-livia---     204  VEFKEARSYQTELAQPAINGKNILICAPTGSGKTFVALICEHHFQNMPTEKAKVVFLA
Picoides-pubesc      240  VEAKEARSYQTELAQPAINGKNILICAPTGSGKTFVALICEHHLQNMPGRKAKIVFLA Anser-anser----      301  TKVPVYEQKNVFKQHFERQGYSIDGMSGENFSNVSVENVIEDNDIVLTPQILVNSFED
Anas-platyrhync      301  TKVPVYEQQKNVFKQHFERQGYSIDGISGENFSNVSVEKVIEDSDIVMPQILVNSFED
Cairina-moschat      301  TKVPVYEQQKNVFKHFERQGYSIHFERQGYSVQGISGENFSNVSVEKVIEDSDIVMPQILVNSFED
Columba-livia---     264  TKVPVYEQQKNVFKQHFERQGYSVQGICGETVANSVEKVQDSDIVLTPQILVNHIKK
Picoides-pubesc      300  TKVPVYEQQNVFKRQHFERQGYSVRGICGETVANIPVENVIEDSLIVLTPQILVNCEKQ Anser-anser----      361  GLTSLSMFTLMIFDECHNTTGNHPYNVLMTRYLEQKFNSPASQLPQILGLTASVGVGNA
Anas-platyrhync      361  GLTSLSIFTLMIFDECHNTTGNHPYNVLMTRYLEQKFNS-ASQLPQILGLTASVGVGNA
Cairina-moschat      361  GLTSLSIFTLMIFDECHNTTGNHPYNVLMTRYLEQKFNSSASQLPQILGLTASVGVGNA
Columba-livia---     324  GLTSLSIFTLMIFDECHNTTGNHPYNVLMTYLEQKFIDSSANQLPQIXGLTASVGVGNA
Picoides-pubesc      360  GITTSLSMFTLMIFDECHNTTGNHPYNVLMTRYLEQKFASSASQLPQIMGLTASVGVGNA Anser-anser----      421  KNIEETEHICSLCSYLDIQAISTVRENIQELQREMNKPEIDVRLVKRRMNEFAVISD
Anas-platyrhync      420  KNIEETEHICSLCSYLDIQAISTVRENIQELQRFMNKPEIDVRLVKRIIHNEAAISN
Cairina-moschat      421  KNIEETEHICSLCSYLDIQAISTVRENIQEJRR-MNKPEIDVRLVKRNEAVISD
Columba-livia---     384  KDITEHICILCSYLDIQHTSTVRENKELQKEMLQNEADISG
Picoides-pubesc      420  RSIKEAEHICILCYLDTQNTSTVRENKELQREGTMPETHVRWKKEAQNRFADIMSG
```

Figure 7C (continued)

| | | |
|---|---|---|
| Anser-anser---- | 481 | LMSETEALMRKTYSVDTSQNSRKDFGTQKYEHW-VVTQRKCRLLQEDKEESRICRAL |
| Anas-platyrhync | 480 | LMSETEALMRKTYSVDTISQNSKKDFGTQNYEHWIVVTQRKCRLLQEDKEESRICRAL |
| Cairina-moschat | 481 | LMSETEALMRKTYSVDTISQNSKKDFGTQNYEHWIVVTQRKCRLLQEDKEESRICRAL |
| Columba-livia-- | 444 | LMSETEAKMRFIYSVDTLDSQNKNDFGTQKYEHWIVITQKFYRLLQIADKEKESSCRDH |
| Picoides-pubesc | 480 | LMSETEALMRKIYSVDTISQNKNDFGTQSYEQMIVITQKKCRLLQPDKEKESMCRDL |

| | | |
|---|---|---|
| Anser-anser---- | 541 | FICTEHLRKYNDALISEDARIIDALSYLTEFFTNVKNGPYTELEQHLTAKFQEKEPLT |
| Anas-platyrhync | 540 | FICTEHLRKYNDALISEDARIIDALSYLTEFFTNVKNGPYTELEQHLTAKFQEKEPLI |
| Cairina-moschat | 541 | FICTEHLRKYNDALISEDARIIDALSYLTEFFTNVKNGPYTELEQHITAKFQEKEPLT |
| Columba-livia-- | 504 | FICTEHLRKFNDALISEDARTFDALPYTTEFFTNVKNGFETEFKQLTAFFQEKEPLT |
| Picoides-pubesc | 540 | FICTEHLRKFNDAMIGEDARIFDAIAYLTEFFTNVRNGPYTQLEKRLTARFQEKEALT |

| | | |
|---|---|---|
| Anser-anser---- | 601 | ALSKDETNENPKLEELACILDDAYCYNPQTRTLLFAKTRALVAALKKCMEENPILSYIKP |
| Anas-platyrhync | 600 | ALSKDETNENPKLEELACILDDAYRYNPQTRTLLFAKTRALVSALKKCMEENPITNYTKP |
| Cairina-moschat | 601 | ALSKDETNENPKLEELACILDDAYRYNPQTRTLLFAKTRALVSALKKCMEENPILSYTKP |
| Columba-livia-- | 564 | ALSKDQSNENPKLFELAILDEAYRYNPQTRTLFEMTRALVAALKKWKANEILSHIKP |
| Picoides-pubesc | 600 | ALSKDETSENPKLEELACILDEAYRYNSDIRTLIFAKTRALVAALKKWEANPILSHMKP |

| | | |
|---|---|---|
| Anser-anser---- | 661 | DVLMGRGRRDQKTGMTLPSQKGVLDAFKTSKDSRLLIATSVADEGIDIQCNLVVLYEYS |
| Anas-platyrhync | 660 | GVLMGRGRRDQTTGMTLPSQKGVLDAFKTSKDIVQCNLVVLYEYS |
| Cairina-moschat | 661 | GVLMGRGRRDQTIGMTLPSQKGVLDAFKTSKDNRLLIATSVADEGIDIVQCNLVVLYEYS |
| Columba-livia-- | 624 | DVLMGHGELHKTGMTLPMKALDAFKTDQSRLLIATSVADEGIDISENLVLYEYP |
| Picoides-pubesc | 660 | GVLMEHGRRDQXTGMILPMQKVLLDAFKTDKDRLLIATSVADEGIDISENLVLYEYF |

Figure 7C (continued)

```
Anser-anser---    721  GNVTKMIQVRGRGRAAGSKCILVTSKTEVENEKCNRYKEEMNKAIEKLQEMDEETFAK
Anas-platyrhync   720  GNVTKMIQVRGRGRAAGSKCILVTSKTEVENEKCNRYKEEMNKAVERIQKMDEETFAK
Cairina-moschat   721  GNVTKMIQVRGRGRAAGSQCILVTSKTEVENEKCNRYKEEMNITAVERIQEMDEKTFAK
Columba-livia--   684  GNITKMIQVRGRGRARDSKCTLVTSAEVENEKINQYKEEMNFEIDNLQNMDETIFAR
Picoides-pubesc   720  GNVTKMIQVRGRGRARNSKCILVTSKTEVENERHNHYKEEMNEAVEQLQNMDEAAFAR Anser-anser---    781  KTHNLQMKEKVLRDSRKKETKPKVVEGQKNLLCGKCKAYACSTDDIRTIKFSHIVLGEA
Anas-platyrhync   780  KTHNLQMKERVLRDSFRKETKPKVVEGQKNLLCGKCKAYACSTDDIRIKFSHIIVLGEA
Cairina-moschat   781  KTHNLQMKERVLRDSRKETKPKVVEGQKNLLCGKCKAYACSTDDIRIKDSHIMLGEA
Columba-livia--   744  KIDELQMKENVLRDSRKKERGAEGKKNLLCGKCKAYACSTDDIRKEIVTMLEIA
Picoides-pubesc   780  KTIMLQMKEKVIRDFKKEHRDINVEGKKNLLCGKCKAYACSTDDIRMKVSHITVLGIA Anser-anser---    841  EKERYITKPHKKPMQFDGFEKKSKMHCRNNCQHDWGITVKYLTFDNLPVIKISFVQS
Anas-platyrhync   840  EKERYITKPHKKPMQFIDGFEKKSKMYCRNNCQHDWGITVKYLTFDNLPVIKSFVES
Cairina-moschat   841  EKERYITKPHKKPMQFEDGFEKKSKMYCRNNCQHDWGITVKYLTFDNLPVIKSFVES
Columba-livia--   804  EKERYMTKPHKKPMCEDCFEKSKMYQADCHHDWGITVKYKIFDNLPVIKSFVED
Picoides-pubesc   840  FKERYMTKPFIKPMKFDEKKSKMICSNCIIHDWGTVKYMDNLPVIKIKSFVKK Anser-anser---    901  AATGTQMDFQKWKSINSSLKNFDVEEMSNLYPPF
Anas-platyrhync   900  TATGTQMDFQKWKSINSSLKNFDVEEMSNLYPPF
Cairina-moschat   901  TATGTQMDFQKWKSINSSLKNFDVEEMSNLYPPF
Columba-livia--   864  VEDRLQMDFQKKLNISMKNEDEEISS
Picoides-pubesc   900  VEGRQMDFQKWK
```

RETINOIC ACID-INDUCIBLE GENE I PROMOTER AND COMPOSITIONS AND METHODS RELATING TO SAME

CROSS-REFERENCE

This application claims priority benefit of U.S. Provisional Patent Application No. 62/564,867, filed Sep. 28, 2017, which application is incorporated herein by reference in its entirety.

INTRODUCTION

Influenza virus H5N1 causes 100% mortality in chickens within hours or days after infection (Barber et al. 2010, *Proc Natl Acad Sci* 107(13), 5913-5918; Kim J, et al., 2009 Influenza and Other Respiratory Diseases 3:121-128) and 60% mortality in humans. Innate immunity is the first line of defense against infectious diseases or tissue damage. A successful innate immune response to influenza infection involves a robust, yet transient induction of interferon-stimulated antiviral genes. Cytoplasmic RNA sensors recognize microbial products in the cytoplasm and trigger the production of INF-β and downstream interferon-stimulated antiviral genes.

Retinoic acid-inducible gene I (RIG-I) has been identified as a cytoplasmic RNA sensor that stimulates a downstream signaling pathway leading to inflammatory cytokine and Type-I IFN release, further inducing the production of antiviral factors. RIG-I is present in ducks but absent in chickens.

A gene edited chicken that exhibits resistance to disease following exposure to RNA viruses, such as highly pathogenic avian influenza H5N1 viruses, would be of great interest, particularly in the commercial setting.

SUMMARY

The present disclosure provides a promoter having at least the core components of a duck retinoic acid-inducible gene I (RIG-I) promoter, as well as expression constructs having the duck RIG-I promoter operably linked to a gene product-encoding nucleic acid (e.g., an avian RIG-I protein), and recombinant host cells containing the duck RIG-I promoter, e.g., in such expression constructs. The present disclosure also provides animals having modified genomes (e.g., gene knockin chickens) expressing a gene construct encoding a duck RIG-I promoter operably linked to a gene product-encoding nucleic acid (e.g., an avian RIG-I protein, such as a duck RIG-I protein).

The present disclosure provides expression constructs comprising an operably linked promoter and a polypeptide-encoding nucleic acid for expression of the polypeptide in a host cell, where the promoter comprises, from 5' to 3', an Sp1/Sp2 transcription factor binding site and an IRF-1/STAT1/STAT2 transcription factor binding site, wherein the Sp1/Sp2 transcription factor binding site comprises the nucleotide sequence CGGCCAGAGGGCGGGC (SEQ ID NO:03) and wherein the IRF-1/STAT1/STAT2 transcription factor binding site is comprised of the nucleotide sequence GGCCGCTTTCGTTTTCCATTC (SEQ ID NO:04). The present disclosure also provides expression constructs wherein the promoter comprises, from 5' to 3', a NHLH1 transcription factor binding site comprising the nucleotide sequence ACGAAGCTGCGA (SEQ ID NO: 05), the Sp1/Sp2 transcription factor binding site comprising the nucleotide sequence CGGCCAGAGGGCGGGC (SEQ ID NO: 06), and the IRF-1/STAT1/STAT2 transcription factor binding site comprising the nucleotide sequence GGCCGCTTTCGTTTTCCATTC (SEQ ID NO:07).

The present disclosure also provides an expression construct containing a polypeptide encoding nucleic acid operably linked to a promoter to provide for expression in a host cell wherein the promoter nucleic acid sequence is of at least 85% sequence identity to the nucleic acid sequence:

```
                                      (SEQ ID NO: 01)
CTGGACCCCAGGCCCGTGTCTCGGTGTCCCGGTGAGGCTGTTGGTGGCGAT

CCGAGGCTCACGAAGCTGCGAGCCGCTGCCTATGCCCGCTGGCGGCCAGAG

GGCGGGCTGCGGATGGGGCCGCGATCTCCACACCCCGCGGGGCCGCTTTC

GTTTTCCATTCCCCGCCGGGCCTCGCTGCCTTTCTGTGCCGAGCCGGTTGG

GGGGCCGGGCCGGGCCGGGCCGGGCGGCGGCCGGCAGAGCCCAGCC
```

In related embodiments, the polypeptide-encoding nucleic acid of the expression constructs disclosed herein encodes a retinoic acid-inducible gene I (RIG-I) protein. The RIG-I-encoding nucleic acid may encode a RIG-I protein having at least 75% sequence identity to a RIG-I protein having the amino acid sequence of:

```
                                      (SEQ ID NO: 11)
MTADEKRSLQCYRRYIERSLNPVYVLGNMTDWLPDELRERIRKEEERGVSG

AAALFLDAVLQLEARGWFRGMLDAMLAAGYTGLAEAIENWDFSKLEKLELH

RQLLKRIEATMLEVDPVALIPYISTCLIDRECEEIQQISENRSKAAGITKL

IECLCRSDKEHWPKSLQLALDTTGYYRASELWDIREDNAKDVDSEMTDASE

DCLEASMTYSEEAEPDDNLSENLGSAAEGIGKPPPVYETKKARSYQIELAQ

PAINGKNALICAPTGSGKTFVSILICEHHFQNMPAGRKAKVVFLATKVPVY

EQQKNVFKHHFERQGYSVQGISGENFSNVSVEKVIEDSDIIVVTPQILVNS

FEDGTLTSLSIFTLMIFDECHNTTGNHPYNVLMTRYLEQKFNSASQLPQIL

GLTASVGVGNAKNIEETIEHICSLCSYLDIQAISTVRENIQELQRFMNKPE

IDVRLVKRRIHNPFAAIISNLMSETEALMRTIYSVDTLSQNSKKDFGTQNY

EHWIVVTQRKCRLLQLEDKEEESRICRALFICTEHLRKYNDALIISEDARI

IDALSYLTEFFTNVKNGPYTELEQHLTAKFQEKEPELIALSKDETNENPKL

EELVCILDDAYRYNPQTRTLLFAKTRALVSALKKCMEENPILNYIKPGVLM

GRGRRDQTTGMTLPSQKGVLDAFKTSKDNRLLIATSVADEGIDIVQCNLVV

LYEYSGNVTKMIQVRGRGRAAGSKCILVTSKTEVVENEKCNRYKEEMMNKA

VEKIQKWDEETFAKKIHNLQMKERVLRDSRRKEIKPKVVEGQKNLLCGKCK

AYACSTDDIRIIKDSHHIVLGEAFKERYTTKPHKKPMQFDGFEKKSKMYCR

NNNCQHDWGITVKYLTFDNLPVIKIKSFVMESTATGTQMDFQKWKSINSSL

KNFDVEEMSNLYPPF.
```

In related embodiments, the promoter of the expression constructs disclosed herein comprises a nucleic acid sequence beginning at the 5' end of the Sp1/Sp2 binding site, having at least 80% sequence identity to the sequence

```
                                              (SEQ ID NO: 08)
CGGCCAGAGGGCGGGCTGCGGATGGGGCCGCGATCTCCACACCCCGCGGGG

GCCGCTTTCGTTTTCCATTCCCCGC¶CGGGCCTCGCTGCCTTTCTGTGCCG

AGCCGGTTGGGGGGCCGGGCCGGCCGGGCCGGGCGGCGGCCGGCAGAGCC

CAGCC.
```

In related embodiments, the promoter of the expression constructs disclosed herein comprise a nucleic acid sequence having at least 80% sequence identity to the sequence of SEQ ID NO:02, or comprise a promoter wherein the promoter begins just 3' of the NHLH1 binding site and comprises a nucleic acid sequence having at least 80% sequence identity to the sequence:

```
                                              (SEQ ID NO: 09)
GCCGCTGCCTATGCCCGCTGGCGGCCAGAGGGCGGGCTGCGGATGGGGCCG

CGATCTCCACACCCCGCGGGGGCCGCTTTCGTTTTCCATTCCCCGCCGGGC

CTCGCTGCCTTTCTGTGCCGAGCCGGTTGGGGGGCCGGGCCGGGCCGGGCC

GGGCGGCGGCCGGCAGAGCCCAGCC.
```

In related embodiments, the expression construct is a viral vector. Additionally, the viral vector may be a retroviral vector, an adenoviral vector or an adeno-associated viral vector.

The present disclosure also provides a recombinant cell comprising any of the expression constructs disclosed herein. The recombinant host cell may be an avian cell such as, for example, a chicken cell.

The present disclosure also provides a transgenic non-human animal, for example a chicken, comprising the genomic integration of any of the expression constructs disclosed herein. Also presently disclosed is a method for producing a chicken resistant to disease caused by avian influenza infection comprised of introducing into a chicken embryo any of the expression constructs disclosed herein.

BRIEF DESCRIPTION OF THE DRAWINGS

FIG. 1A is a schematic diagram for inserting duck RIG-I promoter segment into pGL3 basic vector to construct the full length promoter reporter vector (p2024) expressing firefly luciferase.

FIG. 1B shows the results of dual luciferase analysis of DF-1 cells transfected with a Renilla luciferase vector and either pGL3-Basic (negative control) or p2024. Firefly luciferase activity is normalized to Renilla luciferase activity in the dual luciferase assay. The mean of triplicate determinations (±SD) is shown and significance was analyzed with Student's t-test (*p<0.05).

FIG. 1C shows the results of dual luciferase analysis of DF-1 cells co-transfected pGL3-basic or p2024 with GST only or GST-2CARD as stimulator. RIG-I 2 CARD is the constitutively active N-terminal fragment of RIG-I. Significance was analyzed with multiple T-test (*P<0.05) measured by Dual Luciferase analysis.

FIG. 1D shows the results of dual luciferase analysis of DF-1 cells transfected pGL3-basic or p2024 and treated with or without Poly I: C. Significance was analyzed with multiple T-test (*P<0.05) measured by Dual Luciferase analysis.

FIG. 2A provides a schematic of a series of deletion mutants of duck RIG-I promoter (upper panel) and the results of transfection of each of these deletion mutants into DF-1 cells with Renilla luciferase vector (lower panel). Relative luciferase activities were tested 24 hours post transfection and the mean (±SD) of triplicate determinations for each transfection is shown.

FIG. 2B shows results using the serial deletion mutants of duck RIG-I promoter of FIG. 2A transfected into DF-1 cells with GST or GST-2CARD stimulator. RIG-I 2CARD is a constitutive activator of the MAVS signaling pathway. Relative luciferase activities were tested 24 hours post transfection and it the mean (±SD) of triplicate determinations for each transfection is shown.

FIG. 3A shows the sequence of the RIG-I core promoter showing the transcription factor binding sites in the core promoter of duck RIG-I (SEQ ID NO: 01) as predicted by JASPAR. The grey highlighted regions are the locations of transcription factor binding sites. The position of the nucleotides used in the constructs is shown. The box indicates the random sequence deleted in the control vector.

FIG. 3B. Shows a schematic of the constructs made with indicated deletions of the transcription factor binding sites.

FIG. 3C shows the results of experiments in which DF-1 cells were transfected with wild-type or control with random deletion or p250 with the indicated transcription factor binding sites deleted. Relative luciferase activities were tested 24 hours post transfection and the mean (±SD) of triplicate determinations is shown for each assay. Significance was analyzed with t-test (*P<0.05) FIG. 3D shows the results of experiments in which DF-1 cells were co-transfected with wild type p250 constructs with the control random deletion or transcription factor binding site deleted from p250 or p125 with GST or GST-2CARD as stimulator. Relative luciferase activities were tested 24 hours post transfection and the mean (±SD) for triplicate determinations for each transfection is shown FIG. 3E DF-1 cells were transfected with the wild type p250 promoter, or p250 promoter with TF binding sites deleted or mutated to test the influence of the predicted TF binding sites on the basal promoter activity. Significance was analyzed with Student's t-test. (*p<0.05)

FIG. 4A shows the overexpression of mCherry tagged transcription factors in DF-1 cells. Cells that are visible reflect mCherry fluorescence.

FIG. 4B shows the results of dual luciferase assays to analyze the inducible activity of the duck RIG-I promoter in the indicated DF-1 cells overexpressing the mCherry-tagged transcription factors. Triplicate results are shown for each group. Significance was analyzed with one-way ANOVA. (*P<0.05)

FIG. 4C shows the induction of p125 promoter in the presence or absence of the putative IRF-1 site.

FIGS. 5A-5B provides the results of phylogenetic analysis of RIG-I proteins and promoters.

FIG. 5A is a schematic of a phylogenetic tree of RIG-I promoters was generated by MEGA7 with bootstrap analysis (Tree was generated using the Neighbor-Joining method, 1000 replicates, Maximum Composite Likelihood model). Branches corresponding to partitions reproduced in less than 50% of bootstrap replicates are collapsed.

FIG. 5B is a schematic of a phylogenetic tree of RIG-I proteins generated as above (Neighbor-Joining method, 1000 replicates, Poisson mode).

FIG. 5C shows a phylogenetic tree of all available avian RIG-I sequences and their relationship to duck RIG-I. The evolutionary history was inferred using the Neighbor-Joining method. The bootstrap consensus tree inferred from 1000 replicates is taken to represent the evolutionary history of the taxa analyzed. Branches corresponding to partitions reproduced in less than 50% bootstrap replicates are collapsed. The percentage of replicate trees in which the associated taxa clustered together in the bootstrap test (1000 replicates) are shown next to the branches. The evolutionary distances were computed using the Poisson correction method and are in the units of the number of amino acid substitutions per site. The analysis involved 19 amino acid sequences. All positions containing gaps and missing data were eliminated. There were a total of 719 positions in the final dataset. Evolutionary analyses were conducted in MEGA7.

FIG. 6 depicts the sequence of full-length Duck RIG-I promoter (SEQ ID NO:02).

FIG. 7C. depicts an amino acid sequence alignment of a number of avian RIG-I proteins. *Anser anser* (Greylag Goose, GenBank: ADV58759.1) (SEQ ID NO.:18); *Anas platyrhynchos* (mallard duck, NCBI Reference Sequence: NP_001297309.1)(SEQ ID No.: 11); *Cairina moschata* (GenBank: AGX27431.1) (SEQ ID NO.: 19); *Columba livia* (NCBI Reference Sequence: XP_013225185.1) (SEQ. ID NO. 20); and and *Picoides pubescens* (GenBank: KFV61638.1) (SEQ. ID NO. 21).

DESCRIPTION OF EXAMPLES OF EMBODIMENTS

Figure 1A:
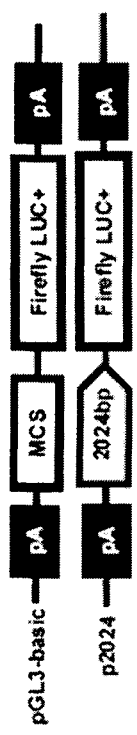
FIGS. 1A-1D depict duck RIG-I promoter activity.

Before the present invention is described further, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Definitions

The terms "retinoic acid-inducible gene I", "RIG-I", "RIG-I protein" and "RIG-I polypeptide" are used interchangeably herein refer to a protein which acts as a cytoplasmic RNA sensor and pattern recognition receptor (PRR) for detecting a variety of RNA viruses (including influenza A virus) and inducing Type I interferon (IFN), inflammatory cytokines and interferon stimulated genes (ISGs).

"RIG-I promoter" as used herein refers to the regulatory DNA region which, in nature, controls expression of a RIG-I gene.

A "duck RIG-I promoter", in the context of the present invention and as used herein, is a nucleic acid compound having a sequence with at least 80%, at least 85%, at least 90%, at least 95%, or at least 99% sequence identity to SEQ ID NO: 01.

The term "promoter" refers to a regulatory DNA region which controls transcription of a operably linked nucleic acid encoding a gene product, and which can be located adjacent to or overlapping a nucleotide or region of nucleotides at which RNA transcription is initiated. A promoter generally contains specific DNA sequences which bind protein factors, often referred to as transcription factors, which facilitate binding of RNA polymerase to the DNA leading to gene transcription.

A "core promoter", usually refers to a promoter which contains the basic elements required to promote transcriptional expression of an operably linked polynucleotide. Eukaryotic basal promoters typically, though not necessarily, contain a TATA-box and/or a CAAT box.

The terms "nucleic acid" and "polynucleotide" are used interchangeably herein.

The terms "protein" and "polypeptide" are used interchangeably herein.

A polynucleotide or polypeptide can be described as having a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the World Wide Web at ncbi.nlm.nih.gov/BLAST. See, e.g., Altschul et al. (1990), J. Mol. Biol. 215:403-10. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-187 (1997). CLUSTAL, MUSCLE, and T-COFFEE are additional examples of alignment programs.

The term "coding sequence" refers to a nucleic acid sequence that once transcribed and translated produces a protein, for example, in vivo, when placed under the control of appropriate regulatory elements. A coding sequence as used herein may have a continuous ORF or might have an ORF interrupted by the presence of introns or non-coding sequences. In this embodiment, the non-coding sequences are spliced out from the pre-mRNA to produce a mature mRNA. A "non-human" animal refers to any animal of a species that is not human.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). Similarly, when an intron is operably-linked to a coding sequence, the intron is spliced out of the mRNA to provide for expression of the coding sequence. In the context of gene conversion, two nucleic acids sequences are operably linked if one sequence can "donate" sequence to the other by gene conversion. If two sequences are unlinked in that one can donate sequence to the other via gene conversion, the donating sequences may be upstream or downstream of the other, and the two sequences may be proximal to each other, i.e., in that there are no other intervening genes. "Unlinked" means that the associated genetic elements are not closely associated with one another and the function of one does not affect the other.

The terms "upstream" and "downstream" are used with reference to the direction of transcription.

The term "intron" refers to a sequence of DNA found in eukaryotic genes that may be transcribed, but are removed from the pre-mRNA transcript before the mRNA is translated into a protein. This process of intron removal occurs by splicing together of nucleic acid (exons) that flank the intron.

As used herein, the term "variant", as in "variant polypeptide" or "variant polynucleotide", encompasses naturally-occurring variants (e.g., homologs and allelic variants) and non-naturally-occurring variants (e.g., muteins). Naturally-occurring variants include homologs, i.e., nucleic acids and polypeptides that differ in nucleotide or amino acid sequence, respectively, from one species to another. Naturally-occurring variants include allelic variants, i.e., nucleic acids and polypeptides that occur in nature and differ in nucleotide or amino acid sequence, respectively, from one individual to another within a species. Non-naturally-occurring variants include nucleic acids and polypeptides that comprise a change in nucleotide or amino acid sequence, respectively, where the change in sequence is artificially introduced and does not occur in nature, e.g., the change is generated in the laboratory or other facility by human intervention ("hand of man").

"Transgenic animal" refers to an animal comprising cells that are genetically modified by the hand of man so as to contain recombinant nucleic acid that is not native to the animal. The foreign nucleic acid may be present in all cells of the animal or in some, but not all, cells of the animal, and may be genomically integrated. The foreign nucleic acid may be referred to as a "transgene". By inserting a transgene into a fertilized oocyte or cells from the early embryo, the resulting transgenic animal may be fully transgenic and able to transmit the foreign nucleic acid stably in its germline. Alternatively, a foreign nucleic acid may be introduced by transferring, e.g., implanting, a recombinant cell or tissue containing the same into an animal to produce a partially transgenic animal. "Transgenic animals", e.g., "transgenic chickens", include "gene edited animals" (e.g., "gene edited chickens"), which have a genome modified by use of a gene editing CRISPR systems, e.g., CRISPR/Cas9. "Gene edited" animals include both "knock in" and "knock out" gene-edited animals, i.e., animals having a genome modified to insert a coding sequence of interest (*"knock in") and animals having a genome modified to disrupt a native coding sequence ("knock out"). Knock in gene-edited chickens, e.g., produced using a CRISPR (e.g., CRISPR/Cas9) gene editing system are of particular interest.

The term "progeny" or "off-spring" refers to any and all future generations derived and descending from a particular animal. Thus, progeny of any successive generation are included herein such that the progeny, the F1, F2, F3, generations and so on are included in this definition.

The term "homozygous" indicates that a eukaryotic cell or animal has two copies of the same gene, with one on each chromosome. In contrast, "heterozygous" indicates that the cell or animal has dissimilar pairs of genes on each of the homologous chromosomes, e.g., one chromosome contains a transgene while the homologous chromosome does not. A transgenic animal may be homozygous or heterozygous for a transgene.

The term "endogenous", with reference to a gene, indicates that the gene is native to a cell, i.e., the gene is present at a particular locus in the genome of a non-modified cell. An endogenous gene may be a wild type gene present at that locus in a wild type cell (as found in nature). An endogenous gene may be a modified endogenous gene if it is present at the same locus in the genome as a wild type gene. An example of such a modified endogenous gene is a gene into which a foreign nucleic acid is inserted. An endogenous gene may be present in the nuclear genome, mitochondrial genome etc.

The term "expression construct" or "expression vector" refers to a recombinant nucleic acid, generally recombinant DNA, that has been generated for the purpose of the expression of a selected nucleotide sequence(s), or is to be used in the construction of other recombinant nucleotide sequences. An expression construct can be present in a vector or in a genome.

A "vector" is a nucleic acid replicon, such as plasmid, phage nucleic acid, viral nucleic acid, or cosmid, to which another nucleic acid segment may be attached so as to bring about the replication of the attached segment in a cell.

The term "recombinant" refers to a polynucleotide, polypeptide, or host cell that has been manipulated by the hand of man, e.g., so as to provide a polynucleotide, polypeptide or host cell that does not occur in nature. A recombinant molecule may contain two or more naturally-occurring sequences that are linked together in a way that does not occur naturally. A recombinant cell contains a recombinant polynucleotide or polypeptide. If a cell is genetically modified to contain a recombinant nucleic acid, the nucleic acid is "exogenous" to the cell.

The term "selectable marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell. Additionally, a florescent protein may be used as a selectable marker, such as GFP or mCherry.

The term "expression", as used herein, refers to the process by which a polypeptide or other gene product is produced based on the nucleic acid sequence of a gene. The process includes both transcription and, if the gene product is a protein, translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

A "host cell" or "target cell" as used herein, denotes an in vivo or in vitro cell, e.g., an avian cell, that can be, or has been, genetically modified, e.g., to contain an expression construct as described herein, and include the progeny of such cells (e.g., when the cell has been genetically modified). It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been manipulated by the hand of man so as to introduce a nucleic acid exogenous to the cell, e.g., an exogenous expression vector.

The term "stem cell" is used herein to refer to a cell (e.g., an avian stem cell) that has the ability both to self-renew and to generate a differentiated cell type (see Morrison et al. (1997) Cell 88:287-298). Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism.

The terms "treatment" "treating" and the like are used herein to refer to any treatment of any disease or condition in a mammal, e.g. particularly a human or a mouse, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

The term "plurality" refers to at least 2, at least 5, at least 10, at least 20, at least 50, at least 100, at least 200, at least 500, at least 1000, at least 2000, at least 5000, or at least 10,000 or at least 50,000 or more. In certain cases, a plurality includes at least 10 to 50. In other embodiments, a plurality may be at least 50 to 1,000.

Duck RIG-I Promoter

The present disclosure provides a promoter having the minimal components of a duck RIG-I promoter, as well as constructs (e.g., expression constructions), recombinant host cells, and transgenic animals (e.g., transgenic avians, e.g., transgenic chickens) containing same.

As illustrated in the examples below, the In one embodiment, the RIG-I promoter comprises, from 5' to 3, an Sp1/Sp2 transcription factor binding site (CGGCCAGAGGGCGGGC (SEQ ID NO:03) and an IRF-1/STAT1/STAT2 transcription factor binding site (GGCCGCTTTCGTTTTCCATTC (SEQ ID NO:04)). In other embodiments, the RIG-I promoter comprises, from 5' to 3, a NHLH1 transcription factor binding site (ACGAAGCTGCGA (SEQ ID NO:05), an Sp1/Sp2 transcription factor binding site (CGGCCAGAGGGCGGGC (SEQ ID NO:06), and an IRF-1/STAT1/STAT2 transcription factor binding site (GGCCGCTTTCGTTTTCCATTC (SEQ ID NO:07)).

The promoter can be at least 160 nucleotides, 175 nucleotides, 180 nucleotides, 185 nucleotides, 190 nucleotides, 200 nucleotides, 225 nucleotides, or 250 nucleotides or more in length. The promoter of the present disclosure provides for Type I interferon (IFN)-inducible expression of an operably linked gene product, e.g., in response to a product of a IFN-stimulated antiviral gene.

The promoter comprises a nucleotide sequence of at least about 160 nucleotides and comprising a sequence at least 80%, at least 85%, at least 90%, at least 95%, at least 99% or 100% identical to the sequence comprising the sequence:

(SEQ ID NO: 08)
CGGCCAGAGGGCGGGCTGCGGATGGGGCCGCGATCTCCACACCCCGCGGGG

GCCGCTTTCGTTTTCCATTCCCCGC¶CGGGCCTCGCTGCCTTTCTGTGCCG

AGCCGGTTGGGGGCCGGGCCGGGCCGGGCCGGGCGGCGGCCGGCAGAGCC

CAGCC, where the underlined nucleotides are the Sp1/Sp2 and an IRF-1/STAT1/STAT2 transcription factor binding sites.

In some embodiments, the promoter comprises a sequence of at least about 180 nucleotides, and comprising a sequence at least 80%, at least 85%, at least 90%, at least 95%, at least 99% or 100% identical to the sequence:

(SEQ ID NO: 09)
GCCGCTGCCTATGCCCGCTGGCGGCCAGAGGGCGGGCTGCGGATGGGGCCG

CGATCTCCACACCCCGCGGGGGCCGCTTTCGTTTTCCATTCCCCGCCGGGC

CTCGCTGCCTTTCTGTGCCGAGCCGGTTGGGGGGCCGGGCCGGGCCGGGCC

GGGCGGCGGCCGGCAGAGCCCAGCC, where the underlined nucleotides are an Sp1/Sp2 transcription factor binding site and an IRF-1/STAT1/STAT2 transcription factor binding site.

In another embodiment, the promoter comprises a sequence of at least about 250 nucleotides, and comprising a sequence at least 80%, at least 85%, at least 90%, at least 95%, at least 99% or 100% identical to the sequence:

(SEQ ID NO: 01)
CTGGACCCCAGGCCCGTGTCTCGGTGTCCCGGTGAGGCTGTTGGTGGCGAT

CCGAGGCTACGAAGCTGCGAGCCGCTGCCTATGCCCGCTGGCGGCCAGAG

GGCGGGCTGCGGATGGGGCCGCGATCTCCACACCCCGCGGGGGCCGCTTTC

GTTTTCCATTCCCCGCCGGGCCTCGCTGCCTTTCTGTGCCGAGCCGGTTGG

GGGGCCGGGCCGGGCCGGGCCGGGCGGCGGCCGGCAGAGCCCAGCC, where the underlined nucleotides are the Sp1/Sp2 transcription factor binding site, an IRF-1/STAT1/STAT2 transcription factor binding site, and an NHLH1 transcription factor binding site.

In another embodiment, the promoter comprises a sequence of at least about 2024 nucleotides comprising at least 80%, at least 85%, at least 90%, at least 95%, at least 99% or 100% identical to the sequence:

(SEQ ID NO: 02)
AGCTGATGACCTGCAAAAAGTTGGACATGCAAAATTTAAAGCTGAGGAACA

CAACTACACACTATGCTCTGAAAAAGAAAAAATAATAATAACAATCAAGAA

AAGCATTTATTCCCACCAGCTGGACCACACTCTCTAAGGCAGGACTTGGTG

GGTCACACAGGGACCCTTCCAGACAGCCACAAGTGATTTTGGGAAAAAGTA

ACATATTTCCTACACCCTTGCCTAGAAAGTTCTCCAGAAAACTGCTCAGCA

CCATGGTTTGCAGTAGCACAAGCAGGTTAAGGTCTTCCCAGTGCTGCAGCT

TCTTCTCACCCGATGTGCTTGGCCACTGCAACCCACCAGTTACGATGTAGC

ATAAAACAGCCACTGAGGATATGAGCATGAGATACCGCACAGGCCACAACC

CATCCCACTGCACCACTGCCCTGCACCAACAAAGCCTGGGAGAGCCTCCTG

TGCTCACCAGGTGCATCTCCAGCCTGGTGGGACTGATCCCTGCTGCCCTCA

GTACCCCTCCTGCAGCCACCCTGCCCAGCAGGTGCATCCCACCTCCTGCAT

GCACGATCAGAGGTGCTATTCCCCCGTGCACTCCAGTGCCAGCTTTGTTGA

AGAGCAGCAGGTCCACTTCACTGGGCAGATTGACTTCTCCATCTAGGGCTG

GAGAAGCAGCAAGCAAGGAGTTTGATTTCCTCCTCTTCTCAGGTGAAGGAC

AAGACTGGGTTTCTGCTTGGCAGAGCAATTGCAACCCACCCTCAGCACTGA

TCTTTGAATCTTCGAACACTCTGTCTGTGAGGAGCAGAACCTGAGTGCTAA

TATCACTCATTACTGAATGAAAGCTGTAATAGGCATTTCTCAAGTGGAAAT

AGGCTCAACAGGCACTACCAAGTAAAAATGCCTCTCTGCTATGTTTGTTAC

CTGTCAGGCTAATCACCATGCTCTACAGGGTGTGTTGGGCAACTCACGTAG

GGGCTAACGCTTCTTCCTTGTTACTCACAAGCAAATTAAGCCCTAAGAGAT

TACCTTACTGAAAATGCAGGGTGGAGAGATGACTGACAGGGGCTTGTTCAC

CTGCCCTTTTCTTGCTGCAGAAGATGTCCTCTCTCAGTTGTTCAGCATTCC

CCAGTCTAGCAGTGGATAGCCTTTCTGTGTCTTGGTCAGCTGTGCATGATA

TTTCTCTGGTCCTTCTCATTGCTCTGGTTAAGCTAACAGCCCAAATGCAAG

TCTCTCCTAGCCTAGGGCCATTTGTAGCCTAGGGCAACAGCAGCTGGGAGA

GAGTGAGAAAATGTGAGAGAACCTTACATTTGGGATCTTTGGGGAGCTGCT

GCCCATGGGGGACCCGTGCTGGAGCAGTTTGCTCCTGGGGGATGGATGGAT

GGACCCCGTGGGACGGAGCCGTGTGGGAGCAGTGCTTGAAGAGCTGCTGCC

TGTGGGCAGCCCCCGCGGGATCGGTTCGGGAAGGACGGCATCCCTGGGAGG

GACCCCATGGGGAGCAGGGGCAGAGAGGGACCGTGAGGGAGAGGGAGCGGC

GGAGACAAAGTGCCAGGGACTGACCGCAGCCCCCATTCCCCTGCACTGCCT

GGGGGGGAAGAGGTAGAGGAGGGTGGATGGTGGGGAAGGTGTTTTTCATTT

-continued
GTTTTCCATTCCCCGCCGGGCCTCGCTGCCTTTCTGTGCCGAGCCGGTTGG

GGGGCCGGGCCGGGCCGGGCCGGGCGGCGGCCGGCAGAGCCCAGCC, where the underlined nucleotides are the Sp1/Sp2 transcription factor binding site, an IRF-1/STAT1/STAT2 transcription factor binding site, and an NHLH1 transcription factor binding site.

-continued
```
CCTTTTATTTTTTCTCACTGCTAGTCTGTTAGTGATAGGCAATTAATTCTA

TTCTCCCCATCCTTGTGCCAACCCCTGAGCCCTTTCCATCGCATTTTCTCC

CCGTTTCCCTTTGAGGAGGCGGAGTGGGAGAGCGGCTGTGCTGGACCCCAG

GCCCGTGTCTCGGTGTCCCGGTGAGGCTGTTGGTGGCGATCCGAGGCTCAC

GAAGCTGCGAGCCGCTGCCTATGCCCGCTGGCGGCCAGAGGGCGGGCTGCG

GATGGGGCCGCGATCTCCACACCCCGCGGGGGCCGCTTTCGTTTTCCATTC

CCCGCCGGGCCTCGCTGCCTTTCTGTGCCGAGCCGGTTGGGGGGCCGGGCC

GGGCCGGGCCGGGCGGCGGCCGGCAGAGCCCAGCC
```

RIG-I Protein

In some embodiments, the RIG-I promoter of the present disclosure is operably linked to a nucleic acid encoding a gene product of interest, e.g., for expression in a host cell. In one embodiment of particular interest, the RIG-I promoter is operably link to a nucleic acid encoding a RIG-I protein. In some embodiments, the duck RIG-I promoter of the present disclosure is operably linked to a nucleic acid encoding a retinoic acid-inducible gene I ("RIG-I") protein. As noted above, the terms "retinoic acid-inducible gene I", "RIG-I", "RIG-I protein" and "RIG-I polypeptide" are used interchangeably herein refer to a protein which acts as a cytoplasmic RNA sensor and pattern recognition receptor (PRRvh) for detecting a variety of RNA viruses (including influenza viruses (e.g., influenza A viruses, such as H5N1 virus), Sendai virus, and flavivirus) and inducing Type I interferon (IFN), inflammatory cytokines and interferon stimulated genes (ISGs). RIG-I typically recognizes short (<4000 nt) 5' triphosphate uncapped double stranded or single stranded RNA. RIG-I is also able to detect non-self 5'-triphosphorylated dsRNA transcribed from AT-rich dsDNA by DNA-dependent RNA polymerase III (Pol III).

The overall structure and function of RIG-I is conserved across phylogeny, despite significant protein sequence divergence. RIGI is composed of N-terminal two caspase activation and recruitment domains ("2CARDs"), a central DExD/H box helicase domain (characterized by the conserved motif Asp-Glu-Ala-Asp (SEQ ID NO:10)), and a C-terminal regulatory domain (CTD). In the absence of RNA trigger, 2CARDs fold back to helicase domain and CTD to form an auto-repressed state. Upon binding of its ligand (short dsRNA or 5'-triphosphate ssRNA) (Hornung et al., (2006) Science, 314(5801), 994-997; Lu et al., 2010, Structure, 18(8), 1032-1043; Luo et al., 2011, Cell, 147(2), 409-422; Yoneyama et al., 2005, J Immunol, 175(5), 2851-2858) to the helicase domain and CTD, RIG-I undergoes extensive rearrangement to expose 2CARDs (Luo et al., 2011, supra). Upon ubiquitination by TRIM25, an E3 ubiquitin ligase, RIG-I is activated and its 2CARDs interact with the CARD domain of the adaptor protein, mitochondria antiviral-signaling protein (MAVS), to stimulate a downstream signaling pathway leading to inflammatory cytokine and Type I IFN release, further inducing the production of interferon stimulated genes (ISG), which are antiviral factors (Gack et al., 2007, Nature, 446(7138), 916-920; Jiang et al., 2011, Nature, 479(7373), 423-427; Kawai et al., 2005, Nat Immunol, 6(10), 981-988; Seth, et al., 2005, Cell, 122(5), 669-682).

Figure 7A:
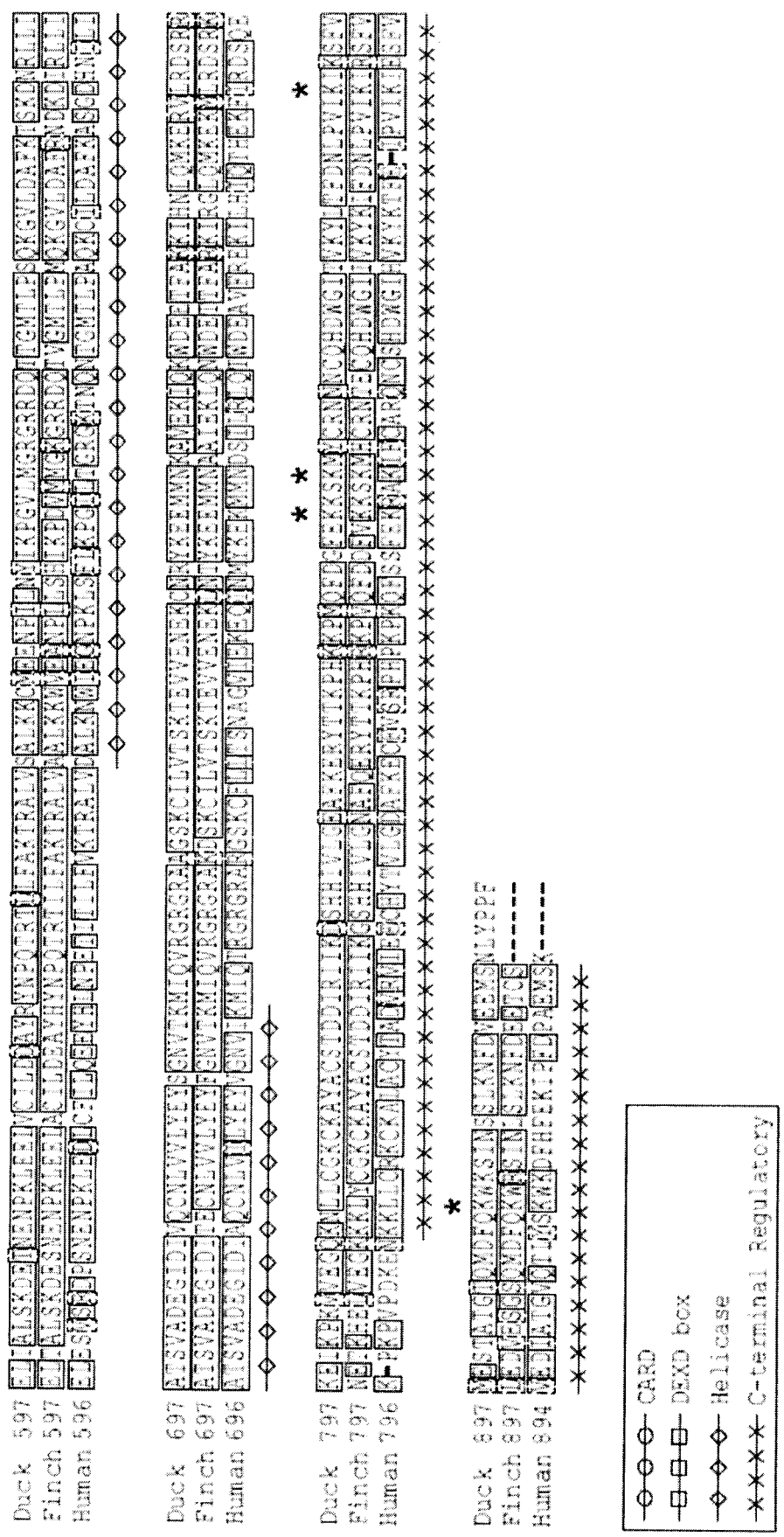
FIG. 7A. depicts an amino acid sequence alignment of mallard duck (accession no. EU363349) (Seq. ID No. 11), zebra finch (accession no. XM_002194524) (SEQ. ID NO. 22), and human RIG-I (accession no. AF038963) (SEQ ID NO. 23) performed using the ClustalW program and edited with Boxshade. Black shading indicates amino acid identity and gray shading indicates similarity (50% threshold). Plus signs indicate human residues involved in polyubiquitination and asterisks indicate residues involved in ligand binding. The ATP binding motif is boxed.
Figure 7B:
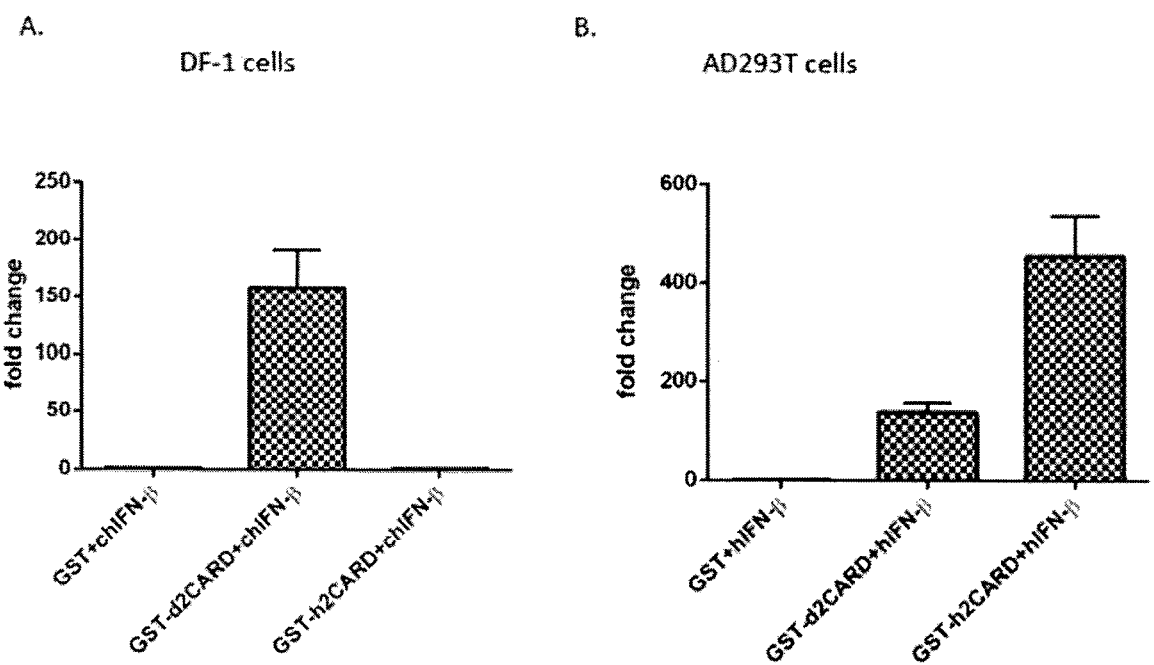
FIG. 7B depicts the results of assays that illustrate that the human RIG-I 2CARD domain is not able to stimulate IFN-β promoter activity in DF-1 cells, however, duck RIG-I 2CARD indeed stimulated IFN-β promoter activity in AD293T cells though its function is much weaker than human RIG-I 2CARD. In Panel A, DF-1 cells were transfected with GST, GST-duck 2CARD (GST-d2CARD) or GST-human 2CARD (GST-h2CARD) individually with chicken IFN-β firefly luciferase reporter vector (chIFN-β) and Renilla luciferase vector (the internal reference control). 24 hours post transfection, the cells were lysed and the chIFN-β activity was measured by dual luciferase assay. GST only is the control. In Panel B, AD293T cells were transfected with GST, GST-d2CARD or GST-h2CARD individually with human IFN-β firefly luciferase reporter vector (hIFN-β) and Renilla luciferase vector (the internal reference control). 24 hours post transfection, the cells were lysed and the hIFN-β reporter activity was measured by dual luciferase assay as above.

FIG. 7A provides an alignment of mallard duck (accession no. EU363349), zebra finch (accession no. XM_002194524), and human RIG-I (accession no. AF038963). Mallard duck RIG-I and zebra finch RIG-I share about 78% amino acid sequence identity. In contrast, human RIG-I, which does not initiate signaling in chicken cells, has only about 54% amino acid sequence identity to mallard duck RIG-I (FIG. 7B). FIG. 7C provides an alignment of avian RIG-I proteins of *Anser anser* (graylag goose; GenBank: ADV58759.1, SEQ ID No. 18); *Anas platyrhynchos* (mallard duck; NCBI Reference Sequence: NP_001297309.1, SEQ ID No. 11); *Cairina moschata* (Muscovy duck; GenBank: AGX27431.1, SEQ ID No. 20); *Columba livia* (Rock dove; NCBI Reference Sequence: XP_013225185.1, SEQ ID No. 21); and *Picoides pubescens* (GenBank: KFV61638.1, SEQ ID No. 22). Guidance for amino acid changes can be provided by, for example, reference to the alignments of FIGS. 7A and 7B. For example, amino acid substitution from the mallard duck RIG-I can be based on substitutions of amino acids in corresponding positions of another avian RIG-I, while avoiding the amino acid substitution to human RIG-I.

In certain embodiments, the RIG-I protein of the expression constructs of the present disclosure is at least 75%, at least 80%, at least 85%, at least 90%, at least 95%, at least 98% or at least 99% identical in amino acid sequence to a RIG-I protein having the amino acid sequence of mallard duck RIG-I (*Anas platyrhynchos*, Genbank accession no. EU363349.1), which amino acid sequence is provided below:

```
                                              (SEQ ID NO: 11)
MTADEKRSLQCYRRYIERSLNPVYVLGNMTDWLPDELRERIRKEEERGVSG
AAALFLDAVLQLEARGWFRGMLDAMLAAGYTGLAEAIENWDFSKLEKLELH
RQLLKRIEATMLEVDPVALIPYISTCLIDRECEEIQQISENRSKAAGITKL
IECLCRSDKEHWPKSLQLALDTTGYYRASELWDIREDNAKDVDSEMTDASE
DCLEASMTYSEEAEPDDNLSENLGSAAEGIGKPPPVYETKKARSYQIELAQ
PAINGKNALICAPTGSGKTFVSILICEHHFQNMPAGRKAKVVFLATKVPVY
EQQKNVFKHHFERQGYSVQGISGENFSNVSVEKVIEDSDIIVVTPQILVNS
FEDGTLTSLSIFTLMIFDECHNTTGNHPYNVLMTRYLEQKFNSASQLPQIL
GLTASVGVGNAKNIEETIEHICSLCSYLDIQAISTVRENIQELQRFMNKPE
IDVRLVKRRIHNPFAAIISNLMSETEALMRTIYSVDTLSQNSKKDFGTQNY
EHWIVVTQRKCRLLQLEDKEEESRICRALFICTEHLRKYNDALIISEDARI
IDALSYLTEFFTNVKNGPYTELEQHLTAKFQEKEPELIALSKDETNENPKL
EELVCILDDAYRYNPQTRTLLFAKTRALVSALKKCMEENPILNYIKPGVLM
GRGRRDQTTGMTLPSQKGVLDAFKTSKDNRLLIATSVADEGIDIVQCNLVV
LYEYSGNVTKMIQVRGRGRAAGSKCILVTSKTEVVENEKCNRYKEEMMNKA
VEKIQKWDEETFAKKIHNLQMKERVLRDSRRKEIKPKVVEGQKNLLCGKCK
AYACSTDDIRIIKDSHHIVLGEAFKERYTTKPHKKPMQFDGFEKKSKMYCR
NNNCQHDWGITVKYLTFDNLPVIKIKSFVMESTATGTQMDFQKWKSINSSL
KNFDVEEMSNLYPPF
```

The RIG-I protein can be an avian RIG-I protein. Avian RIG-I proteins suitable for use in this invention may include, but are not necessarily limited to. duck, (e.g., mallard duck (*Anas platyrhynchos*; NCBI Reference Sequence: NP_001297309.1), Muscovy duck (*Cairina moschata*; GenBank Accession No. AGX27431.1); goose (e.g., swan goose (*Anser cygnoides deomsticus*; GenBank Accession No.

KJ124555), graylag goose (*Anser anser*; GenBank Accession No. ADV58759.1); eagle (e.g., golden eagle (*Aquila chrysaetos canadensis*; GenBank Accession No. KF905228.1), bald eagle (*Haliaeetus leucocephalus*); pigeon, and zebra finch (e.g., NCBI Reference Sequence: XM_002194524), little egret (*Egretta garzetta*; GenBank Accession No. KFP10984.1), Asian Houbara (*Chlamydotic macqueenii*; GenBank Accession No. KFP36728.1); crowned crane (*Balearica regulorum gibbericeps*; GenBank Accession No. KFO06723.1), American crow (*Corvus brachyrhynchos*; GenBank Accession No. KFO059778.1), Golden-collared Manakin (*Manacus vitellinus*; GenBank Accession No. KFW80420.1); rifleman (*Acanthisitta chloris*; GenBank Accession No. KFP82392.1); Northern Carmine Bee-eater (*Merops nubicus*; GenBank Accession No. KFQ30270.1) Anna's Hummingbird (*Calypte anna*; GenBank Accession No. KFP02435.1); Downy woodpecker (*Picoides pubescens*; GenBank Accession No. KFV61638.1); Hoatzin (*Opisthocomus hoazin*; GenBank Accession No. KFR01539.1); Great Creasted Grebe (*Podiceps cristatus*; GenBank Accession No. KFZ58430.1); Red-crested Turaco (*Tauraco erythrolophus*; GenBank Accession No. KFV18917.1); South African ostrich (*Struthio camelus australis*; GenBank Accession No. KFV82733.1); and Rock dove (*Columba livia*; NCBI Reference Sequence: XP_013225185.1).

Vectors, Expression Constructs and Host Cells

The RIG-I promoter of the present disclosure can be provided in a vector, which may provide for replication of nucleic acid of interest (e.g., for recombination production of nucleic acid encoding a RIG-I promoter of the present disclosure, optionally operably linked to a gene product-encoding nucleic acid) and, optionally, for RIG-I-promoted expression of an operably linked gene product-encoding nucleic acid in a host cell). In one embodiment of particular interest, the RIG-I promoter is operably linked to a nucleic acid encoding a RIG-I protein. RIG-I proteins of interest are discussed in more detail below.

A variety of host-expression and/or replication vector systems may be used in connection with the RIG-I promoter of the present disclosure. These include but are not limited to CRISPR/Cas9 systems, replication defective viral vectors, lentiviral vectors, and the Piggyback transposon.

In one embodiment, the recombinant nucleic acid is a recombinant expression vector, such as a plasmid or viral vector. Plasmid and viral vectors useful in creating transgenic chickens are readily known in the art.

In one embodiment, the vector is a bacterial plasmid vector expressing Cas9 and appropriate guide RNA sequences targeting the insertion site under the control of the chicken U6 promoter. This vector can express Cas9 in chicken cells and generate single strand breaks in the target intergenic region.

In one embodiment, the vector is a viral vector, optionally a retroviral, adenoviral or adeno-associated viral vector. Such vectors are able to deliver the recombinant nucleic acid into the cells and the nucleic acids are then stably integrated into the chromosomal DNA of the host.

In an embodiment, the retroviral vector is a replication defective retrovirus vector. The term "replication defective retrovirus vector" as used herein refers to a retrovirus that is capable of insertion of a foreign gene into cells in an initial round of infection but where the vectors would not permit re-infection of the cells after the initial round of infection. For example, a replication defective retrovirus may have the retroviral coding sequences, such as gag, pol and env, replaced by other nucleic acids or deleted, which render the virus unable to replicate. Replication defective virus vectors have been described in Bosselman et al. Mol. Cell. Biol. 7: 1797-1806 (1987); U.S. Pat. No. 5,162,215; Cone and Mulligan, PNAS USA 81:6349-635 (1984); Mann et al. Cell 33:153-159 (1983); Miller and Buttimore, Mal. Cell. Biol. 6:2895-2902 (1986), Watanabe and Temin, Mol. Cell. Biol. 3:2441-249 (1983); Stoker and Bissell, J. Virol. 62; 1008-1015 (1988), U.S. Pat. No. 4,650,764 and Emerman and Temin, Cell, 39:459-467 (1984), all of which are herein incorporated by reference. For example, replication defective retroviral vectors include, without limitation, replication defective retrovirus vectors derived from Moloney murine leukemia virus, Moloney murine sarcoma virus, reticuloendotheliosis virus type A and Avian leukemia virus.

In yet another embodiment, an adenovirus-derived vector is used. The adenovirus vector can be modified such that its ability to replicate in a normal lytic viral life cycle is inactivated. Introduced adenoviral vectors are not integrated into the genome of the host cell but instead remain episomal.

In yet another embodiment, an adeno-associated virus is used. Such viruses can be packaged and can integrate.

Non-viral expression vectors can also be used. For example, a RIG-I promoter and operably linked RIG-I encoding nucleic acid can be entrapped in liposomes for delivery into to cells.

The recombinant expression vectors of the present disclosure may also contain a selectable marker gene which facilitates the selection of host cells transformed or transfected with a recombinant molecule disclosed herein. Examples of selectable marker genes are genes encoding a protein such as G418 and hygromycin which confer resistance to certain drugs, beta-galactosidase, chloramphenicol acetyltransferase, firefly luciferase, and the like. Transcription of the selectable marker gene is monitored by changes in the concentration of the selectable marker protein such as beta-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of the recombinant expression vectors disclosed herein and in particular to determine the effect of a mutation on expression and phenotype. It will be appreciated that selectable markers can be introduced on a separate vector from the nucleic acid of interest.

Host cells for use with the vectors and expression construct of the present disclosure can be selected from any suitable host cell. For example, where the host cell is to be used for replication of a vector of the present disclosure, the host cell can be bacteria, yeast, insect, or any other suitable host cell. Where inducible expression from a RIG-I promoter of the present disclosure is of interest, then the host cell can be a mammalian host cell, e.g., an avian cell, e.g., a chicken cell.

Transgenic Animals

The present disclosure provides non-human transgenic animals that are transgenic for a RIG-I promoter of the present disclosure, which promoter is optionally operably linked to a gene product-encoding nucleic acid of interest, e.g., an avian RIG-I protein. Transgenic non-human animals (e.g., transgenic chickens) in which the transgene contains a RIG-I promoter of the present disclosure operably linked to an avian RIG-I-encoding nucleic acid so as to facilitate an immune response to an RNA virus infection through induction of IFN-stimulated antiviral genes are of particular interest.

In one embodiment, the transgenic animal is a transgenic bird. The term "bird" as used herein refers to any avian species, subspecies or race of organism of the taxonomic Class Ayes, such as, but not limited to, such organisms as chicken, turkey, duck (including mallard duck (*Anas platyrhynchos*), goose, quail, pheasants, parrots, finches, hawks, crows and ratites including ostrich, emu and cassowary. The term includes the various known strains of *Gallus gallus* (chickens), for example, White Leghorn, Brown Leghorn, Barred-Rock, Sussex, New Hampshire, Rhode Island, Australorp, Cornish, Minorca, Amrox, California Gray, Italian Partridge-colored, as well as strains of turkeys, pheasants, quails, duck, ostriches and other poultry commonly bred in commercial quantities.

As used herein, a "genetically modified bird" or "transgenic bird" refers to any bird in which one or more of the cells of the bird contains heterologous nucleic acid introduced by way of human intervention. Accordingly, the term "transgenic chicken" as used herein refers to a chicken that contains a heterologous gene in at least a portion of its cells. Such transgenic chickens can be produced by introduction of a nucleic acid into a cell, directly or indirectly by introduction into a precursor of the cell, by genetic manipulation, including without limitation, sperm-mediated or restriction enzyme mediated integration, microinjection or viral infection. In one embodiment, the recombinant nucleic acid is stably integrated into the genome of the avian, e.g., chicken. In another embodiment, the recombinant nucleic acid is expressed in the germ cells and/or somatic cells of the avian, e.g., chicken. In a related embodiment, the present disclosure provides a recombinant cell or cell line obtained from a transgenic avian (e.g., transgenic chicken) of the present disclosure.

In particular, the present disclosure provides transgenic avians, e.g., transgenic chickens, which are transgenic for a RIG-I promoter of the present disclosure, which RIG-I promoter is operably linked to a gene product-encoding nucleic acid, e.g., a RIG-I protein as described herein, particularly a duck RIG-I protein as described herein. Transgenic avians of the order Galliformes, e.g., a chicken, turkey, grouse, New World quail and Old World quail, ptarmigan, partridge, or pheasant which are transgenic for a RIG-I promoter of the present disclosure, which RIG-I promoter is operably linked to a gene product-encoding nucleic acid, e.g., a RIG-I protein as described herein, particularly a duck RIG-I protein as described herein, which transgenic chickens being of particular interest.

In some embodiments, the transgenic bird is a chicken transgenic for a RIG-I promoter of the present disclosure, operably linked to a nucleic acid encoding a RIG-I protein (e.g., a RIG-I protein having at least 75%, at least 80%, at least 85%, at least 90%, at least 95%, at least 98% or at least 99% identical in amino acid sequence to a RIG-I protein having the amino acid sequence of mallard duck RIG-I (Genbank accession no. EU363349.1)). In such transgenic chickens, the transgene facilitates resistance to disease caused by viral infection, e.g., caused by infection by an RNA virus, e.g., an influenza virus (e.g., an influenza A virus, such as an H5N1 virus) or Newcastle Disease virus. Such transgenic chickens can initiate a successful immune response to RNA virus infection by recognizing RNA virus infection and inducing IFN-stimulated antiviral genes.

Accordingly, the present disclosure also provides a method for conferring resistance to a disease in a bird (e.g., chicken) caused by an RNA virus, where the method comprises genetically modifying the genome of a chicken so as to be transgenic for a RIG-I promoter-avian RIG-I protein-encoding expression construct of the present disclosure. The present disclosure also provide a method for reducing RNA virus replication in a chicken, where the method comprises genetically modifying the genome of a chicken so as to be transgenic for a RIG-I promoter-avian RIG-I protein-encoding expression construct of the present disclosure.

Chickens having genetically modified genomes have been generated in a variety of ways. The production of transgenic chickens through various strategies including lentiviral and viral vectors, transposons, transcription activator effector nuclease (TALEN), and zinc-finger nucleases (ZFN) has recently been thoroughly reviewed (Doran et al., 2016, *Transgenic Res* 25, 307-319). The TALEN approach has recently been successful to generate gene knockouts in chickens (Park et al., 2014, *Proc Natl Acad Sci USA* 111, 12716-12721). Gene editing of chicken genomes can be achieved using a CRISPR system, such as CRISPR/Cas9, which provides for versatility and efficiency (see, e.g., Hsu et al., 2014, *Cell* 157, 1262-1278). CRISPR/Cas9 can be used efficiently to modify chicken embryonic DF-1 cells and make alterations in somatic (Abu-Bonsrah et al., 2016. *Sci Rep* 6, 3452) and embryonic germ cells in the chicken embryo (Dimitrov et al., 2016, *PloS One* 11, e0154303). Repair through homologous recombination has been used to insert genes into primordial germ cells of chickens (knock-ins) and clonal lines of PGCs can be used to generate gene knockin birds (Dimitrov et al., 2016, *infra*). Examples of methods of generating genetically modified birds, including genetically modified chickens, have been described, for example, in U.S. Pat. No. 5,162,215 (Bosselman et al.), US 2002/0108132 (Rapp), US 2009/0158449 (Nakaishi et al.), Tyack et. al, Transgenic Res. 2013 Jun. 17; 22:1257-1264; and Doran et. al, Transgenic Res. 2013 Jun. 25(3):307-19, and in U.S. Pat. Nos. 7,375,258, 7,323,619, 7,312,374, 7,375,258, 7,507,873, 7,550,650, 8,507,749, and 9,510,571, which are hereby incorporated by reference in their entirety.

For example, transgenic chickens may be produced by using a retrovirus vector, embryonic stem cells, primordial germ cells or spermatozoa. Methods of producing the transgenic chickens having a RIG-I promoter/RIG-I protein-encoding expression construct include, without limitation, introducing the transgene to the chicken using, a viral or a non-viral vector; sperm-mediated gene transfer; restriction enzyme-mediated integration; nuclear transfer; ovum transfer and the like. Transgenic chickens produced by the present methods will be able to lay eggs and/or produce offspring containing the RIG-I heterologous protein.

For example, Bosselman et al. (U.S. Pat. No. 5,162,215) describe introduction of a replication defective retroviral vector into pluripotent stem cells of a chick embryo. Briefly, an opening, for example an opening about 5 mm in diameter, is made in a laid chicken egg which is not more than two days old. Typically the opening in the laid chicken egg is made using a drilling tool with an abrasive rotating tip to drill a hole in the eggshell but maintaining the underlying shell membrane intact. The membrane is cut out by a scalpel to expose the embryo which can be visualized with an optical dissecting microscope having 6×-50× magnification. The solution comprising the DNA or vector can be any suitable medium, such as tissue culture medium, which is then microinjected into an area beneath and around the blastoderm. Typically 5-20 µl of solution is microinjected.

Microinjection is carried out using a micromanipulator and a very small diameter needle, optionally a glass needle with 40 to 60 µm outer diameter. The egg is then sealed with shell membrane and a sealing material, such as glue, cement or paraffin. The sealed microinjected egg is incubated at 37 degree C. to allow development of the embryo until the egg hatches. The hatched chickens are then genotyped, for example, by analysis of blood DNA and positive chickens are bred to produce progeny transgenic chickens.

Accordingly, in one embodiment, the present disclosure provides a method of producing a transgenic chicken with increased resistance to RNA virus infection, comprising: inserting into a chicken embryo a recombinant nucleic acid molecule comprising a RIG-I promoter/RIG-I protein-encoding expression construct of the present disclosure; and incubating the egg so as to allow the embryo to hatch.

Alternatively, the DNA or vector comprising the DNA may be injected into chicken embryonic stem cells or primordial germ cells, which are then injected into recipient embryos. See for example, US 2003/0115622 to Ponce de Leon et al., US 2006/0075513 to Ivarie et al. and US 2006/0206952 to Van de Lavoir and Leighton, all of which are incorporated herein by reference. Briefly, Ponce de Leon et al. describe excising blastodermal cells containing presumptive primordial germ cells (PGCs) from donor eggs, typically at stage XII to XIV. The PGCs are cultured in suitable culture medium containing factors to promote proliferation, such as LIF, bFGF, SCF and IGF to produce embryonic germ cells, which are typically produced after 28 days of culture. The cultured PGCs are introduced with a transgene by any suitable means, such as lipofection, transfection, microinjection, transformation, etc. The transgenic PGCs are then introduced into the dorsal aorta of recipient embryos, typically around stage 13-14. Similar to the above protocol from Bosselman et al., a small opening in shell is made, typically with forceps, and the PGCs are injected using a micropipette. Typically 200 donor PGCs are injected. After injection, the opening is sealed as described herein. The transfected donor cells become incorporated into the recipient embryos, some of which will produce chickens with the transgene in the germline.

Alternatively, WO87/05325 to Rottman and Hofer describe transferring material into sperm or egg cells by using liposomes containing the recombinant DNA or vector. The transgenic donor egg can then be transferred to the oviduct of a recipient hen (see Tanaka et al. 1994, J. Reprod. And Fertility, 100:447-449, incorporated herein by reference) or male germ cells can be transferred to a recipient testis. Restriction enzyme mediated integration is an alternative method for creating transgenic sperm (see Shemesh et al. in WO 99/42569, incorporated herein by reference).

Accordingly, in another embodiment, the present disclosure provides a method of producing a transgenic chicken with increased resistance to RNA virus infection, comprising: inserting into a chicken germline or embryonic stem cell a vector comprising a RIG-I promoter/RIG-I protein-encoding expression construct of the present disclosure to produce a genetically modified chicken; incubating the genetically modified chicken germline or embryonic stem cell; culturing the genetically modified chicken germline or embryonic stem cell so as to produce a zygote, and incubating the zygote to form an embryo, and incubating the embryo to allow the embryo to hatch.

It should be noted that the term "germline cell" as used herein refers to a germ cell, such as a primordial germ cell, or sex cell, such as sperm or egg, that have DNA that is passed on to offspring. The term "zygote" as used herein refers to the cell resulting from the union of sperm and egg. The phrase "producing a zygote from a germline or embryonic stem cell" as used herein includes, without limitation, fertilization of a non-transgenic egg with a transgenic sperm cell or fertilization of a transgenic egg with a non-transgenic sperm cell or microinjection of a transgenic germline cell or embryonic stem cell or culture of cells into a non-transgenic zygote or ovum or sperm transfer. The term "embryo" as used herein refers to the product of the zygote inside the avian (e.g., chicken) egg.

EXAMPLES

The following examples are provided in order to demonstrate and further illustrate certain embodiments and aspects of the present invention and are not to be construed as limiting the scope thereof.

Methods and Materials

Identification and Cloning of Duck RIG-I Promoter TOPO Vector

The sequence of duck RIG-I has been previously described (Barber et al., Proc. Natl. Acad. Sci. USA 2010 107(3): 5913-18) and a sequence of a duck genome described (see, 2013 Nat. Genet. 2013 45(7): 776-83). However, the transcription start site (TSS) and promoter region of duck RIG-I could not be identified in the genome sequence.

Using a forward primer based on the genome sequence (5'-CCAAGTAAAAATGCCTCTCTGCT-3' SEQ ID NO:12) and a reverse primer in exon 2 (5'-GCATCGCGTCCAGCATCCCTCGGA-3' SEQ ID NO:13), a 1 kb PCR fragment as amplified from blood genomic DNA. Sequencing of this product identified exon 1 and sequences approximately 2 kb upstream. A forward primer was designed further upstream based on genome sequence (5'-AGCTGATGACCTGCAAAAAGTT-3 SEQ ID NO:14) and a reverse primer within exon 1 (5'-GTTGAGGCTCCGCTCGATGTA-3' SEQ ID NO:15) resulting in the amplification of approximately 2 kb upstream from the first exon of duck RIG-I (from −2024 to +63) using duck genomic DNA as template and the KAPA Hi Fi™ PCR Kit (Kapa Biosystems). The product was cloned into PCR2.1 TOPO vector (Invitrogen) to sequence as per the manufacture's protocol.

Finally, taking the 2 kb fragment in TOPO vector as template, the full length of duck RIG-I promoter (−2024 to −1) was amplified using the Q5 High-Fidelity PCR Kit (NEB) and primers 5'-AGCTGATGACCTGCAAAAAGTT-3' (SEQ ID NO:16) and 5'-GGCTGGGCTCTGCCGGCCG-3' (SEQ ID NO:17), then ligated it into PCR 2.1 TOPO vector with T4 DNA ligase (NEB) as the manufacture's instruction.

Construction of Wild Type and Mutant Duck RIG-I Promoter Reporter Plasmids

The full-length duck RIG-I promoter sequence was digested out of PCR2.1 TOPO vector by KpnI and XhoI (NEB) at 37° C. for 30 minutes, followed by electrophoresis and gel extraction. The extracted product was ligated to pGL3-basic luciferase reporter vector (Promega; Madison, Wis.), to generate p2024 vector as illustrated in FIG. 1A. This construct was then used as the backbone plasmid in all duck RIG-I promoter constructs discussed below A series of deletion mutants and specific transcription factor binding site deletion mutants of duck RIG-I promoter were generated using a site-directed mutagenesis protocol (NEB; Ipswich, Mass.). In brief, p2024 was used to synthesize the additional truncation constructs, p1000, p500, p250, p125, p73 using primers based on the sequence. The specific truncated promoter construct (p250 and p125) was used as the template to synthesize the transcription binding site deletion mutants using Phusion High-Fidelity PCR kit (NEB; Ipswich, Mass.). The extracted products were treated with Dpn I (NEB; Ipswich, Mass.) to eliminate the original template plasmid. The treated products were further purified with the QIAquick™ PCR purification kit (QIAGEN; Mississauga, ON) and the two ends of amplified mutant strands were ligated together with T4 DNA ligase following addition of 5'-phosphates with T4 Polynucleotide Kinase (NEB) to form the mutant constructs.

Cell Culture and Transfection

DF-1 cells are spontaneously immortalized chicken embryo fibroblast cells, derived from East Lansing Line (ELL-0) chicken embryos previously described in Schaefer-Klein (Virology 1998 248(2): 305-11) and were purchased from ATCC (ATCC® CRL-12203™). They were maintained in Dulbecco's Modified Eagle Medium (DMEM) with 10% Fetal Bovine Serum (FBS) in a 5% CO2 incubator at 39° C.

DF-1 cells were seeded into 24-well plates at 2×105/well. 24 h later, the cells were transfected with the indicated DNA constructs using LIPOFECTAMINE 2000™ reagent (Invitrogen) at a ratio of 1:2.5 (DNA:Lipofectamine). 24 h post transfection, the cells were lysed for the dual luciferase assay. The indicated RIG-I promoter vectors, the Renilla control vector and the RIG-I 2CARD construct were transfected at 150 ng/well, 10 ng/well and 20 ng/well, respectively.

Dual Luciferase Assay

DF-1 cells in a 24-well plate were transfected with the indicated duck RIG-I promoter plasmid and the Renilla luciferase control vector with or without the stimulators (20 ng/well). The constitutively active duck RIG-I N-terminal domain (2CARD) or 2 µg/ml high molecular weight (BMW) polyinosinic-polycytidylic acid, poly (I:C)) were used to activate the MAVS signaling pathway. The promoter activity of duck RIG-I was measured using the Dual Luciferase Reporter Assay System (Promega) 24 h post transfection according to manufacturer's instructions. Briefly, the cells were lysed with 100 µl 1× passive lysis buffer at room temperature for 15 min. 20 µl cell lysate was transferred to 1.5 ml Eppendorf tube, followed by measuring the luciferase activity using the GloMax 20/20 Luminometer (Promega) after adding 100 ul luciferase assay reagent II and 20 µl 1× stop and glo reagent into cell lysate, in sequence. The firefly luminescence from the test reporters was normalized to the Renilla luminescence from the control vector and the normalized relative luciferase units (RLU) were further divided by the mean RLU of the control group. For each group, the experiment was done in triplicate. Assays were performed at least twice.

Statistical Analysis

Values indicated the means±standard deviation and the statistical analysis among multiple experimental groups was performed by Tukey test under one-way analysis of variance (ANOVA) using GraphPad Prism 6 software. $P<0.05$ was considered significant.

Example 1: Cloning and Sequencing the Duck RIG-I Promoter Region

To recover the RIG-I promoter sequence, which was lacking exon 1 in the duck genome sequence, two fragments upstream of RIG-I were amplified. The first 1 kb fragment spanned from upstream to exon 2 of RIG-I and contained part of the promoter sequence, the complete 5'UTR, exon 1 and intron 1 and a part of exon 2. Using a forward primer based on a region further upstream of RIG-I in the annotated duck genome sequence and a reverse primer within exon 1 of the amplified sequence, approximately 2 kb of the RIG-I promoter sequence was amplified and sequenced. The sequence of this approximately 2 kb of the RIG-I promoter is provided in FIG. 6 (SEQ ID NO: 02). The promoter sequence was confirmed to be identical in the overlap between both independent amplified regions.

Example 3: the Duck Promoter is Interferon Inducible

Figure 1B:
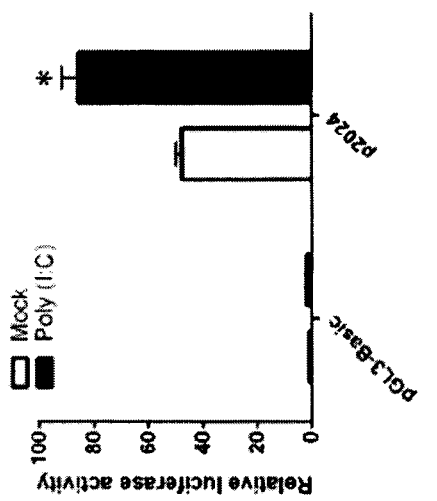

To determine whether the amplified 2024 bp sequence (SEQ ID NO:02) upstream of the duck RIG-I gene has promoter activity, this segment was inserted into the multiple cloning site (MCS) in the pGL3-basic vector to generate a promoter reporter vector, p2024 (FIG. 1A). P2024 was transfected into DF-1 cells to test its promoter activity using the dual luciferase assay. The empty pGL3-basic vector was transfected as negative control. The inserted 2024 bp promoter sequence significantly increased the relative luciferase activity by 17 times compared to the empty pGL3-basic vector (FIG. 1B), indicating that the inserted segment has promoter activity.

It has been previously shown that duck RIG-I is significantly upregulated during an innate immune response by Barber et al. (Proc. Natl. Acad. Sci. USA 2010 107(3): 5913-18). The activation of RIG-I or MDA-5 induces type-I IFN production and both RIG-I and MDA5 are ISGs and also regulated by type-I IFN in a positive feedback loop (Kang et al., Oncogene 2004 23(9): 1789-1800; Kang et al, Proc. Natl. Acad. Sci. 2002 99(2): 637-42; Su et al., J. Cell Physiol. 2007 213(2): 502-10). It was also previously shown that overexpression of the constitutively active N-terminal region of duck RIG-I, the two CARD domains (2CARD), can stimulate the MAVS signaling pathway and induce type-I IFN and ISG upregulation in chicken DF-1 cells (Miranzo-.Navarro, D. and K. E. Magor, 2014. Activation of Duck RIG-I by TRIM25 is Independent of Anchored Ubiquitin. PLoS One 9: e86968.

Figure 1C:
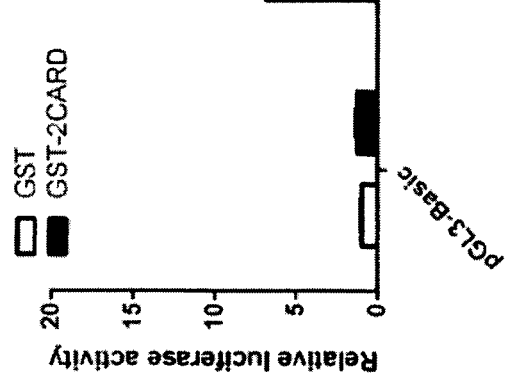
Figure 1D:
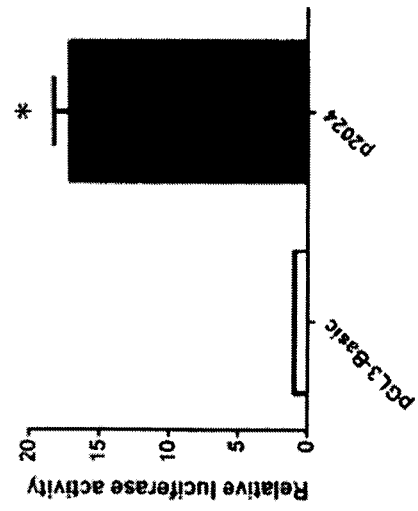

In view of this, in order to determine whether the promoter activity of duck RIG-I is inducible by type-I IFN, RIG-I promoter vector (p2024) was co-transfected with or without duck RIG-I 2CARD. The relative activity of the RIG-I promoter upon stimulation for 24 hours following transfection with RIG-I 2CARD was approximately two fold higher than the p2014 promoter alone (FIG. 1C). Though chickens lack the RIG-I gene, they have MDA-5, which can be effectively activated by longer RNA molecules (>2 kb) such as HMW poly (I:C) (Kato et al., J. Exp Med. 2008 205(7): 1601-10) Chicken MDA5 can compensate, at least partially, for the lack of RIG-I (Liniger et al., 2012, J Virol. 2012 January; 86(2):705-17 and Karpala et al., 2011, J Immunol. 2011 May 1, 2011; 186(9):5397-405). The relative luciferase activity of duck RIG-I promoter co-transfected with poly (I:C) was also approximately two-fold higher than the p2024 RIG-I promoter alone, thus significantly induced (FIG. 1D). The firefly luciferase activities remain unchanged for the pGL-3 basic control, either stimulated or unstimulated by co-transfection with 2CARD or poly (I:C), (FIG. 1D). Chicken cells sense influenza A virus infection through MDA5 and CARDIF signaling involving LGP2.

Example 4: the Core Promoter of Duck RIG-I is Interferon-Inducible

Figure 2A:
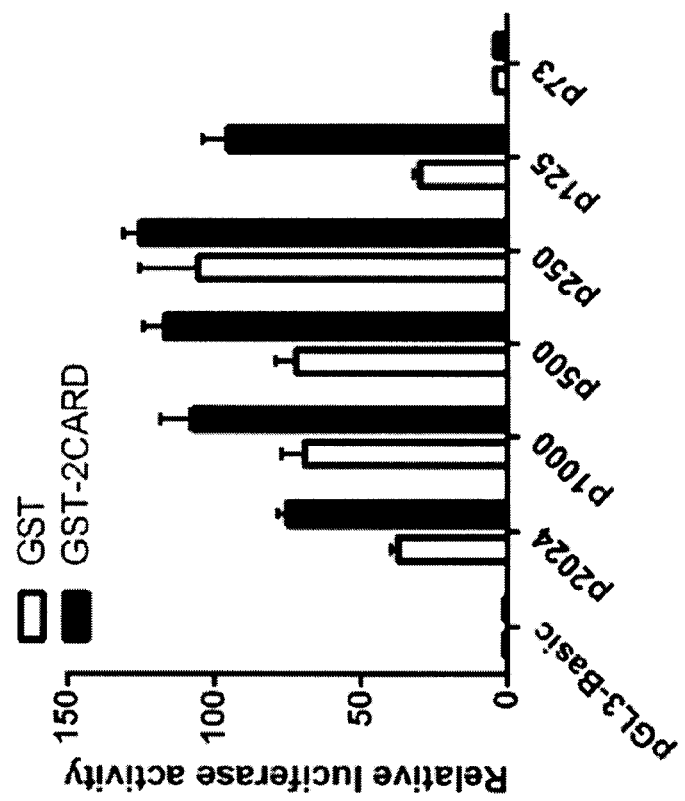
FIGS. 2A-2B provide evidence that the core promoter of duck RIG-I is 250 bp upstream of TSS.
Figure 2B:
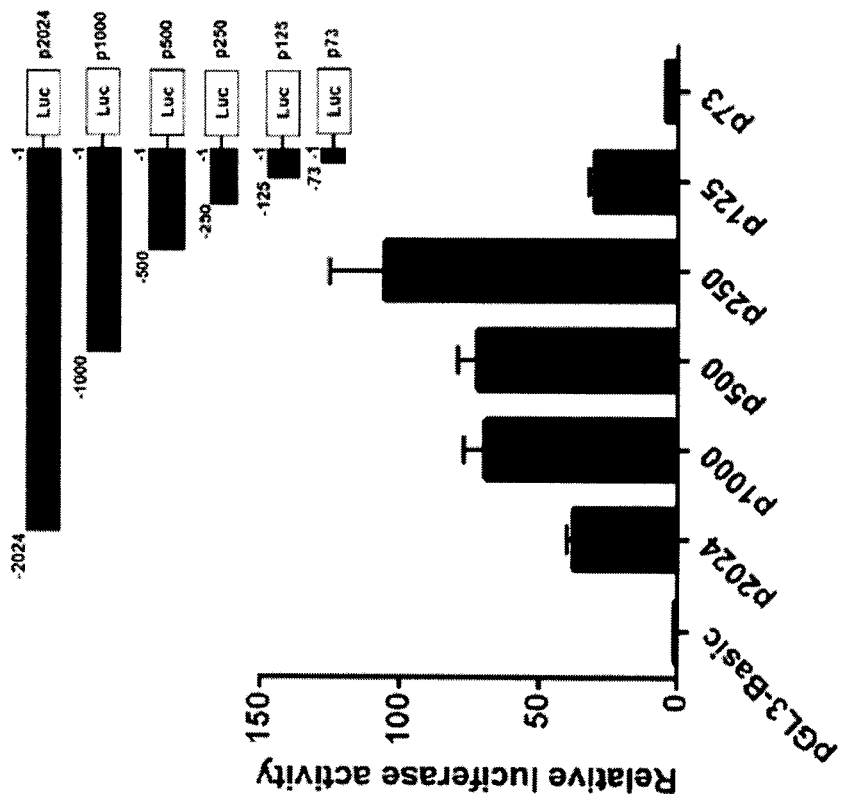

In order to identify the core promoter and the essential elements for duck RIG-I inducible activity, a series of deletion mutants of the duck RIG-I promoter were constructed (FIG. 2A) and transfected into DF-1 cells. At 24 hours post transfection, the relative promoter activity was tested by dual luciferase assay. Compared with the full-length promoter p2024 and deletion mutants, p250 had the highest basal promoter activity, whereas p73, the most proximal region to the transcription start site (TSS), had the lowest activity (FIG. 2B). This indicated that p250 contained the core promoter of duck RIG-I. One or more suppressive elements may be located between −250 bp and −2024 bp, because several longer fragments had lower activity than the p250 fragment. All promoter constructs were inducible by RIG-I 2CARD except p73 (FIG. 2C). Construct p125 had the highest inducible activity following transfection of RIG-I 2CARD in DF-1 cells (FIG. 2C). This result demonstrates that the core promoter region contains all the necessary elements for the interferon inducible expression of duck RIG-I expression. The sequence of the core promoter region (SEQ ID NO:01) is provided in FIG. 3A.

Example 5: Identification of Putative Transcription Factor Binding Sites

Figure 3A:
FIGS. 3A-3E depict the sequence and a schematic of the duck RIG-I core promoter and the results of experiments showing that deletion of the Sp1/Sp2 binding site largely decreased the basal RIG-I promoter activity, whereas, deletion of the IRF-1/STAT1/STAT2 binding site undermined RIG-I promoter interferon inducible activity.

To identify transcription factor (TF) binding sites in the core promoter sequence, the proximal promoter sequence was examined with the TF search program, "JASPAR". Two transcription factor binding sites (Sp1 and Sp2) were predicted to bind between −125 bp and −250 bp, and (Sp1 and Sp2) bind the same position in this region. Additionally, three TFs (IRF1, STAT1 and STAT2) were predicted to bind the same position between −125 bp and −73 bp. There were no predicted TF binding sites in the −73 bp region (FIG. 3A). To confirm the importance of these binding sites to the basal and inducible expression of duck RIG-I, promoter deletion mutants with the Sp1/Sp2 or IRF1/STAT1/STAT2 binding sites deleted, and a control construct deleting a random sequence were constructed from the p250 promoter construct. Additionally, promoter mutation constructs were generated by mutating the SP1/SP2 transcription factor binding site comprising the nucleotide sequence: GAGGGCGGGC (SEQ ID NO: 24) to GAGTTCTTGC (SEQ ID NO: 25). Additionally we generated a mutated IRF-1 site, GCTTTCGTTTTCCA (SEQ ID NO: 26) to GCTAACGTGAGCCA (SEQ ID NO: 27).

Figure 3B:
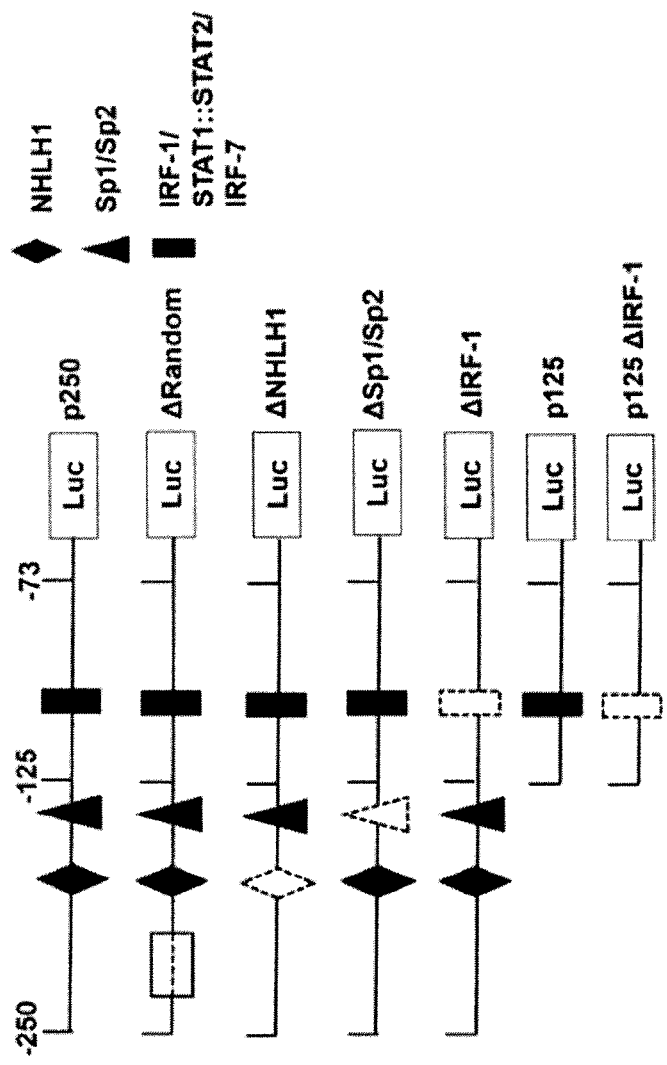
Figure 3C:
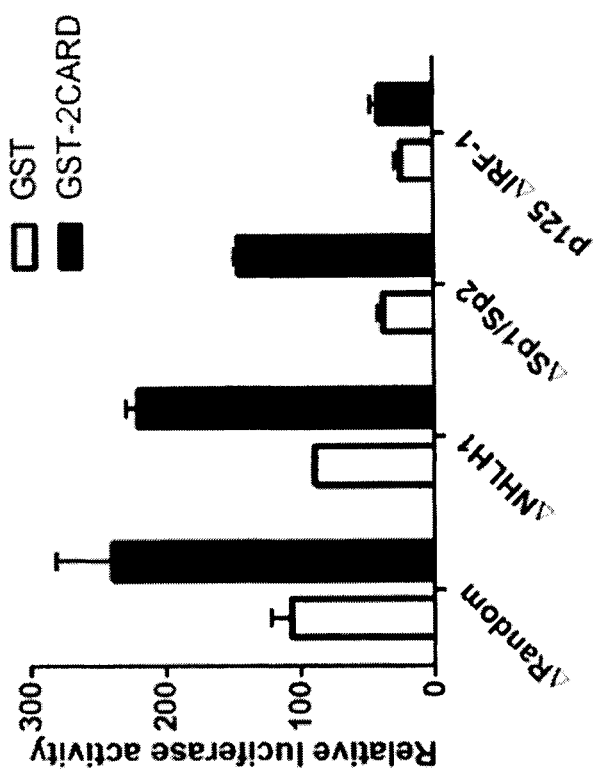
Figure 3D:
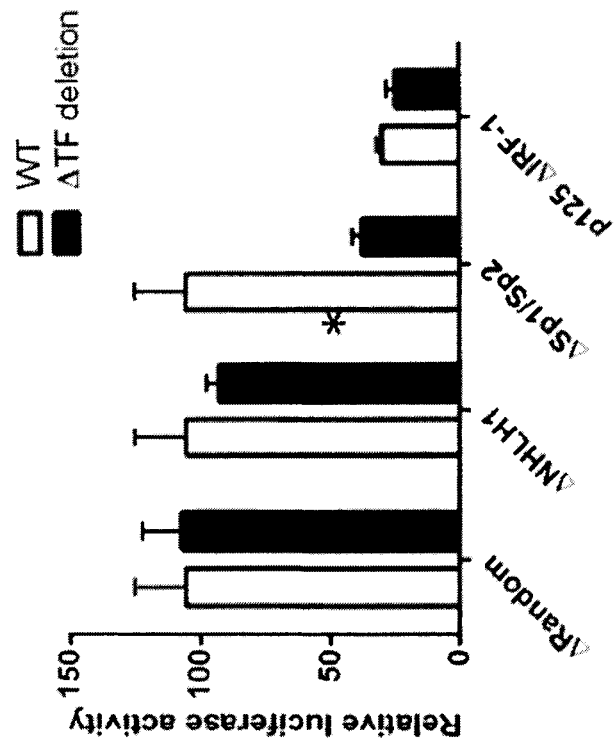
Figure 3F:
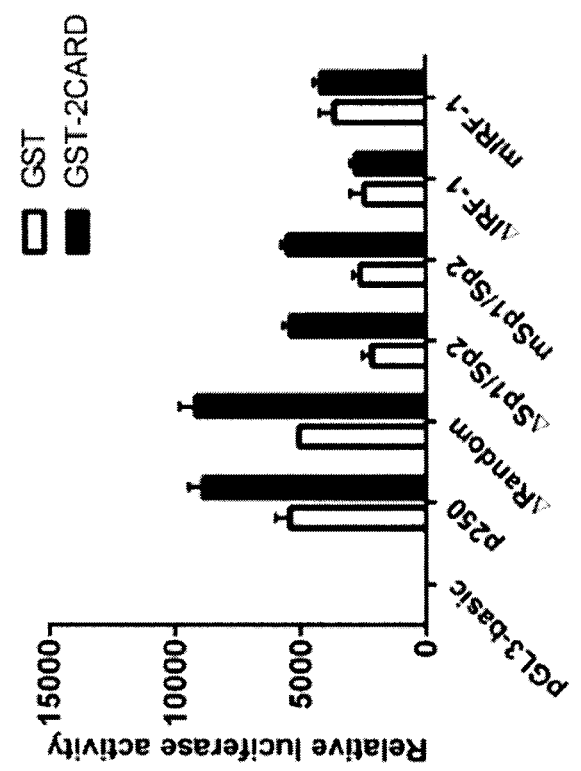
FIG. 3F DF-1 cells were co-transfected with the indicated wild type p250 promoter or p250 promoter with TF binding sites deleted or mutated with or without GST-2CARD (stimulator) to assess which predicted TF binding sites affect the inducible promoter activity. For all experiments, firefly luciferase activities were normalized to Renilla activity at 24 h post transfection. The mean of triplicate determinations (±SD) of relative luciferase activity is shown and each experiment was repeated at least twice.
Figure 3E:
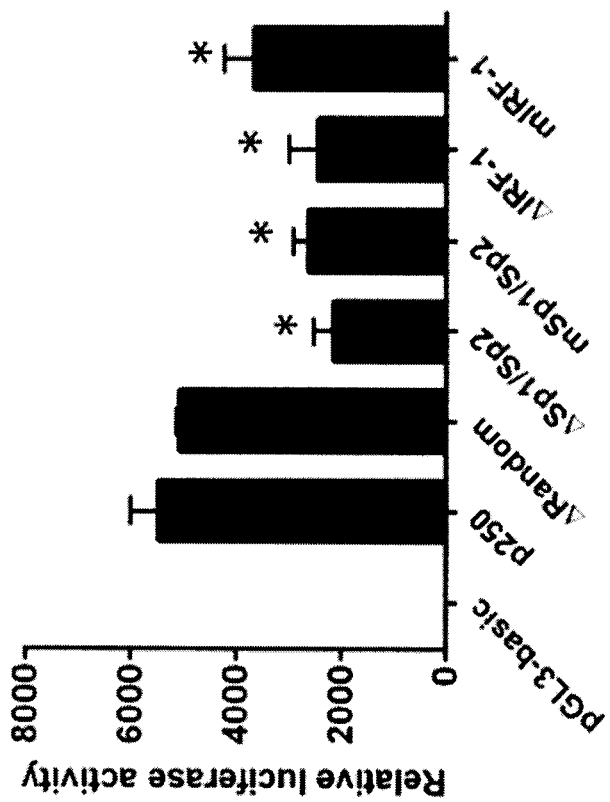

The mutant or wild-type promoter constructs were transfected into DF-1 cells, alone or co-transfected with duck RIG-I 2CARD. At 24 h post transfection the relative promoter activities were determined by dual luciferase assay. Compared to the wild type promoter vectors (p250 or p125), the deletion of the Sp1/Sp2 binding site significantly decreased the basal promoter activity (FIG. 3B). The deletion of the IRF1/STAT1/STAT2 binding site resulted in the loss of the inducible activity. Because all deletion mutants of p250 still bear IRF1/STAT1/STAT2 binding site, their promoter activities could be induced by RIG-I 2CARD (FIG. 3C). The comparison of wild-type and deletion and mutation constructs of predicted Sp1/Sp2 binding site and the IRF1/STAT1/STAT2 support that these binding sites contribute to duck RIG-I basal and inducible expression, respectively.

Figure 4A:
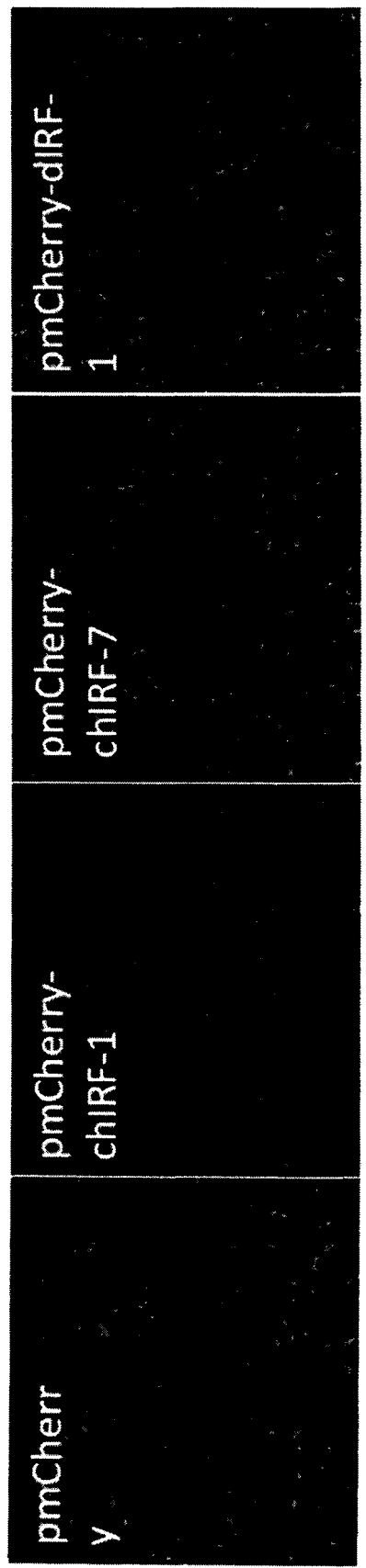
FIGS. 4A-4C depicts the results of experiments showing that chicken IRF-7 and duck IRF-1 can induce duck RIG-I promoter activity.

Example 6: Chicken IRF7 and Duck IRF1 Induce Promoter Activity of Duck RIG-I in DF-1 Cells To investigate whether IRFI, IRF7, STAT1 or STAT2 and IFNB are upregulated in RIG-I 2CARD stimulated cells, mRNA levels were measured in DF-1 cells transfected with p2024 or pGL-3 basic vector with or without co-transfected RIG-I 2CARD using qPCR. The housekeeping gene (GAPDH) was used as the internal reference. Transcript levels for IRF1, STAT1 and STAT2, IFNB were low and were not significantly different in RIG-I 2CARD treated and untreated groups at 24 h post-transfection (FIG. 4A). Upon phosphorylation, TFs are activated and translocated from cytoplasm to nucleus to perform their function of regulating gene transcription. It is not necessary to increase their expression level to regulate gene transcription. IRF1 was not induced, even though IRF1 has been reported to control inducible expression of human RIG-I. The upregulation of IRF7 and the MX genes demonstrated that an interferon response was stimulated.

Figure 4C:
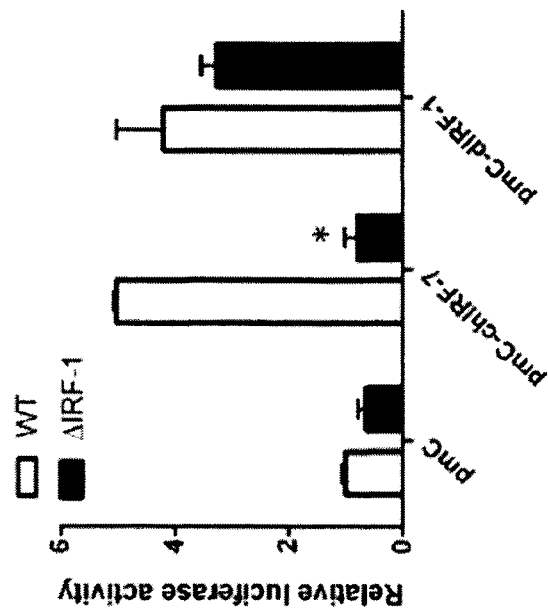
Figure 4B:
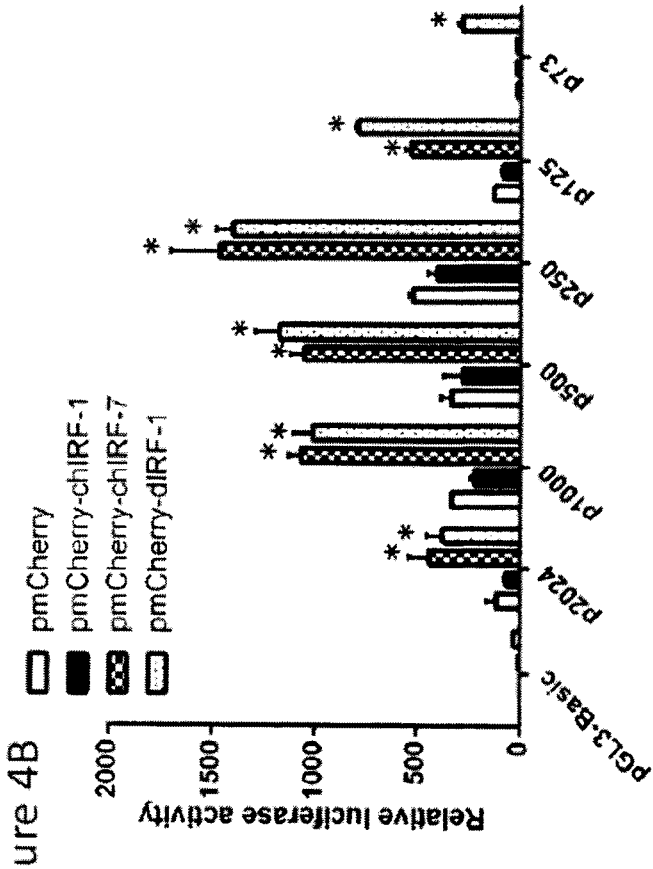

To determine whether chicken IRF factors can induce the duck RIG-I gene in chicken cells, chicken IRF1, chicken IRF7 and duck IRF1 were cloned. Because of the lack of effective antibodies to chicken IRFs, mCherry constructs were generated for chicken IRF1 (pmC-chIRF1) and chicken IRF7 (pmC-chIRF7), duck IRF1 (pmC-dIRF1) and mCherry (vector only) expression constructs and their expression was confirmed by fluorescence. All constructs were expressed, and staining was evident in both cytoplasm and nucleus (FIG. 4B).

To determine which IRFs could drive expression of duck RIG-I, each mCherry tagged protein was overexpressed in DF-1 cells with the RIG-I promoter constructs to investigate whether the promoter activity of duck RIG-I would be upregulated. The overexpression of chIRF-1 did not induce RIG-I promoter activity. However, overexpression of either chIRF-7 or dIRF-1 significantly induced duck RIG-I promoter activity (FIG. 4C). P73, which was not inducible in stimulated chicken cells, was induced by duck IRF1, and not chicken IRF1 or IRF7 (FIG. 4C). These results demonstrate that chicken IRF-7 induces duck RIG-I promoter activity in DF-1 cells. In contrast, it was previously shown by Su et al (J Cell Physiol 2001 213(2):502-10) that human IRF-1 is induced by type-I IFN and that it directly controlled human RIG-I expression.

Example 6: RIG-I Promoters do not Show Expected Phylogenetic Relationship

To determine whether the evolutionary relationship of RIG-I promoters was consistent to that of the RIG-I proteins, phylogenetic trees between duck and other species were created using MEGA7. RIG-I protein and promoter sequences were downloaded from the NCBI protein database and UCSC database, respectively. The mallard duck RIG-I is closer in evolutionary distance to other bird RIG-I sequences than to mammalian proteins (FIG. 5B). In contrast, RIG-I promoters do not follow the expected phylogenetic relationship between different species. Mouse RIG-I promoter appears to be closest to the duck RIG-I (FIG. 5A;

see also FIG.). This result differs from the phylogenetic analysis of MDA-5 promoters, which demonstrated taxonomic relationship among different vertebrates as described by Zhang et al. (Mol. Immunol. 2016 76:1-6), even though RIG-I and MDA-5 are in the same PRR family and their structures and functions are very similar. A phylogenetic tree of all avian RIG-I proteins is shown in FIG. 5C which indicates that Muscovy duck and goose are closest in evolutionary distance, as expected.

Example 7: Production of Gene-Edited Knockin Chicken Cells

Transgenic chickens have been generated in a variety of ways. The production of transgenic chickens through various strategies including lentiviral and viral vectors, transposons, transcription activator effector nuclease (TALEN), and zinc-finger nucleases (ZFN) has been reviewed (Doran et al., 2016, *Transgenic Res* 25, 307-319). The TALEN approach has recently been successful to generate gene knockouts in chickens (Park et al., 2014, Proc Natl Acad Sci USA 111, 12716-12721).

Gene editing of chicken genomes can be achieved through CRISPR/Cas9, which provides both a versatile and efficient approach (Hsu et al., 2014, *Cell* 157, 1262-1278). CRISPR/Cas9 can be used efficiently to modify chicken embryonic DF-1 cells and make alterations in somatic (Abu-Bonsrah et al., 2016, Sci Rep 6, 34524) and embryonic germ cells in the chicken embryo (Dimitrov et al., 2016, *PloS One* 11, e0154303). Repair through homologous recombination has been used to insert genes into primordial germ cells of chickens (knockins) and clonal lines of PGCs can be used to generate gene knockin birds (Dimitrov et al., 2016, infra).

Constructs of duck RIG-I under the control of full and partial promoters for expression in chicken cells are designed. One strategy involves the core promoter of duck RIG-I as described herein operably linked to drive expression of a spliced RIG-I gene coding sequence (corePR-RIG-Ics).

To identify a unique coding sequence that will allow targeting of the gene to the region of the chicken genome where the DDX58 gene is missing, a fragment corresponding to this region is amplified using the available chicken genome sequence. Based on comparative genomics the chicken is missing the DDX58 gene because of a large-scale rearrangement that reversed the arms of the Z chromosome. This rearrangement happened in an ancestor to the entire galliform lineage (chickens, turkeys, quails). The gene can be inserted in the Z chromosome. The Z chromosome contains many innate immune genes including the interferons, thus the chromosome may be upregulated during an interferon response through chromatin accessibility through epigenetic effects.

Using CRISPR technology optimized for gene editing in chickens (Zuo et al., 2016, Site-Directed Genome Knockout in Chicken Cell Line and Embryos Can Use CRISPR/Cas Gene Editing Technology. G3 (Bethesda) 6, 1787-1792) the duck DDX58 gene is inserted into the chicken Z chromosome. Targeting to this region is done using the vector with the chicken U6 promoter for driving expression of the CRISPR/Cas9, which provides both the Cas9 protein and the guide RNAs. Several cell lines are available to do this, including the chicken embryonic fibroblast DF-1 cells (Schaefer-Klein et al., 1998, Virology 248, 305-311), or a chicken lung cell line (Esnault et al., 2011, Virus Res 159, 32-42). Alternately, chicken DT40 B cells can be used, which have a known high success rate of homologous recombination (Harris et al., 2002, *Curr Biol* 12, 435-438). One approach involves using double-strand breaks made with CRISPR/Cas9 RNA using guide RNAs targeted to the Z chromosome sequence in the gene interval adjacent to the aconitase I gene (FIG. X). The targeting region is first amplified to confirm the sequence of the targeting region. The amplified sequence can then be used to attach 1 kb regions of homology to flank the RIG-I gene in the repair vector for directing repair of the double-strand breaks. This strategy has been successfully used to insert EGFP into the chicken IgH locus (Dimitrov et al., 2016, *PloS One* 11, e0154303). RIG-I can be epitope-tagged or RIG-I expression confirmed in chicken cells with reverse-transcription PCR of DNase-treated RNA. The generation of a DDX58 chicken cell line can be tested to confirm regulation of RIG-I in response to interferon, and influenza virus infection. The effect of RIG-I on the viral titre by plaque assay, $TCID_{50}$ or an examination of percent infected cells using high content microscopy, can be performed according to techniques previously described (Blyth et al., 2016, *Virol* 90, 103-116).

Example 8: Production of Gene-Edited Knockin Chicken

Production of transgenic chickens using cultured primordial germ cells as intermediates, and injection of clones of altered primordial germ cells (PGCs) has been described (Dimitrov et al., 2016, *PloS One* 11, e0154303). Lipofectamine 3000 reagent can be used to facilitate more efficient transfection of chicken primary cells. Alternatively, DNA and lipofectamine can be applied in vivo in the developing chick.

The CRISPR/Cas9 system is used for targeting genomic location and cleavage and the strategy of homologous recombination or non-homologous end joining (He et al., 2016, *Nucleic Acids Res* 44, e85) along with co-transfection of the repair construct to introduce either the promoter and DDX58 (RIG-I coding sequence) in chicken primordial germ cells or, alternatively, with the intact 20 kb DDX58 gene.

Cas9 nuclease generates site-specific breaks in double-strand DNA using a 20 nt guide RNA (gRNA). Efficient knock-in of large genes into human germ cells has been accomplished using either homology directed repair (which is inefficient) and non-homologous end joining pathways which is much more efficient and allows a larger insert (He et al., 2016, *Nucleic Acids Res* 44, e85). This strategy is used to knock in the duck DDX58 gene in chicken PGCs isolated and cultured as previously described (Song et al., 2014, *Biol Reprod* 90, 15). To produce gene edited birds, PGCs are selected that have been modified (Dimitrov et al., 2016), by incorporating the puromycin or neomycin resistance gene for selection and cloning of PGC lines. This approach achieved 100% targeting in one clone from transfected chicken PGCs (Dimitrov et al., 2016, *PloS One* 11, e0154303). In subsequent experiments, the selectable marker may be omitted and PGCs cloned to single cells by limiting dilution. Alternatively, the construct can be introduced to the PGCs in ovo in the embryo along with CRISPR/Cas9 targeting to generate chimeric germ line. To determine whether chicken cells expressing duck RIG-I have been generated, PGCs and offspring are screened for RIG-I using PCR and/or using specific polyclonal anti-duck RIG-I antibodies.

What is claimed is:

1. A vector comprising:
    nucleic acid sequence encoding a polypeptide operably linked to a promoter;
    the promoter comprising a nucleic acid sequence of SEQ ID NO: 01.

2. The vector of claim 1, wherein the polypeptide is a retinoic acid-inducible gene I (RIG-I) protein.

3. The vector of claim 2, wherein the RIG-I protein has the amino acid sequence of SEQ ID NO: 11.

4. The vector of claim 1 wherein the vector is a viral vector.

5. The vector of claim 4, wherein the viral vector is a retroviral vector, an adenoviral vector or an adeno-associated viral vector.

* * * * *

SEQUENCE LISTING

<160> NUMBER OF SEQ ID NOS: 27

<210> SEQ ID NO 1
<211> LENGTH: 250
<212> TYPE: DNA
<213> ORGANISM: Artificial sequence
<220> FEATURE:
<223> OTHER INFORMATION: synthetic sequence

<400> SEQUENCE: 1

| ctggacccca | ggcccgtgtc | tcggtgtccc | ggtgaggctg | ttggtggcga | tccgaggctc | 60 |
| acgaagctgc | gagccgctgc | ctatgcccgc | tggcggccag | agggcgggct | gcggatgggg | 120 |
| ccgcgatctc | cacacccgc  | gggggccgct | ttcgttttcc | attccccgcc | gggcctcgct | 180 |
| gcctttctgt | gccgagccgg | ttgggggggcc | gggccgggcc | gggccgggcg | gcggccggca | 240 |
| gagcccagcc | | | | | | 250 |

<210> SEQ ID NO 2
<211> LENGTH: 2024
<212> TYPE: DNA
<213> ORGANISM: Artificial sequence
<220> FEATURE:
<223> OTHER INFORMATION: synthetic sequence

<400> SEQUENCE: 2

| agctgatgac | ctgcaaaaag | ttggacatgc | aaaatttaaa | gctgaggaac | acaactacac | 60 |
| actatgctct | gaaaagaaa  | aataataat  | aacaatcaag | aaaagcattt | attcccacca | 120 |
| gctggaccac | actctctaag | gcaggacttg | gtgggtcaca | cagggaccct | tccagacagc | 180 |
| cacaagtgat | tttgggaaaa | agtaacatat | ttcctacacc | cttgcctaga | aagttctcca | 240 |
| gaaaactgct | cagcaccatg | gtttgcagta | gcacaagcag | gttaaggtct | tcccagtgct | 300 |
| gcagcttctt | ctcacccgat | gtgcttggcc | actgcaaccc | accagttacg | atgtagcata | 360 |
| aaacagccac | tgaggatatg | agcatgagat | accgcacagg | ccacaaccca | tcccactgca | 420 |
| ccactgccct | gcaccaacaa | agcctgggag | agcctcctgt | gctcaccagg | tgcatctcca | 480 |
| gcctggtggg | actgatccct | gctgccctca | gtacccctcc | tgcagccacc | ctgcccagca | 540 |
| ggtgcatccc | acctcctgca | tgcacgatca | gaggtgctat | tccccgtgc  | actccagtgc | 600 |
| cagctttgtt | gaagagcagc | aggtccactt | cactgggcag | attgacttct | ccatctaggg | 660 |
| ctggagaagc | agcaagcaag | gagtttgatt | tcctcctctt | ctcaggtgaa | ggacaagact | 720 |
| gggtttctgc | ttggcagagc | aattgcaacc | caccctcagc | actgatcttt | gaatcttcga | 780 |
| acactctgtc | tgtgaggagc | agaacctgag | tgctaatatc | actcattact | gaatgaaagc | 840 |
| tgtaataggc | atttctcaag | tggaaatagg | ctcaacaggc | actaccaagt | aaaaatgcct | 900 |
| ctctgctatg | tttgttacct | gtcaggctaa | tcaccatgct | ctacagggtg | tgttgggcaa | 960 |
| ctcacgtagg | ggctaacgct | tcttccttgt | tactcacaag | caaattaagc | cctaagagat | 1020 |
| taccttactg | aaaatgcagg | gtggagagat | gactgacagg | ggcttgttca | cctgccctttt | 1080 |
| tcttgctgca | gaagatgtcc | tctctcagtt | gttcagcatt | cccagtctca | gcagtggata | 1140 |
| gcctttctgt | gtcttggtca | gctgtgcatg | atatttctct | ggtccttctc | attgctctgg | 1200 |
| ttaagctaac | agcccaaatg | caagtctctc | ctagcctagg | gccatttgta | gcctagggca | 1260 |
| acagcagctg | ggagagagtg | agaaaatgtg | agagaacctt | acatttggga | tctttgggga | 1320 |
| gctgctgccc | atgggggacc | cgtgctggag | cagtttgctc | ctgggggatg | gatggatgga | 1380 |
| ccccgtggga | cggagccgtg | tgggagcagt | gcttgaagag | ctgctgcctg | tgggcagccc | 1440 |

```
ccgcgggatc ggttcgggaa ggacggcatc cctgggaggg accccatggg gagcagggc    1500 agagagggac cgtgagggag agggagcggc ggagacaaag tgccagggac tgaccgcagc    1560
ccccattccc ctgcactgcc tgggggggaa gaggtagagg agggtggatg gtggggaagg    1620
tgtttttcat ttccttttat tttttctcac tgctagtctg ttagtgatag gcaattaatt    1680
ctattctccc catccttgtg ccaacccctg agccctttcc atcgcatttt ctccccgttt    1740 cccttttgagg aggcggagtg ggagagcggc tgtgctggac cccaggcccg tgtctcggtg   1800
tcccggtgag gctgttggtg gcgatccgag gctcacgaag ctgcgagccg ctgcctatgc    1860
ccgctggcgg ccagagggcg ggctgcggat ggggccgcga tctccacacc ccgcggggc    1920 cgctttcgtt ttccattccc cgccgggcct cgctgccttt ctgtgccgag ccggttgggg    1980
ggccgggccg ggccgggccg ggcggcggcc ggcagagccc agcc                     2024
```

```
<210> SEQ ID NO 3
<211> LENGTH: 16
<212> TYPE: DNA
<213> ORGANISM: Artificial sequence
<220> FEATURE:
<223> OTHER INFORMATION: synthetic sequence

<400> SEQUENCE: 3
cggccagagg gcgggc                                                    16

<210> SEQ ID NO 4
<211> LENGTH: 21
<212> TYPE: DNA
<213> ORGANISM: Artificial sequence
<220> FEATURE:
<223> OTHER INFORMATION: synthetic sequence

<400> SEQUENCE: 4
ggccgctttc gttttccatt c                                              21

<210> SEQ ID NO 5
<211> LENGTH: 12
<212> TYPE: DNA
<213> ORGANISM: Artificial sequence
<220> FEATURE:
<223> OTHER INFORMATION: synthetic sequence

<400> SEQUENCE: 5
acgaagctgc ga                                                        12

<210> SEQ ID NO 6
<211> LENGTH: 16
<212> TYPE: DNA
<213> ORGANISM: Artificial sequence
<220> FEATURE:
<223> OTHER INFORMATION: synthetic sequence

<400> SEQUENCE: 6
cggccagagg gcgggc                                                    16

<210> SEQ ID NO 7
<211> LENGTH: 21
<212> TYPE: DNA
<213> ORGANISM: Artificial sequence
<220> FEATURE:
<223> OTHER INFORMATION: synthetic sequence

<400> SEQUENCE: 7
```

```
ggccgctttc gttttccatt c                                              21
```

<210> SEQ ID NO 8
<211> LENGTH: 157
<212> TYPE: DNA
<213> ORGANISM: Artificial sequence
<220> FEATURE:
<223> OTHER INFORMATION: synthetic sequence

<400> SEQUENCE: 8

```
cggccagagg gcgggctgcg gatggggccg cgatctccac accccgcggg ggccgctttc    60
gttttccatt ccccgccggg cctcgctgcc tttctgtgcc gagccggttg gggggccggg   120
ccgggccggg ccgggcggcg gccggcagag cccagcc                            157
```

<210> SEQ ID NO 9
<211> LENGTH: 178
<212> TYPE: DNA
<213> ORGANISM: Artificial sequence
<220> FEATURE:
<223> OTHER INFORMATION: synthetic sequence

<400> SEQUENCE: 9

```
gccgctgcct atgcccgctg gcggccagag ggcgggctgc ggatggggcc gcgatctcca    60
caccccgcgg gggccgcttt cgttttccat tccccgccgg gcctcgctgc ctttctgtgc   120
cgagccggtt ggggggccgg gccgggccgg gccgggcggc ggccggcaga gcccagcc    178
```

<210> SEQ ID NO 10
<211> LENGTH: 4
<212> TYPE: PRT
<213> ORGANISM: Artificial sequence
<220> FEATURE:
<223> OTHER INFORMATION: synthetic sequence

<400> SEQUENCE: 10

Asp Glu Ala Asp
1

<210> SEQ ID NO 11
<211> LENGTH: 932
<212> TYPE: PRT
<213> ORGANISM: Anas platyrhynchos

<400> SEQUENCE: 11

Met Thr Ala Asp Glu Lys Arg Ser Leu Gln Cys Tyr Arg Arg Tyr Ile
1               5                   10                  15

Glu Arg Ser Leu Asn Pro Val Tyr Val Leu Gly Asn Met Thr Asp Trp
            20                  25                  30

Leu Pro Asp Glu Leu Arg Glu Arg Ile Arg Lys Glu Glu Glu Arg Gly
        35                  40                  45

Val Ser Gly Ala Ala Ala Leu Phe Leu Asp Ala Val Leu Gln Leu Glu
    50                  55                  60

Ala Arg Gly Trp Phe Arg Gly Met Leu Asp Ala Met Leu Ala Ala Gly
65                  70                  75                  80

Tyr Thr Gly Leu Ala Glu Ala Ile Glu Asn Trp Asp Phe Ser Lys Leu
                85                  90                  95

Glu Lys Leu Glu Leu His Arg Gln Leu Leu Lys Arg Ile Glu Ala Thr
            100                 105                 110

Met Leu Glu Val Asp Pro Val Ala Leu Ile Pro Tyr Ile Ser Thr Cys
        115                 120                 125

-continued

```
Leu Ile Asp Arg Glu Cys Glu Glu Ile Gln Gln Ile Ser Glu Asn Arg
130                 135                 140
Ser Lys Ala Ala Gly Ile Thr Lys Leu Ile Glu Cys Leu Cys Arg Ser
145                 150                 155                 160
Asp Lys Glu His Trp Pro Lys Ser Leu Gln Leu Ala Leu Asp Thr Thr
                165                 170                 175
Gly Tyr Tyr Arg Ala Ser Glu Leu Trp Asp Ile Arg Glu Asp Asn Ala
                180                 185                 190
Lys Asp Val Asp Ser Glu Met Thr Asp Ala Ser Glu Asp Cys Leu Glu
                195                 200                 205
Ala Ser Met Thr Tyr Ser Glu Glu Ala Glu Pro Asp Asp Asn Leu Ser
210                 215                 220
Glu Asn Leu Gly Ser Ala Ala Glu Gly Ile Gly Lys Pro Pro Pro Val
225                 230                 235                 240
Tyr Glu Thr Lys Lys Ala Arg Ser Tyr Gln Ile Glu Leu Ala Gln Pro
                245                 250                 255
Ala Ile Asn Gly Lys Asn Ala Leu Ile Cys Ala Pro Thr Gly Ser Gly
                260                 265                 270
Lys Thr Phe Val Ser Ile Leu Ile Cys Glu His His Phe Gln Asn Met
275                 280                 285
Pro Ala Gly Arg Lys Ala Lys Val Val Phe Leu Ala Thr Lys Val Pro
290                 295                 300
Val Tyr Glu Gln Gln Lys Asn Val Phe Lys His Phe Glu Arg Gln
305                 310                 315                 320
Gly Tyr Ser Val Gln Gly Ile Ser Gly Glu Asn Phe Ser Asn Val Ser
                325                 330                 335
Val Glu Lys Val Ile Glu Asp Ser Asp Ile Ile Val Val Thr Pro Gln
                340                 345                 350
Ile Leu Val Asn Ser Phe Glu Asp Gly Thr Leu Thr Ser Leu Ser Ile
                355                 360                 365
Phe Thr Leu Met Ile Phe Asp Glu Cys His Asn Thr Thr Gly Asn His
                370                 375                 380
Pro Tyr Asn Val Leu Met Thr Arg Tyr Leu Glu Gln Lys Phe Asn Ser
385                 390                 395                 400
Ala Ser Gln Leu Pro Gln Ile Leu Gly Leu Thr Ala Ser Val Gly Val
                405                 410                 415
Gly Asn Ala Lys Asn Ile Glu Glu Thr Ile Glu His Ile Cys Ser Leu
                420                 425                 430
Cys Ser Tyr Leu Asp Ile Gln Ala Ile Ser Thr Val Arg Glu Asn Ile
                435                 440                 445
Gln Glu Leu Gln Arg Phe Met Asn Lys Pro Glu Ile Asp Val Arg Leu
450                 455                 460
Val Lys Arg Arg Ile His Asn Pro Phe Ala Ala Ile Ile Ser Asn Leu
465                 470                 475                 480
Met Ser Glu Thr Glu Ala Leu Met Arg Thr Ile Tyr Ser Val Asp Thr
                485                 490                 495
Leu Ser Gln Asn Ser Lys Lys Asp Phe Gly Thr Gln Asn Tyr Glu His
                500                 505                 510
Trp Ile Val Val Thr Gln Arg Lys Cys Arg Leu Leu Gln Leu Glu Asp
                515                 520                 525
Lys Glu Glu Glu Ser Arg Ile Cys Arg Ala Leu Phe Ile Cys Thr Glu
530                 535                 540
His Leu Arg Lys Tyr Asn Asp Ala Leu Ile Ile Ser Glu Asp Ala Arg
```

```
            545                 550                 555                 560
        Ile Ile Asp Ala Leu Ser Tyr Leu Thr Glu Phe Phe Thr Asn Val Lys
                        565                 570                 575

Asn Gly Pro Tyr Thr Glu Leu Glu Gln His Leu Thr Ala Lys Phe Gln
                        580                 585                 590

Glu Lys Glu Pro Glu Leu Ile Ala Leu Ser Lys Asp Glu Thr Asn Glu
                        595                 600                 605

Asn Pro Lys Leu Glu Glu Leu Val Cys Ile Leu Asp Asp Ala Tyr Arg
                        610                 615                 620

Tyr Asn Pro Gln Thr Arg Thr Leu Leu Phe Ala Lys Thr Arg Ala Leu
        625                 630                 635                 640

Val Ser Ala Leu Lys Lys Cys Met Glu Glu Asn Pro Ile Leu Asn Tyr
                        645                 650                 655

Ile Lys Pro Gly Val Leu Met Gly Arg Gly Arg Arg Asp Gln Thr Thr
                        660                 665                 670

Gly Met Thr Leu Pro Ser Gln Lys Gly Val Leu Asp Ala Phe Lys Thr
                        675                 680                 685

Ser Lys Asp Asn Arg Leu Leu Ile Ala Thr Ser Val Ala Asp Glu Gly
                        690                 695                 700

Ile Asp Ile Val Gln Cys Asn Leu Val Val Leu Tyr Glu Tyr Ser Gly
        705                 710                 715                 720

Asn Val Thr Lys Met Ile Gln Val Arg Gly Arg Gly Arg Ala Ala Gly
                        725                 730                 735

Ser Lys Cys Ile Leu Val Thr Ser Lys Thr Glu Val Val Glu Asn Glu
                        740                 745                 750

Lys Cys Asn Arg Tyr Lys Glu Glu Met Met Asn Lys Ala Val Glu Lys
                        755                 760                 765

Ile Gln Lys Trp Asp Glu Glu Thr Phe Ala Lys Lys Ile His Asn Leu
                        770                 775                 780

Gln Met Lys Glu Arg Val Leu Arg Asp Ser Arg Arg Lys Glu Ile Lys
        785                 790                 795                 800

Pro Lys Val Val Glu Gly Gln Lys Asn Leu Leu Cys Gly Lys Cys Lys
                        805                 810                 815

Ala Tyr Ala Cys Ser Thr Asp Asp Ile Arg Ile Ile Lys Asp Ser His
                        820                 825                 830

His Ile Val Leu Gly Glu Ala Phe Lys Glu Arg Tyr Thr Thr Lys Pro
                        835                 840                 845

His Lys Lys Pro Met Gln Phe Asp Gly Phe Glu Lys Lys Ser Lys Met
                        850                 855                 860

Tyr Cys Arg Asn Asn Asn Cys Gln His Asp Trp Gly Ile Thr Val Lys
        865                 870                 875                 880

Tyr Leu Thr Phe Asp Asn Leu Pro Val Ile Lys Ile Lys Ser Phe Val
                        885                 890                 895

Met Glu Ser Thr Ala Thr Gly Thr Gln Met Asp Phe Gln Lys Trp Lys
                        900                 905                 910

Ser Ile Asn Ser Ser Leu Lys Asn Phe Asp Val Glu Glu Met Ser Asn
                        915                 920                 925

Leu Tyr Pro Pro
            930

<210> SEQ ID NO 12
<211> LENGTH: 23
<212> TYPE: DNA
<213> ORGANISM: Artificial sequence
```

```
<220> FEATURE:
<223> OTHER INFORMATION: synthetic sequence

<400> SEQUENCE: 12
ccaagtaaaa atgcctctct gct                                              23

<210> SEQ ID NO 13
<211> LENGTH: 24
<212> TYPE: DNA
<213> ORGANISM: Artificial sequence
<220> FEATURE:
<223> OTHER INFORMATION: synthetic sequence

<400> SEQUENCE: 13
gcatcgcgtc cagcatccct cgga                                             24

<210> SEQ ID NO 14
<211> LENGTH: 22
<212> TYPE: DNA
<213> ORGANISM: Artificial sequence
<220> FEATURE:
<223> OTHER INFORMATION: synthetic sequence

<400> SEQUENCE: 14
agctgatgac ctgcaaaaag tt                                               22

<210> SEQ ID NO 15
<211> LENGTH: 21
<212> TYPE: DNA
<213> ORGANISM: Artificial sequence
<220> FEATURE:
<223> OTHER INFORMATION: synthetic sequence

<400> SEQUENCE: 15
gttgaggctc cgctcgatgt a                                                21

<210> SEQ ID NO 16
<211> LENGTH: 22
<212> TYPE: DNA
<213> ORGANISM: Artificial sequence
<220> FEATURE:
<223> OTHER INFORMATION: synthetic sequence

<400> SEQUENCE: 16
agctgatgac ctgcaaaaag tt                                               22

<210> SEQ ID NO 17
<211> LENGTH: 19
<212> TYPE: DNA
<213> ORGANISM: Artificial sequence
<220> FEATURE:
<223> OTHER INFORMATION: synthetic sequence

<400> SEQUENCE: 17
ggctgggctc tgccggccg                                                   19

<210> SEQ ID NO 18
<211> LENGTH: 934
<212> TYPE: PRT
<213> ORGANISM: Anser anser

<400> SEQUENCE: 18

Met Thr Ala Asp Glu Lys Arg Ser Leu Gln Cys Tyr Arg Arg Tyr Ile
1               5                   10                  15

Glu Arg Ser Leu Asn Pro Val Tyr Val Leu Gly Asn Met Ala Asp Trp
```

```
                 20                  25                  30
Leu Pro Asp Glu Leu Arg Glu Arg Ile Arg Lys Glu Glu Arg Gly
             35                  40                  45
Val Ser Gly Ala Ala Ala Leu Phe Leu Asp Ala Val Leu Gln Leu Glu
 50                  55                  60
Ala Arg Gly Trp Phe Arg Gly Met Leu Asp Ala Met Leu Ala Ala Gly
 65                  70                  75                  80
His Thr Gly Leu Ala Glu Ala Ile Glu Asn Trp Asp Phe Ser Lys Leu
                 85                  90                  95
Glu Lys Leu Glu Leu His Arg Gln Leu Leu Lys Arg Ile Glu Ala Thr
             100                 105                 110
Met Leu Glu Val Asp Pro Val Leu Ile Pro Tyr Ile Asn Thr Cys
         115                 120                 125
Leu Ile Asp Arg Glu Cys Glu Ile Gln Gln Ile Ser Glu Ser Arg
         130                 135                 140
Ser Lys Ala Ala Gly Ile Thr Lys Leu Ile Glu Cys Leu Cys Arg Ser
145                 150                 155                 160
Asp Lys Glu His Trp Pro Lys Ser Leu Gln Leu Ala Leu Asp Asn Thr
                 165                 170                 175
Gly Tyr Tyr Arg Ala Ser Glu Leu Trp Asp Met Arg Glu Asp Asn Ala
             180                 185                 190
Lys Asp Val Asp Ser Glu Met Thr Asp Ala Ser Glu Asp Cys Leu Glu
         195                 200                 205
Thr Ser Met Thr Tyr Ser Glu Glu Ala Glu Pro Asp Asp Asn Leu Ser
         210                 215                 220
Glu Asn Leu Gly Ser Ala Ala Glu Gly Ile Asp Lys Pro Pro Val
225                 230                 235                 240
Tyr Glu Ala Lys Lys Ala Arg Ser Tyr Gln Ile Glu Leu Ala Gln Pro
                 245                 250                 255
Ala Ile Asn Gly Lys Asn Ala Leu Ile Cys Ala Pro Thr Gly Ser Gly
             260                 265                 270
Lys Thr Phe Ile Ala Leu Leu Val Cys Glu His His Phe Gln Asn Met
         275                 280                 285
Pro Ala Gly Arg Lys Gly Lys Val Phe Leu Ala Thr Lys Val Pro
     290                 295                 300
Val Tyr Glu Gln Gln Lys Asn Val Phe Lys Gln His Phe Glu Arg Gln
305                 310                 315                 320
Gly Tyr Ser Ile Gln Gly Val Ser Gly Glu Asn Phe Ser Asn Val Ser
                 325                 330                 335
Val Glu Asn Val Ile Glu Asp Asn Asp Ile Val Leu Thr Pro Gln
             340                 345                 350
Ile Leu Val Asn Ser Phe Glu Asp Gly Thr Leu Thr Ser Leu Ser Val
         355                 360                 365
Phe Thr Leu Met Ile Phe Asp Glu Cys His Asn Thr Thr Gly Asn His
     370                 375                 380
Pro Tyr Asn Val Leu Met Thr Arg Tyr Leu Glu Gln Lys Phe Asn Ser
385                 390                 395                 400
Pro Ala Ser Gln Leu Pro Gln Ile Leu Gly Leu Thr Ala Ser Val Gly
                 405                 410                 415
Val Gly Asn Ala Lys Asn Ile Glu Glu Thr Ile Glu His Ile Cys Ser
             420                 425                 430
Leu Cys Ser Tyr Leu Asp Ile Gln Ala Ile Ser Thr Val Arg Glu Asn
         435                 440                 445
```

```
Ile Gln Asp Leu Gln Arg Phe Met Asn Lys Pro Glu Ile Asp Val Arg
    450                 455                 460

Leu Val Lys Arg Arg Val His Asn His Phe Ala Val Ile Ile Ser Asp
465                 470                 475                 480

Leu Met Ser Glu Thr Glu Ala Leu Met Arg Lys Ile Tyr Ser Val Gly
                485                 490                 495

Thr Val Ser Gln Asn Ser Arg Lys Asp Phe Gly Thr Gln Lys Tyr Glu
                500                 505                 510

His Trp Ile Val Val Thr Gln Arg Lys Cys Arg Leu Leu Gln Leu Glu
        515                 520                 525

Asp Lys Glu Glu Glu Ser Arg Ile Cys Arg Ala Leu Phe Ile Cys Thr
        530                 535                 540

Glu His Leu Arg Lys Tyr Asn Asp Ala Leu Ile Ile Ser Glu Asp Ala
545                 550                 555                 560

Arg Ile Ile Asp Ala Leu Ser Tyr Leu Thr Glu Phe Phe Thr Asn Val
                565                 570                 575

Lys Asn Gly Pro Tyr Thr Glu Leu Glu Gln His Leu Thr Ala Lys Phe
                580                 585                 590

Gln Glu Lys Glu Pro Glu Leu Thr Ala Leu Ser Lys Asp Glu Thr Asn
        595                 600                 605

Glu Asn Pro Lys Leu Glu Glu Leu Ala Cys Ile Leu Asp Asp Ala Tyr
        610                 615                 620

Cys Tyr Asn Pro Gln Thr Arg Thr Leu Leu Phe Ala Lys Thr Arg Ala
625                 630                 635                 640

Leu Val Ala Ala Leu Lys Lys Cys Met Glu Glu Asn Pro Ile Leu Ser
                645                 650                 655

Tyr Ile Lys Pro Asp Val Leu Met Gly Arg Gly Arg Arg Asp Gln Lys
                660                 665                 670

Thr Gly Met Thr Leu Pro Ser Gln Lys Gly Val Leu Asp Ala Phe Lys
        675                 680                 685

Thr Ser Lys Asp Ser Arg Leu Leu Ile Ala Thr Ser Val Ala Asp Glu
        690                 695                 700

Gly Ile Asp Ile Ala Gln Cys Asn Leu Val Val Leu Tyr Glu Tyr Ser
705                 710                 715                 720

Gly Asn Val Thr Lys Met Ile Gln Val Arg Gly Arg Gly Arg Ala Ala
                725                 730                 735

Gly Ser Lys Cys Ile Leu Val Thr Ser Lys Thr Glu Val Val Glu Asn
                740                 745                 750

Glu Lys Cys Asn Arg Tyr Lys Glu Glu Met Met Asn Lys Ala Ile Glu
        755                 760                 765

Lys Leu Gln Glu Trp Asp Glu Glu Thr Phe Ala Lys Lys Ile His Asn
        770                 775                 780

Leu Gln Met Lys Glu Lys Val Leu Arg Asp Ser Arg Lys Lys Glu Ile
785                 790                 795                 800

Lys Pro Lys Val Val Glu Gly Gln Lys Asn Leu Leu Cys Gly Lys Cys
                805                 810                 815

Lys Ala Tyr Ala Cys Ser Thr Asp Asp Ile Arg Ile Ile Lys Glu Ser
                820                 825                 830

His His Val Val Leu Gly Glu Ala Phe Lys Glu Arg Tyr Ile Thr Lys
        835                 840                 845

Pro His Lys Lys Pro Met Gln Phe Asp Gly Phe Glu Lys Lys Ser Lys
        850                 855                 860
```

```
Met His Cys Arg Asn Asn Cys Gln His Asp Trp Gly Ile Thr Val
865                 870                 875                 880

Lys Tyr Leu Thr Phe Asp Asn Leu Pro Val Ile Lys Ile Lys Ser Phe
                885                 890                 895

Val Val Gln Ser Ala Ala Thr Gly Thr Gln Met Asp Phe Gln Arg Trp
            900                 905                 910

Lys Ser Ile Asn Ser Ser Leu Lys Asn Phe Asp Val Glu Glu Met Ser
        915                 920                 925

Asn Leu Tyr Pro Pro Phe
        930

<210> SEQ ID NO 19
<211> LENGTH: 934
<212> TYPE: PRT
<213> ORGANISM: Cairina moschata

<400> SEQUENCE: 19

Met Thr Ala Asp Glu Lys Arg Ser Leu Gln Cys Tyr Arg Arg Tyr Ile
1               5                   10                  15

Glu Arg Ser Leu Asn Pro Val Tyr Val Leu Gly Asn Met Thr Asp Trp
            20                  25                  30

Leu Pro Asp Glu Leu Arg Glu Arg Ile Arg Lys Glu Glu Arg Gly
        35                  40                  45

Val Ser Gly Ala Ala Ala Leu Phe Leu Asp Ala Val Leu Gln Leu Glu
    50                  55                  60

Ala Gln Gly Trp Phe Arg Gly Met Leu Asp Ala Met Leu Ala Ala Gly
65                  70                  75                  80

Tyr Thr Gly Leu Ala Glu Ala Ile Glu Asn Trp Asp Phe Ser Lys Leu
                85                  90                  95

Glu Lys Leu Glu Leu His Arg Gln Leu Leu Lys Arg Ile Glu Ala Thr
            100                 105                 110

Met Leu Glu Val Asp Pro Val Ala Leu Ile Pro Tyr Ile Asn Thr Cys
        115                 120                 125

Leu Ile Asp Arg Glu Cys Glu Glu Ile Gln Gln Ile Ser Glu Asn Arg
130                 135                 140

Ser Lys Ala Ala Gly Ile Thr Lys Leu Ile Glu Cys Leu Cys Arg Ser
145                 150                 155                 160

Asp Lys Glu His Trp Pro Lys Ser Leu Gln Leu Ala Leu Asp Thr Thr
                165                 170                 175

Gly Tyr Tyr Arg Ala Ser Glu Leu Trp Asp Ile Arg Gly Asp Asn Ala
            180                 185                 190

Lys Asp Val Asp Ser Glu Met Thr Asp Ala Ser Glu Asp Cys Leu Glu
        195                 200                 205

Ala Ser Met Thr Tyr Ser Glu Ala Glu Pro Asp Asn Leu Ser
210                 215                 220

Glu Asn Leu Gly Ser Ala Ala Glu Gly Ile Gly Lys Pro Pro Val
225                 230                 235                 240

Tyr Glu Thr Lys Lys Ala Arg Ser Tyr Gln Ile Glu Leu Ala Gln Pro
                245                 250                 255

Ala Ile Asn Gly Lys Asn Ala Leu Ile Cys Ala Pro Thr Gly Ser Gly
            260                 265                 270

Lys Thr Phe Val Ser Ile Leu Ile Cys Glu His His Phe Gln Asn Met
        275                 280                 285

Pro Ala Gly Arg Lys Ala Lys Val Val Phe Leu Ala Thr Lys Val Pro
290                 295                 300
```

-continued

```
Val Tyr Glu Gln Gln Lys Asn Val Phe Lys His His Phe Glu Arg Gln
305                 310                 315                 320

Gly Tyr Ser Val Gln Gly Ile Ser Gly Glu Asn Phe Ser Asn Val Ser
            325                 330                 335

Val Glu Lys Val Ile Glu Asp Ser Asp Ile Ile Val Thr Pro Gln
        340                 345                 350

Ile Leu Val Asn Ser Phe Glu Asp Gly Thr Leu Thr Ser Leu Ser Ile
        355                 360                 365

Phe Thr Leu Met Ile Phe Asp Glu Cys His Asn Thr Thr Gly Asn His
    370                 375                 380

Pro Tyr Asn Val Leu Met Thr Arg Tyr Leu Gln Lys Phe Asn Ser
385                 390                 395                 400

Ser Ala Ser Gln Leu Pro Gln Ile Leu Gly Leu Thr Ala Ser Val Gly
                405                 410                 415

Val Gly Asn Ala Lys Asn Ile Glu Glu Thr Ile Glu His Ile Cys Ser
            420                 425                 430

Leu Cys Ser Tyr Leu Asp Ile Gln Ala Ile Ser Thr Val Arg Glu Asn
        435                 440                 445

Ile Gln Glu Leu Arg Arg Phe Met Asn Lys Pro Glu Ile Asp Val Arg
    450                 455                 460

Leu Val Lys Arg Arg Val His Asn Pro Phe Ala Val Ile Ile Ser Asp
465                 470                 475                 480

Leu Met Ser Glu Thr Glu Ala Leu Met Arg Thr Ile Tyr Ser Val Asp
                485                 490                 495

Thr Ile Ser Gln Asn Ser Lys Lys Asp Phe Gly Thr Gln Asn Tyr Glu
            500                 505                 510

His Trp Ile Val Thr Gln Arg Lys Cys Arg Leu Leu Gln Leu Glu
        515                 520                 525

Asp Lys Glu Glu Glu Ser Arg Ile Cys Arg Ala Leu Phe Ile Cys Thr
530                 535                 540

Glu His Leu Arg Lys Tyr Asn Asp Ala Leu Ile Ile Ser Glu Asp Ala
545                 550                 555                 560

Arg Ile Ile Asp Ala Leu Ser Tyr Leu Thr Glu Phe Phe Thr Asn Val
                565                 570                 575

Lys Asn Gly Pro Tyr Thr Glu Leu Glu Gln His Leu Thr Ala Lys Phe
            580                 585                 590

Gln Glu Lys Glu Pro Glu Leu Ile Ala Leu Ser Lys Asp Glu Thr Asn
        595                 600                 605

Glu Asn Pro Lys Leu Glu Glu Leu Ala Cys Ile Leu Asp Asp Ala Tyr
    610                 615                 620

Arg Tyr Asn Pro Gln Thr Arg Thr Leu Leu Phe Ala Lys Thr Arg Ala
625                 630                 635                 640

Leu Val Ser Ala Leu Lys Lys Cys Met Glu Glu Asn Pro Ile Leu Ser
                645                 650                 655

Tyr Ile Lys Pro Gly Val Leu Met Gly Arg Gly Arg Arg Asp Gln Thr
            660                 665                 670

Thr Gly Met Thr Leu Pro Ser Gln Lys Gly Val Leu Asp Ala Phe Lys
        675                 680                 685

Thr Ser Lys Asp Asn Arg Leu Leu Ile Ala Thr Ser Val Ala Asp Glu
    690                 695                 700

Gly Ile Asp Ile Val Gln Cys Asn Leu Val Val Leu Tyr Glu Tyr Ser
705                 710                 715                 720
```

-continued

```
Gly Asn Val Thr Lys Met Ile Gln Val Arg Gly Arg Gly Arg Ala Ala
                725                 730                 735

Gly Ser Gln Cys Ile Leu Val Thr Ser Lys Thr Glu Val Val Glu Asn
            740                 745                 750

Glu Lys Cys Asn Arg Tyr Lys Glu Met Met Asn Thr Ala Val Glu
        755                 760                 765

Lys Ile Gln Glu Trp Asp Glu Lys Thr Phe Ala Lys Lys Ile His Asn
    770                 775                 780

Leu Gln Met Lys Glu Arg Val Leu Arg Asp Ser Arg Lys Glu Ile
785                 790                 795                 800

Lys Pro Lys Val Val Glu Gly Gln Lys Asn Leu Leu Cys Gly Lys Cys
                805                 810                 815

Lys Ala Tyr Ala Cys Ser Thr Asp Asp Ile Arg Ile Ile Lys Asp Ser
            820                 825                 830

His His Ile Val Ile Gly Glu Ala Phe Lys Glu Arg Tyr Ile Thr Lys
        835                 840                 845

Pro His Lys Lys Pro Met Gln Phe Asp Gly Phe Glu Lys Ser Lys
    850                 855                 860

Met Tyr Cys Arg Asn Asn Asn Cys Gln His Asp Trp Gly Ile Thr Val
865                 870                 875                 880

Lys Tyr Leu Thr Phe Asp Asn Leu Pro Val Ile Lys Ile Lys Ser Phe
                885                 890                 895

Val Met Glu Ser Thr Ala Thr Gly Thr Gln Met Asp Phe Gln Lys Trp
            900                 905                 910

Lys Ser Ile Asn Ser Ser Leu Lys Asn Phe Asp Val Glu Glu Met Ser
        915                 920                 925

Asn Leu Tyr Pro Pro Phe
    930

<210> SEQ ID NO 20
<211> LENGTH: 892
<212> TYPE: PRT
<213> ORGANISM: Columba livia

<400> SEQUENCE: 20

Met Lys Glu Arg Val Arg Lys Glu Glu Lys Gly Val Thr Ala Ala
1               5                   10                  15

Ala Ala Leu Phe Leu Asp Ile Ile Leu Gln Leu Glu Ala Glu Gly Trp
            20                  25                  30

Leu Arg Gly Phe Leu Asp Ala Leu Ala Ala Gly Tyr Thr Gly Leu
        35                  40                  45

Ala Glu Ala Ile Glu Asn Trp Asp Phe Ser Lys Leu Glu Lys Leu Glu
50                  55                  60

Leu Tyr Arg Gln Leu Leu Lys Arg Ile Glu Ala Thr Met Leu Glu Val
65                  70                  75                  80

Asp Pro Val Ala Leu Met Pro Tyr Met Asn Ser Cys Leu Ile Glu Arg
                85                  90                  95

Glu Cys Asp Glu Ile Leu Gln Ile Ser Glu Tyr Arg Ser Lys Ala Ala
            100                 105                 110

Gly Ile Thr Lys Leu Ile Glu Cys Leu Cys Arg Ser Asp Lys Glu Asn
        115                 120                 125

Trp Pro Lys Ser Leu Gln Leu Ala Leu Asp Asn Thr Gly Tyr Tyr Asn
    130                 135                 140

Ala Ser Glu Leu Trp Gly Ile Arg Glu Asp Arg Gly Lys Asp Val Asp
145                 150                 155                 160
```

-continued

Gly Glu Met Ala Asp Ala Ser Glu Ser Ser Phe Ile Arg Met Thr
                165                 170                 175

Phe Ser Glu Glu Ala Glu Cys Asp Asn Asn Leu Ser Glu Asn Val Ser
            180                 185                 190

Ser Ala Ser Gly Thr Tyr Gln Ser Ser Ala Val Tyr Glu Pro Lys Glu
        195                 200                 205

Ala Arg Ser Tyr Gln Ile Glu Leu Ala Gln Pro Ala Ile Asn Gly Lys
    210                 215                 220

Asn Thr Leu Ile Cys Ala Pro Thr Gly Ser Gly Lys Thr Phe Val Ala
225                 230                 235                 240

Ile Leu Ile Cys Glu His His Phe Gln Asn Met Pro Thr Gly Gln Lys
                245                 250                 255

Ala Lys Val Val Phe Leu Ala Thr Lys Val Pro Val Tyr Glu Gln Gln
            260                 265                 270

Lys Asn Val Phe Lys Gln His Phe Gly Arg Ser Gly Tyr Ser Val Gln
        275                 280                 285

Gly Ile Cys Gly Glu Ile Val Ala Asn Val Ser Val Glu Lys Val Ile
    290                 295                 300

Gln Asp Ser Asp Ile Ile Val Leu Thr Pro Gln Ile Leu Val Asn Thr
305                 310                 315                 320

Ile Lys Lys Gly Thr Leu Ser Ser Leu Ser Ile Phe Thr Leu Met Ile
                325                 330                 335

Phe Asp Glu Cys His Asn Thr Thr Gly Asn His Pro Tyr Asn Val Leu
            340                 345                 350

Met Thr Lys Tyr Leu Glu Gln Lys Phe Asp Ser Ser Ala Asn Gln Leu
        355                 360                 365

Pro Gln Ile Val Gly Leu Thr Ala Ser Val Gly Val Gly Asn Ala Lys
    370                 375                 380

Asp Ile Thr Thr Thr Glu Glu His Ile Cys Thr Leu Cys Ser Tyr Leu
385                 390                 395                 400

Asp Ile Gln Ala Ile Ser Thr Val Arg Glu Asn Lys Glu Glu Leu Gln
                405                 410                 415

Arg Phe Ile Asn Lys Pro Glu Thr Asp Val Arg Leu Val Arg Met Arg
            420                 425                 430

Leu Gln Asn His Phe Ala Asp Ile Ile Ser Gly Leu Met Ser Glu Thr
        435                 440                 445

Glu Ala Arg Met Arg Glu Ile Tyr Ser Leu Asp Asp Ile Ser Gln Met
    450                 455                 460

Asn Lys Asn Asp Phe Gly Thr Gln Lys Tyr Glu His Trp Ile Val Thr
465                 470                 475                 480

Thr Gln Lys Lys Tyr Arg Leu Leu Gln Leu Ala Asp Lys Glu Lys Glu
                485                 490                 495

Ser Ser Ile Cys Arg Asp Ile Phe Ile Cys Thr Glu His Leu Arg Lys
            500                 505                 510

Phe Asn Asp Ala Leu Ile Ile Ser Glu Asp Ala Arg Ile Glu Asp Ala
        515                 520                 525

Leu Ala Tyr Leu Thr Glu Phe Phe Thr Asn Val Lys Asn Gly Pro Phe
    530                 535                 540

Thr Glu Leu Glu Lys Gln Leu Thr Ala Arg Phe Gln Glu Lys Glu Pro
545                 550                 555                 560

Glu Leu Thr Ala Leu Ser Lys Asp Gln Ser Asn Glu Asn Pro Lys Leu
                565                 570                 575

```
Glu Glu Leu Ala Ala Ile Leu Asp Glu Ala Tyr Arg Tyr Asn Pro Gln
                580                 585                 590

Thr Arg Thr Leu Leu Phe Val Lys Thr Arg Ala Leu Val Ala Ala Leu
            595                 600                 605

Lys Lys Trp Met Lys Ala Asn Pro Leu Leu Ser His Ile Lys Pro Asp
610                 615                 620

Val Leu Met Gly His Gly Arg Asp His Lys Thr Gly Met Thr Leu
625                 630                 635                 640

Pro Met Gln Lys Ala Leu Asp Ala Phe Lys Thr Asp Gln Asp Ser
            645                 650                 655

Arg Leu Leu Ile Ala Thr Ser Val Ala Asp Glu Gly Ile Asp Ile Ser
                660                 665                 670

Glu Cys Asn Leu Val Val Leu Tyr Glu Tyr Asp Gly Asn Leu Thr Lys
                675                 680                 685

Met Ile Gln Val Arg Gly Arg Gly Arg Ala Arg Asp Ser Lys Cys Ile
            690                 695                 700

Leu Val Thr Ser Arg Ala Asp Val Val Glu Asn Glu Lys His Asn Cys
705                 710                 715                 720

Tyr Lys Glu Glu Met Met Asn Glu Ala Ile Glu Asn Leu Gln Asn Trp
                725                 730                 735

Asp Glu Thr Ile Phe Ala Arg Lys Ile Gln Glu Leu Gln Met Lys Glu
            740                 745                 750

Asn Val Leu Arg Asp Ser Arg Lys Glu Thr Arg Pro Lys Gly Ala
            755                 760                 765

Glu Gly Lys Lys Asn Leu Leu Cys Gly Lys Cys Lys Ala Tyr Ala Cys
770                 775                 780

Ser Thr Asp Asp Ile Arg Val Ile Lys Glu Ser His His Thr Val Ile
785                 790                 795                 800

Glu Asp Ala Phe Lys Glu Arg Tyr Met Thr Lys Pro His Lys Lys Pro
                805                 810                 815

Val Cys Phe Asp Cys Phe Glu Lys Arg Ser Lys Met Tyr Cys Gln Asn
            820                 825                 830

Ala Asp Cys His His Asp Trp Gly Ile Thr Val Lys Tyr Lys Thr Phe
            835                 840                 845

Asp Asn Leu Pro Val Ile Lys Ile Lys Ser Phe Val Val Glu Asp Val
850                 855                 860

Glu Thr Arg Thr Gln Met Asp Phe Gln Lys Trp Lys Leu Ile Asn Leu
865                 870                 875                 880

Ser Trp Lys Asn Phe Asp Asp Glu Glu Thr Ser Ser
                885                 890
```

<210> SEQ ID NO 21
<211> LENGTH: 912
<212> TYPE: PRT
<213> ORGANISM: Picoides pubescens

<400> SEQUENCE: 21

```
Met Thr Ala Glu Glu Lys Arg Ser Leu Gln Cys Tyr Arg Arg Tyr Ile
1               5                   10                  15

Glu Lys Ser Leu Asn Pro Val Tyr Ile Leu Ser Asn Met Thr Asp Trp
            20                  25                  30

Leu Ser Asp Glu Val Lys Glu Arg Val Arg Lys Glu Glu Glu Lys Gly
        35                  40                  45

Val Thr Ala Ala Ala Ala Met Phe Leu Asp Val Ile Leu Glu Leu Glu
50                  55                  60
```

```
Glu Glu Arg Trp Leu Arg Gly Phe Ile Asp Ala Leu Val Ala Ala Gly
 65                  70                  75                  80

Tyr Thr Gly Leu Ala Glu Ala Ile Glu Asn Trp Asp Phe Ser Lys Leu
                 85                  90                  95

Glu Lys Leu Glu Leu His Arg Glu Leu Leu Lys Arg Ile Glu Ala Thr
            100                 105                 110

Met Leu Glu Val Asp Pro Val Met Val Met Pro Tyr Ile Asn Thr Cys
        115                 120                 125

Leu Ile Glu Arg Glu Cys Asp Glu Ile Leu Gln Ile Ser Glu Tyr Arg
130                 135                 140

Ser Lys Ala Ala Gly Ile Thr Lys Leu Ile Glu Cys Leu Cys Arg Ser
145                 150                 155                 160

Asp Lys Glu Asn Trp Pro Lys Ser Leu Gln Leu Ala Leu Asp Asn Ala
                165                 170                 175

Gly Tyr Tyr Asn Ala Ser Glu Leu Trp Asp Met Arg Glu Glu Asn Phe
            180                 185                 190

Lys Asp Phe Asp Gly Glu Val Gly Asp Ala Ser Glu Asn Ser Phe Glu
        195                 200                 205

Ala Met Val Thr Phe Ser Glu Glu Val Glu Cys Asp Asn Phe Ser Glu
210                 215                 220

Asn Leu Ser Ser Ala Ser Gly Gly Thr Asn Glu Pro Pro Ala Val Tyr
225                 230                 235                 240

Glu Ala Lys Glu Ala Arg Ser Tyr Gln Ile Glu Leu Ala Gln Pro Ala
                245                 250                 255

Ile Asn Gly Lys Asn Thr Leu Ile Cys Ala Pro Thr Gly Ser Gly Lys
            260                 265                 270

Thr Phe Val Ala Leu Leu Ile Cys Glu His His Leu Gln Asn Val Pro
        275                 280                 285

Pro Gly Arg Lys Ala Lys Ile Val Phe Leu Ala Thr Lys Val Pro Val
290                 295                 300

Tyr Glu Gln Gln Gln Asn Val Phe Arg Gln His Phe Glu Arg Gln Gly
305                 310                 315                 320

Tyr Ser Val Arg Gly Ile Cys Gly Glu Thr Val Ala Asn Ile Pro Val
                325                 330                 335

Glu Asn Val Ile Glu Asp Ser Asp Val Ile Val Leu Thr Pro Gln Ile
            340                 345                 350

Leu Val Asn Cys Phe Lys Gln Gly Ile Leu Thr Ser Leu Ser Val Phe
        355                 360                 365

Thr Leu Met Ile Phe Asp Glu Cys His Asn Thr Thr Gly Asn His Pro
370                 375                 380

Tyr Asn Val Leu Met Thr Arg Tyr Leu Glu Gln Lys Phe Ala Ser Ser
385                 390                 395                 400

Ala Ser Gln Leu Pro Gln Ile Val Gly Leu Thr Ala Ser Val Gly Val
                405                 410                 415

Gly Asn Ala Lys Ser Ile Lys Glu Ala Ile Glu His Ile Cys Thr Leu
            420                 425                 430

Cys Cys Tyr Leu Asp Ile Gln Thr Ile Ser Thr Val Arg Glu Asn Lys
        435                 440                 445

Glu Asp Leu Gln Arg Phe Gly Thr Met Pro Glu Thr His Val Arg Trp
450                 455                 460

Val Lys Lys Arg Ala Gln Asn Arg Phe Ala Asp Ile Val Ser Gly Leu
465                 470                 475                 480
```

```
Met Ser Glu Thr Glu Ala Leu Met Arg Arg Ile Tyr Ser Val Asp Thr
            485                 490                 495

Ile Ser Gln Ile Asn Lys Asn Asp Phe Gly Thr Gln Ser Tyr Glu Gln
        500                 505                 510

Trp Ile Val Thr Thr Gln Lys Lys Cys Arg Leu Leu Gln Leu Pro Asp
            515                 520                 525

Lys Glu Lys Glu Ser Ser Val Cys Arg Asp Leu Phe Ile Cys Thr Glu
530                 535                 540

His Leu Arg Lys Phe Asn Asp Ala Leu Met Ile Gly Glu Asp Ala Arg
545                 550                 555                 560

Ile Glu Asp Ala Leu Ala Tyr Leu Thr Glu Phe Phe Thr Asn Val Arg
            565                 570                 575

Asn Gly Pro Tyr Thr Gln Leu Glu Lys Arg Leu Thr Ala Arg Phe Gln
            580                 585                 590

Glu Lys Glu Ala Glu Leu Thr Ala Leu Ser Lys Asp Glu Thr Ser Glu
        595                 600                 605

Asn Pro Lys Leu Glu Glu Leu Ala Cys Ile Leu Asp Glu Ala Tyr Arg
        610                 615                 620

Tyr Asn Ser Asp Thr Arg Thr Leu Ile Phe Ala Lys Thr Arg Ala Leu
625                 630                 635                 640

Val Ala Ala Leu Lys Lys Trp Ile Glu Ala Asn Pro Leu Leu Ser His
            645                 650                 655

Val Lys Pro Gly Val Leu Met Gly His Gly Arg Arg Asp Gln Lys Thr
            660                 665                 670

Gly Met Thr Leu Pro Met Gln Lys Val Ile Leu Asp Ala Phe Arg Thr
            675                 680                 685

Asn Lys Asp Cys Arg Leu Leu Ile Ala Thr Ser Val Ala Asp Glu Gly
        690                 695                 700

Ile Asp Ile Ser Glu Cys Asn Leu Val Val Leu Tyr Glu Tyr Phe Gly
705                 710                 715                 720

Asn Val Thr Lys Met Ile Gln Val Arg Gly Arg Gly Arg Ala Arg Asn
            725                 730                 735

Ser Lys Cys Ile Leu Val Thr Ser Lys Thr Glu Val Val Glu Asn Glu
            740                 745                 750

Lys His Asn His Tyr Lys Glu Glu Met Met Asn Glu Ala Val Glu Gln
        755                 760                 765

Leu Gln Asn Trp Asp Glu Ala Ala Phe Ala Arg Lys Ile His Val Leu
        770                 775                 780

Gln Met Lys Glu Lys Val Leu Arg Asp Phe Lys Lys Lys Glu Thr Arg
785                 790                 795                 800

Pro Gln Leu Val Glu Gly Lys Lys Asn Leu Leu Cys Gly Lys Cys Lys
            805                 810                 815

Ala Tyr Ala Cys Ser Thr Asp Asp Ile Arg Val Ile Lys Val Ser His
            820                 825                 830

His Thr Val Leu Gly Asp Ala Phe Arg Glu Arg Tyr Val Thr Lys Pro
            835                 840                 845

His His Lys Pro Met Lys Phe Asp Cys Phe Glu Lys Lys Ser Lys Met
        850                 855                 860

His Cys Lys Asn Ser Asn Cys His His Asp Trp Gly Ile Thr Val Lys
865                 870                 875                 880

Tyr Lys Met Tyr Asp Asn Leu Pro Val Ile Lys Ile Lys Ser Phe Val
            885                 890                 895

Val Glu Asn Val Glu Thr Gly Arg Gln Met Asp Phe Gln Lys Trp Lys
```

<210> SEQ ID NO 22
<211> LENGTH: 912
<212> TYPE: PRT
<213> ORGANISM: Picoides pubescens

<400> SEQUENCE: 22

Met Thr Ala Glu Glu Lys Arg Ser Leu Gln Cys Tyr Arg Arg Tyr Ile
1               5                   10                  15

Glu Lys Ser Leu Asn Pro Val Tyr Ile Leu Ser Asn Met Thr Asp Trp
            20                  25                  30

Leu Ser Asp Glu Val Lys Glu Arg Val Arg Lys Glu Glu Glu Lys Gly
        35                  40                  45

Val Thr Ala Ala Ala Met Phe Leu Asp Val Ile Leu Glu Leu Glu
    50                  55                  60

Glu Glu Arg Trp Leu Arg Gly Phe Ile Asp Ala Leu Val Ala Ala Gly
65                  70                  75                  80

Tyr Thr Gly Leu Ala Glu Ala Ile Glu Asn Trp Asp Phe Ser Lys Leu
                85                  90                  95

Glu Lys Leu Glu Leu His Arg Glu Leu Leu Lys Arg Ile Glu Ala Thr
            100                 105                 110

Met Leu Glu Val Asp Pro Val Met Val Met Pro Tyr Ile Asn Thr Cys
        115                 120                 125

Leu Ile Glu Arg Glu Cys Asp Glu Ile Leu Gln Ile Ser Glu Tyr Arg
130                 135                 140

Ser Lys Ala Ala Gly Ile Thr Lys Leu Ile Glu Cys Leu Cys Arg Ser
145                 150                 155                 160

Asp Lys Glu Asn Trp Pro Lys Ser Leu Gln Leu Ala Leu Asp Asn Ala
                165                 170                 175

Gly Tyr Tyr Asn Ala Ser Glu Leu Trp Asp Met Arg Glu Glu Asn Phe
            180                 185                 190

Lys Asp Phe Asp Gly Glu Val Gly Asp Ala Ser Glu Asn Ser Phe Glu
        195                 200                 205

Ala Met Val Thr Phe Ser Glu Glu Val Glu Cys Asp Asn Phe Ser Glu
    210                 215                 220

Asn Leu Ser Ser Ala Ser Gly Gly Thr Asn Glu Pro Pro Ala Val Tyr
225                 230                 235                 240

Glu Ala Lys Glu Ala Arg Ser Tyr Gln Ile Glu Leu Ala Gln Pro Ala
                245                 250                 255

Ile Asn Gly Lys Asn Thr Leu Ile Cys Ala Pro Thr Gly Ser Gly Lys
            260                 265                 270

Thr Phe Val Ala Leu Leu Ile Cys Glu His His Leu Gln Asn Val Pro
        275                 280                 285

Pro Gly Arg Lys Ala Lys Ile Val Phe Leu Ala Thr Lys Val Pro Val
    290                 295                 300

Tyr Glu Gln Gln Gln Asn Val Phe Arg Gln His Phe Glu Arg Gln Gly
305                 310                 315                 320

Tyr Ser Val Arg Gly Ile Cys Gly Glu Thr Val Ala Asn Ile Pro Val
                325                 330                 335

Glu Asn Val Ile Glu Asp Ser Asp Val Ile Val Leu Thr Pro Gln Ile
            340                 345                 350

Leu Val Asn Cys Phe Lys Gln Gly Ile Leu Thr Ser Leu Ser Val Phe
        355                 360                 365

```
Thr Leu Met Ile Phe Asp Glu Cys His Asn Thr Thr Gly Asn His Pro
    370                 375                 380

Tyr Asn Val Leu Met Thr Arg Tyr Leu Glu Gln Lys Phe Ala Ser Ser
385                 390                 395                 400

Ala Ser Gln Leu Pro Gln Ile Val Gly Leu Thr Ala Ser Val Gly Val
                405                 410                 415

Gly Asn Ala Lys Ser Ile Lys Glu Ala Ile Glu His Ile Cys Thr Leu
            420                 425                 430

Cys Cys Tyr Leu Asp Ile Gln Thr Ile Ser Thr Val Arg Glu Asn Lys
        435                 440                 445

Glu Asp Leu Gln Arg Phe Gly Thr Met Pro Glu Thr His Val Arg Trp
450                 455                 460

Val Lys Lys Arg Ala Gln Asn Arg Phe Ala Asp Ile Val Ser Gly Leu
465                 470                 475                 480

Met Ser Glu Thr Glu Ala Leu Met Arg Arg Ile Tyr Ser Val Asp Thr
                485                 490                 495

Ile Ser Gln Ile Asn Lys Asn Asp Phe Gly Thr Gln Ser Tyr Glu Gln
                500                 505                 510

Trp Ile Val Thr Thr Gln Lys Lys Cys Arg Leu Leu Gln Leu Pro Asp
            515                 520                 525

Lys Glu Lys Glu Ser Ser Val Cys Arg Asp Leu Phe Ile Cys Thr Glu
530                 535                 540

His Leu Arg Lys Phe Asn Asp Ala Leu Met Ile Gly Glu Asp Ala Arg
545                 550                 555                 560

Ile Glu Asp Ala Leu Ala Tyr Leu Thr Glu Phe Phe Thr Asn Val Arg
                565                 570                 575

Asn Gly Pro Tyr Thr Gln Leu Glu Lys Arg Leu Thr Ala Arg Phe Gln
            580                 585                 590

Glu Lys Glu Ala Glu Leu Thr Ala Leu Ser Lys Asp Glu Thr Ser Glu
        595                 600                 605

Asn Pro Lys Leu Glu Glu Leu Ala Cys Ile Leu Asp Glu Ala Tyr Arg
    610                 615                 620

Tyr Asn Ser Asp Thr Arg Thr Leu Ile Phe Ala Lys Thr Arg Ala Leu
625                 630                 635                 640

Val Ala Ala Leu Lys Lys Trp Ile Glu Ala Asn Pro Leu Leu Ser His
                645                 650                 655

Val Lys Pro Gly Val Leu Met Gly His Gly Arg Arg Asp Gln Lys Thr
            660                 665                 670

Gly Met Thr Leu Pro Met Gln Lys Val Ile Leu Asp Ala Phe Arg Thr
        675                 680                 685

Asn Lys Asp Cys Arg Leu Leu Ile Ala Thr Ser Val Ala Asp Glu Gly
    690                 695                 700

Ile Asp Ile Ser Glu Cys Asn Leu Val Val Leu Tyr Glu Tyr Phe Gly
705                 710                 715                 720

Asn Val Thr Lys Met Ile Gln Val Arg Gly Arg Gly Arg Ala Arg Asn
                725                 730                 735

Ser Lys Cys Ile Leu Val Thr Ser Lys Thr Glu Val Val Glu Asn Glu
            740                 745                 750

Lys His Asn His Tyr Lys Glu Met Met Asn Glu Ala Val Glu Gln
        755                 760                 765

Leu Gln Asn Trp Asp Glu Ala Ala Phe Ala Arg Lys Ile His Val Leu
    770                 775                 780

Gln Met Lys Glu Lys Val Leu Arg Asp Phe Lys Lys Lys Glu Thr Arg
```

```
                785            790           795           800
Pro Gln Leu Val Glu Gly Lys Lys Asn Leu Leu Cys Gly Lys Cys Lys
                    805            810           815

Ala Tyr Ala Cys Ser Thr Asp Asp Ile Arg Val Ile Lys Val Ser His
                820           825            830

His Thr Val Leu Gly Asp Ala Phe Arg Glu Arg Tyr Val Thr Lys Pro
                835           840            845

His His Lys Pro Met Lys Phe Asp Cys Phe Glu Lys Lys Ser Lys Met
        850           855            860

His Cys Lys Asn Ser Asn Cys His His Asp Trp Gly Ile Thr Val Lys
865           870           875                   880

Tyr Lys Met Tyr Asp Asn Leu Pro Val Ile Lys Ile Lys Ser Phe Val
                885            890           895

Val Glu Asn Val Glu Thr Gly Arg Gln Met Asp Phe Gln Lys Trp Lys
                900           905            910
```

<210> SEQ ID NO 23
<211> LENGTH: 3065
<212> TYPE: DNA
<213> ORGANISM: Homo sapiens

<400> SEQUENCE: 23

```
tagttattaa agttcctatg cagctccgcc tccgtccggc ctcatttcct caaaaaatcc     60
ctgctttccc cgctcgccac gccctcctgc tacccggctt taaagctagt gaggcacagc    120
ctgcggggaa cgtagctagc tgcaagcaga ggccggcatg accaccgagc agcgacgcag    180
cctgcaagcc ttccaggatt atatccggaa gaccctggac cctacctaca tcctgagcta    240
catggccccc tggtttaggg aggaagaggt gcagtatatt caggctgaga aaacaacaa     300
gggcccaatg gaggctgcca cacttttcct caagttcctg ttggagctcc aggaggaagg    360
ctggttccgt ggcttttttgg atgccctaga ccatgcaggt tattctggac tttatgaagc    420
cattgaaagt tgggatttca aaaaaattga aaagttggag gagtatagat tacttttaaa    480
acgtttacaa ccagaattta aaccagaat tatcccaacc gatatcattt ctgatctgtc     540
tgaatgttta attaatcagg aatgtgaaga aattctacag atttgctcta ctaaggggat    600
gatggcaggt gcagagaaat tggtggaatg ccttctcaga tcagacaagg aaaactggcc    660
caaaactttg aaacttgctt tggagaaaga aggaacaag ttcagtgaac tgtggattgt     720
agagaaaggt ataaagatg ttgaaacaga agatcttgag gataagatgg aaacttctga    780
catacagatt ttctaccaag aagatccaga atgccagaat cttagtgaga attcatgtcc    840
accttcagaa gtgtctgata caaacttgta cagcccattt aaaccaagaa attaccaatt    900
agagcttgct ttgcctgcta tgaaggaaa aaacacaata atatgtgctc ctacaggttg     960
tggaaaaacc tttgtttcac tgcttatatg tgaacatcat cttaaaaaat cccacaagg   1020
acaaaagggg aaagttgtct ttttttgcgaa tcagatccca gtgtatgaac agcagaaatc   1080
tgtattctca aaatactttg aaagacatgg gtatagagtt acaggcattt ctggagcaac   1140
agctgagaat gtcccagtgg aacagattgt tgagaacaat gacatcatca ttttaactcc   1200
acagattctt gtgaacaacc ttaaaaaggg aacgattcca tcactatcca tctttacttt   1260
gatgatattt gatgaatgcc acaacactag taaacaacac ccgtacaata tgatcatgtt   1320
taattatcta gatcagaaac ttggaggatc ttcaggccca ctgccccagg tcattgggct   1380
gactgcctcg gttggtgttg gggatgccaa aaacacagat gaagccttgg attatatctg   1440
```

```
caagctgtgt gcttctcttg atgcgtcagt gatagcaaca gtcaaacaca atctggagga      1500
actggagcaa gttgtttata agccccagaa gttttttcagg aaagtggaat cacggattag      1560
cgacaaattt aaatacatca tagctcagct gatgagggac acagagagtc tggcaaagag      1620
aatctgcaaa gacctcgaaa acttatctca aattcaaaat agggaatttg aacacagaa       1680 atatgaacaa tggattgtta cagttcagaa agcatgcatg gtgttccaga tgccagacaa      1740
agatgaagag agcaggattt gtaaagccct gtttttatac acttcacatt tgcgaaaata      1800
taatgatgcc ctcattatca gtgagcatgc acgaatgaaa gatgctctgg attacttgaa      1860
agacttcttc agcaatgtcc gagcagcagg attcgaagag attgagcaag atcttactca      1920
gagatttgaa gaaaagctgc aggaactaga aagtgtttcc agggatccca gcaatgagaa      1980
tcctaaactt gaagacctct gcttcatctt acaagaagag taccacttaa acccagagac      2040
aataacaatt ctctttgtga aaaccagagc acttgtggac gctttaaaaa attggattga      2100
aggaaatcct aaactcagtt ttctaaaacc tggcatattg actggacgtg gcaaaacaaa      2160
tcagaacaca ggaatgaccc tcccggcaca gaagtgtata ttggatgcat tcaaagccag      2220
tggagatcac aatattctga ttgccacctc agttgctgat gaaggcattg acattgcaca      2280
gtgcaatctt gtcatccttt atgagtatgt gggcaatgtc atcaaaatga tccaaaccag      2340
aggcagagga agagcaagag gtagcaagtg cttccttctg actagtaatg ctggtgtaat      2400
tgaaaaagaa caaataaaca tgtacaaaga aaaaatgatg aatgactcta ttttacgcct      2460
tcagacatgg gacgaagcag tatttaggga aaagattctg catatacaga ctcatgaaaa      2520
attcatcaga gatagtcaag aaaaaccaaa acctgtccct gataaggaaa ataaaaaact      2580
gctctgcaga aagtgcaaag ccttggcatg ttacacagct gacgtaagag tgatagagga      2640
atgccattac actgtgcttg gagatgcttt taaggaatgc tttgtgagta gaccacatcc      2700
caagccaaag cagttttcaa gttttgaaaa aagagcaaag atattctgtg cccgacagaa      2760
ctgcagccat gactggggaa tccatgtgaa gtacaagaca tttgagattc cagttataaa      2820
aattgaaagt tttgtggtgg aggatattgc aactggagtt cagacactgt actcgaagtg      2880
gaaggacttt cattttgaga agataccatt tgatccagca gaaatgtcca aatgatatca      2940
ggtcctcaat cttcagctac agggaatgag taactttgag tggagaagaa acaaacatag      3000
tgggtataat catggatcgc ttgtaccccct gtgaaaatat attttttaaa aataaaaaaa      3060
aaaaa                                                                  3065

<210> SEQ ID NO 24
<211> LENGTH: 10
<212> TYPE: DNA
<213> ORGANISM: Artificial sequence
<220> FEATURE:
<223> OTHER INFORMATION: synthetic sequence

<400> SEQUENCE: 24
gagggcgggc                                                             10

<210> SEQ ID NO 25
<211> LENGTH: 10
<212> TYPE: DNA
<213> ORGANISM: Artificial sequence
<220> FEATURE:
<223> OTHER INFORMATION: synthetic sequence

<400> SEQUENCE: 25
gagttcttgc                                                             10
```

```
<210> SEQ ID NO 26
<211> LENGTH: 14
<212> TYPE: DNA
<213> ORGANISM: Artificial sequence
<220> FEATURE:
<223> OTHER INFORMATION: synthetic sequence

<400> SEQUENCE: 26
gctttcgttt tcca                                                      14

<210> SEQ ID NO 27
<211> LENGTH: 14
<212> TYPE: DNA
<213> ORGANISM: Artificial sequence
<220> FEATURE:
<223> OTHER INFORMATION: synthetic sequence

<400> SEQUENCE: 27
gctaacgtga gcca                                                      14
```